United States Patent
Wall et al.

(10) Patent No.: US 10,046,050 B2
(45) Date of Patent: *Aug. 14, 2018

(54) TARGETING IMMUNOTHERAPY FOR AMYLOIDOSIS

(71) Applicant: UNIVERSITY OF TENNESSEE RESEARCH FOUNDATION, Knoxville, TN (US)

(72) Inventors: Jonathan S. Wall, Knoxville, TN (US); Stephen J. Kennel, Kingston, TN (US); James S. Foster, Knoxville, TN (US)

(73) Assignee: UNIVERSITY OF TENESSEE RESEARCH FOUNDATION, Knoxville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/052,772

(22) Filed: Feb. 24, 2016

(65) Prior Publication Data

US 2016/0243230 A1     Aug. 25, 2016

Related U.S. Application Data

(63) Continuation-in-part of application No. PCT/US2015/046523, filed on Aug. 24, 2015.
(Continued)

(51) Int. Cl.
*A61K 38/17* (2006.01)
*A61P 27/02* (2006.01)
(Continued)

(52) U.S. Cl.
CPC .... *A61K 39/39583* (2013.01); *A61K 38/1716* (2013.01); *A61K 47/48346* (2013.01);
(Continued)

(58) Field of Classification Search
None
See application file for complete search history.

(56) References Cited

U.S. PATENT DOCUMENTS 4,235,871 A   11/1980   Papahadjopoulos et al.
4,501,728 A   2/1985    Geho et al.
(Continued)

FOREIGN PATENT DOCUMENTS

WO   1999060024      11/1999
WO   2010011999 A2   1/2010
(Continued)

OTHER PUBLICATIONS

Jaishankar et al., "Characterization of a proteolytically stable D-peptide that suppresses herpes simplex virus 1 infection: implications for the development of entry-based antiviral therapy", J Virol. Feb. 2015;89(3):1932-8. doi: 10.1128/JVI.02979-14. Epub Nov. 26, 2014.
(Continued)

*Primary Examiner* — Adam Weidner
*Assistant Examiner* — Aurora M Fontainhas
(74) *Attorney, Agent, or Firm* — FisherBroyles, LLP; Jason M. Pass

(57) ABSTRACT

Disclosed are methods and compositions for targeting antibodies to amyloid deposits. For example, amyloid-reactive peptides that bind amyloid deposits are administered to a subject. Antibodies to the amyloid-reactive peptides are then administered to the subject. Upon administration of the antibodies, the amyloid-reactive peptides bind the antibodies and thus pre-target the antibodies to the amyloid deposits. In other examples, an amyloid-reactive fusion peptide contains an epitope of a known antibody. When the fusion peptide is administered to a subject, the fusion peptide binds amyloids in the subject. Administration to the subject of the known antibody that binds the epitope of the fusion peptide then targets the antibody to the amyloid deposit to which the fusion peptide is bound.

20 Claims, 39 Drawing Sheets

Related U.S. Application Data

(60) Provisional application No. 62/041,888, filed on Aug. 26, 2014.

(51) Int. Cl.
    *A61K 39/395*     (2006.01)
    *C07K 16/18*     (2006.01)
    *A61K 47/48*     (2006.01)
    *C07K 14/47*     (2006.01)
    *A61K 39/00*     (2006.01)

(52) U.S. Cl.
CPC .... *A61K 47/48723* (2013.01); *C07K 14/4711* (2013.01); *C07K 16/18* (2013.01); *A61K 2039/545* (2013.01); *C07K 2319/00* (2013.01)

(56) References Cited

U.S. PATENT DOCUMENTS

| | | |
|---|---|---|
| 4,837,028 A | 6/1989 | Allen |
| 4,902,505 A | 2/1990 | Pardridge et al. |
| 4,957,735 A | 9/1990 | Huang |
| 5,004,697 A | 4/1991 | Pardridge |
| 5,019,369 A | 5/1991 | Presant et al. |
| 5,055,303 A | 10/1991 | Riley, Jr. |
| 5,091,309 A | 2/1992 | Schlesinger et al. |
| 5,188,837 A | 2/1993 | Domb |
| 5,217,879 A | 6/1993 | Huang et al. |
| 5,254,342 A | 10/1993 | Shen et al. |
| 5,268,164 A | 12/1993 | Kozarich et al. |
| 5,271,961 A | 12/1993 | Mathiowitz et al. |
| 5,413,797 A | 5/1995 | Khan et al. |
| 5,506,206 A | 4/1996 | Kozarich et al. |
| 5,514,670 A | 5/1996 | Friedman et al. |
| 5,534,496 A | 7/1996 | Lee et al. |
| 8,791,243 B2 | 7/2014 | Schenk et al. |
| 2002/0019335 A1 | 2/2002 | Solomon et al. |
| 2002/0031527 A1 | 3/2002 | Wu et al. |
| 2002/0115717 A1 | 8/2002 | Gervais et al. |
| 2004/0146512 A1 | 7/2004 | Rosenthal |
| 2009/0017017 A1 | 1/2009 | Rasmussen et al. |
| 2010/0003259 A1 | 1/2010 | Ruben et al. |
| 2012/0321555 A1* | 12/2012 | Schenk .............. A61K 51/1018 424/1.49 |
| 2013/0022546 A1 | 1/2013 | Wall et al. |
| 2013/0210168 A1 | 8/2013 | Mead |
| 2015/0158937 A1 | 6/2015 | Schenk et al. |
| 2016/0243230 A1 | 8/2016 | Wall et al. |

FOREIGN PATENT DOCUMENTS

| | | |
|---|---|---|
| WO | 2011119608 | 9/2011 |
| WO | 2012037498 | 3/2012 |

OTHER PUBLICATIONS

Ostrander, et al., Anti-viral activity of human recombinant heparin-binding proteins HBNF and MK, Biochem Biophys Res Commun. Dec. 15, 1992;189(2):1189-95.

Schmidtke et al.,"Binding of a N,N'-bisheteryl derivative of dispirotripiperazine to heparan sulfate residues on the cell surface specifically prevents infection of viruses from different families", Virology. Jun. 20, 2003;311(1):134-43.

Tiwari et al., "Anti-heparan sulfate peptides that block herpes simplex virus infection in vivo", J Biol Chem. Jul. 15, 2001;286(28):25406-15. doi: 10.1074/jbc.M110.201103. Epub May 19, 2011.

International Search Report and Written Opinion issued in PCT/US2015/046523 dated Jan. 28, 2016 (16 pages).

Invitation to Pay Additional Fees issued in PCT/US2015/046523 dated Nov. 5, 2015 (3 pages).

International Patent Application No. PCT/US2015/046523, Applicant University of Tennessee Research Foundation.

O'Nuallain et al., Phage display and peptide mapping of an immunoglobulin light chain fibril-related conformational epitope, Biochemistry. Nov. 13, 2007;46(45):13049-58. Epub Oct. 18, 2007.

O'Nuallain et al., "Localization of a conformational epitope common to non-native and fibrillar immunoglobulin light chains", Biochemistry. Feb. 6, 2007;46(5):1240-7.

Wall et al., "Preclinical Validation of the Heparin-Reactive Peptide p5+14 as a Molecular Imaging Agent for Visceral Amyloidosis", Molecules. Apr. 27, 2015;20(5):7657-82. doi: 10.3390/molecules20057657.

Wall et al., "Generation and Characterization of anti-AA Amyloid-Specific Monoclonal Antibodies", Frontiers of Immunology, 2011, doi:10.3389/fimmu.2011.00032.

Office Action dated Sep. 9, 2016, in U.S. Appl. No. 14/801,717, filed Jul. 16, 2015, First Named Inventor Jonathan S. Wall (18 pages).

Borst et al., "A peptide inhibitor of cytomegalovirus infection from human hemofiltrate", Antimicrob Agents Chemother. Oct. 2013;57(10):4751-60. doi: 10.1128/AAC.00854-13. Epub Jul. 15, 2013.

U.S. Appl. No. 14/801,717, inventor Jonathan S. Wall.

International Search Report and Written Opinion issued in PCT/US17/15905 dated Jun. 9, 2017, Applicant University of Tennessee Research Foundation (19 pages).

International Search Report and Written Opinion issued in PCT/US17/28828 dated Sep. 13, 2017, Applicant University of Tennessee Research Foundation (21 pages).

Baden et al., "Light chain amyloidosis—current findings and future prospects", Curr Protein Pept Sci. Oct. 2009;10(5):500-508.

Supplementary European Search Report issued in EP 15836458.8 dated Apr. 5, 2018 (10 pages).

Wall et al., "Development and evaluation of agents for targeting visceral amyloid", Journal of Drug Targeting, 33(4):807-814, 2011.

Funke et al., "Peptides for Therapy and Diagnosis of Alzheimer's Disease", Current Pharmaceutical Design, 18(6):755-767, 2012.

Goure et al., "Targeting the proper amyloid-beta neuronal toxins: a path forward for Alzheimer's disease immunotherapeutics", Alzheimers Res Ther, 6(4):42, 2014.

Lobello et al., "Targeting Beta Amyloid: A Clinical Review of Immunotherapeutic Approaches in Alzheimer's Disease", International Journal of Alzheimer's Disease, 6(4):S305-14, 2012.

Wall et al., "Pretargeting immunotherapy: a novel treatment approach for systemic amyloidosis", Pharmaceutical Patent Analyst, 6(5):215-223, 2017.

Wall et al., "A bifunctional peptide, "peptope", for pre-targeting antibody 7D8 to systemic amyloid deposits", Amyloid, 24(16):22-23, 2017.

\* cited by examiner

FIG. 15A Kidney
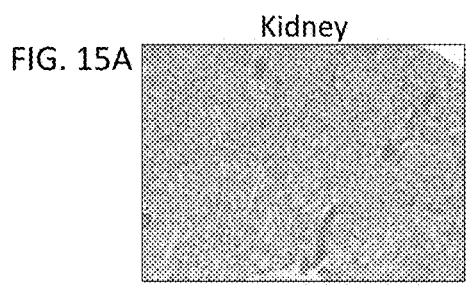
FIG. 15B Spleen
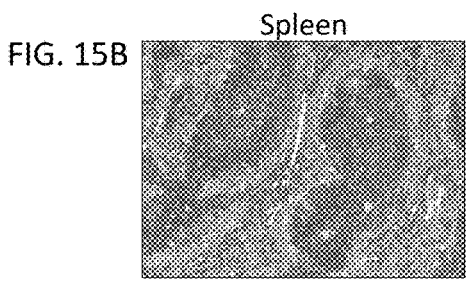
FIG. 15C Intestines
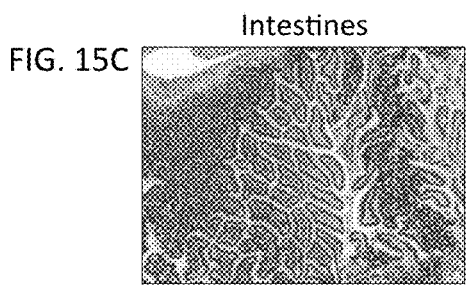
FIG. 15D Muscle/Nerve
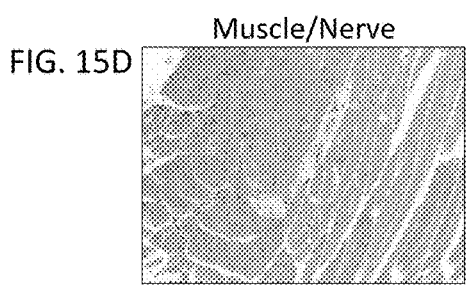
FIG. 15E Liver
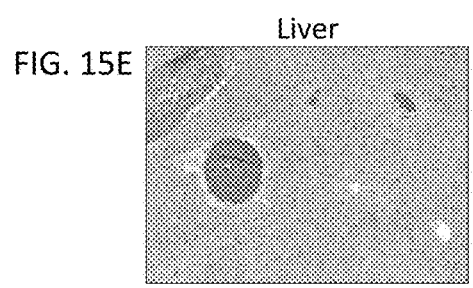
FIG. 15F Stomach
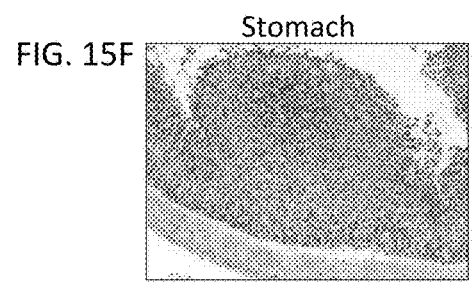
FIG. 15G Heart
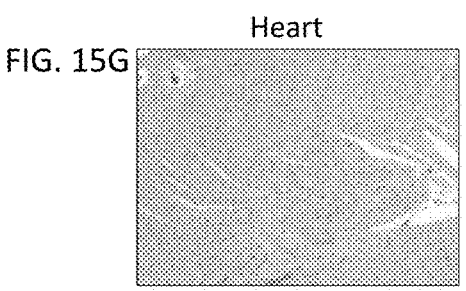
FIG. 15H Pancreas/Islet
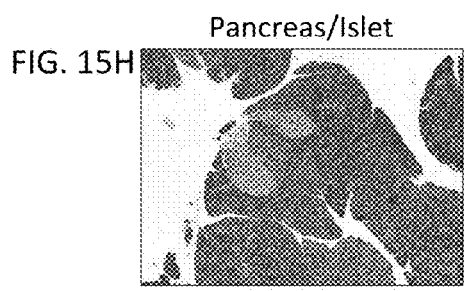

Liver

Heart

Kidney

Spleen

Liver

Kidney

Heart

Spleen

Peptope p66

Control, peptide p5+14

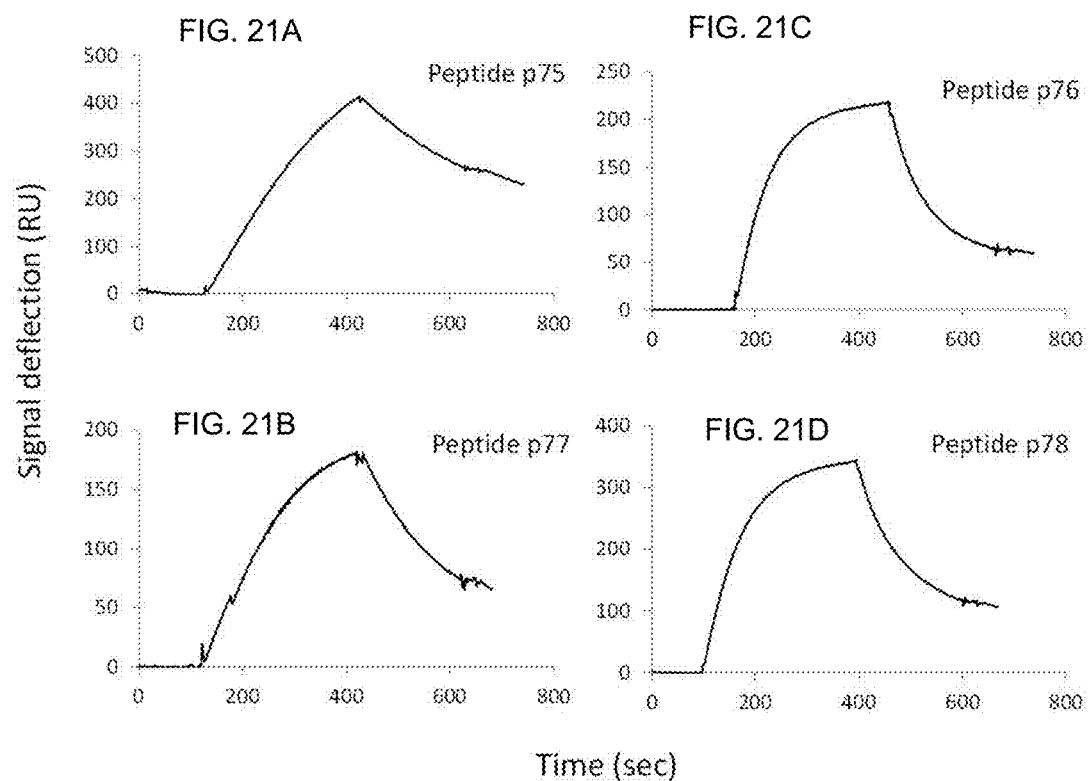

Congo red (esophagus)

7D8 IHC (esophagus)

Ctrl peptide p5 + 7D8 IHC (esophagus)

Peptope p75 + 7D8 IHC (esophagus)

Congo red (heart)

7D8 IHC (heart)

Ctrl peptide p5 + 7D8 IHC (heart)

Peptope p75 + 7D8 IHC (heart)

Congo red (nerve)

7D8 IHC (nerve)

Ctrl peptide p5 + 7D8 IHC (nerve)

Peptope p75 + 7D8 IHC (nerve)

Congo red (small bowel)

7D8 IHC (small bowel)

Ctrl peptide p5 + 7D8 IHC
(small bowel)

Peptope p75 + 7D8 IHC
(small bowel)

Congo red (heart)

7D8 IHC (heart)

Ctrl peptide p5 + 7D8 IHC
(heart)

Peptope p75 + 7D8 IHC
(heart)

Congo Red (heart)

7D8 IHC (heart)

Ctrl peptide p5 + 7D8 IHC (heart)

Peptope p75 + 7D8 IHC (heart)

Congo red (thyroid)

7D8 IHC (thyroid)

Ctrl peptide p5 + 7D8 IHC (thyroid)

Peptope p75 + 7D8 IHC (thyroid)

Congo red (kidney)

7D8 IHC (kidney)

Ctrl peptide p5 + 7D8 IHC
(kidney)

Peptope p75 + 7D8 IHC
(kidney)

TARGETING IMMUNOTHERAPY FOR AMYLOIDOSIS

CROSS-REFERENCE TO RELATED APPLICATIONS

This application is a continuation-in-part application and claims priority benefit to International Patent Application No. PCT/US2015/046523, filed Aug. 24, 2015, titled "Targeting Immunotherapy for Amyloidosis," which claims priority benefit to U.S. Provisional Application No. 62/041,888, filed Aug. 26, 2014, titled "Pre-Targeting Immunotherapy for Amyloidosis." The entire disclosure of both of the above-identified priority applications are hereby fully incorporated herein by reference.

STATEMENT OF GOVERNMENT SUPPORT

This invention was made with government support under grant number R01DK079984 awarded by National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Mar. 29, 2016, is named 05820.P004U1_SL.txt and is 19,001 bytes in size.

TECHNICAL FIELD

The present invention relates to antibodies that bind amyloid-reactive peptides and amyloid-reactive fusion peptides, which in turn bind amyloid deposits. The combination of antibodies and amyloid-reactive peptides may be used to treat multiple forms of amyloidosis by inducing a cellular response to clear amyloid deposits from the tissues of affected subjects.

BACKGROUND

Amyloidosis is a fatal protein-folding disorder characterized by the aggregation and deposition of proteinaceous fibrils and heparan sulfate proteoglycan in vital organs and tissues (Merlini, G. et al. (2003) *N. Engl. J. Med.* 349, 583-596; Merlini, G. et al. (2004) *J. Intern. Med.* 255, 159-178; De Lorenzi, E. et al. (2004) *Curr. Med. Chem.* 11, 1065-1084; Merlini, G. (2004) *Neth. J. Med.* 62, 104-105). The unrelenting accumulation of amyloid invariably leads to organ dysfunction and severe morbidity or death. The deposits can be cerebral, as in patients with Alzheimer's, Huntington's or prion diseases, or peripheral such as seen in patients with light chain (AL) amyloidosis and type 2 diabetes. Further sub-grouping into localized or systemic indicates whether the precursor protein is produced locally (at the site of deposition) or circulates in the blood stream and deposits at distant anatomic sites, respectively (Westermark, P. et al. (2007) *Amyloid.* 14, 179-183). Amyloid can affect any organ or tissue but the kidneys, pancreas, liver, spleen, nervous tissue and heart constitute the major sites of deposition in patients with familial or sporadic forms of peripheral amyloid disease. Alzheimer's disease currently affects more than 4 million Americans and this figure is estimated to increase to more than 16 million by the year 2050. It is by far the most common form of amyloidosis and poses the greatest socioeconomic impact. In contrast, the peripheral (or systemic) amyloidoses are orphan disorders but account for more than 5,000 new patients annually in the USA alone.

Of these, the major peripheral amyloidosis is light chain-associated (AL) amyloidosis, a sporadic monoclonal plasma cell dyscrasia resulting in the deposition of fibrils composed of immunoglobulin light chain proteins. AL accounts for approximately two thirds of all peripheral amyloid cases and has a calculated incidence of ~1.4 per 100,000 persons per year in the USA, which is comparable to that of acute lymphocytic and chronic myeloid leukemia (Group, U. S. C. S. W. (2007) United States Cancer Statistics: 1999-2003 Incidence and Mortality Web-Based Report, U.S. Department of Health and Human Services Centers for Disease Control and Prevention National Cancer Institute, Atlanta). Although AL is one fifth as common as the related plasma cell dyscrasia multiple myeloma it is arguably more devastating with a median survival of only 13.2 months due partly to the rapidly progressive nature of the organ destruction, the lack of effective anti-amyloid therapeutics and the inability to effectively diagnose the disease before organ failure occurs. Fewer than 5% of all AL patients survive 10 years or more from the time of diagnosis (Comenzo, R. L. et al. (2002) *Blood* 99, 4276-4282). Moreover, in patients with cardiac AL amyloidosis the median survival is less than 5 months.

Another prevalent form of peripheral amyloidosis in the U.S. is inflammation-associated (AA) amyloidosis, which is associated with chronic inflammatory disorders such as arthritis, tuberculosis and Familial Mediterranean Fever. The incidence of AA is greatest in certain regions of Europe and the frequency varies among ethnic groups (Buck, F. S. et al. (1989) *Mod. Pathol.* 2, 372-377). In areas where Familial Mediterranean Fever is prevalent and goes untreated, the incidence of AA can be 100%. In Europe the incidence, based on autopsy studies performed in the Denmark, is estimated to be 0.86% (Lofberg, H. et al. (1987) *Acta pathologica, microbiologica, et immunologica Scandinavica* 95, 297-302); however, in patients with rheumatoid or psoriatic arthritis the occurrence of AA can be as high as 26%. Such a high prevalence may warrant a screening program to detect the disease earlier. Deposition of amyloid is associated with a sustained increase in the plasma concentration of serum amyloid protein A (sAA), the precursor of the amyloid fibrils (Rocken, C. et al. (2002) *Virchows Arch.* 440, 111-122). AA differs from AL in the type of precursor protein that is deposited but both share common mechanistic features associated with fibril formation and deposition (Rocken, C. et al. (2006) *J. Pathol.* 210, 478-487; Rocken, C. et al. (2001) *Am. J. Pathol.* 158, 1029-1038).

In addition to the disorders in which the etiopathology of amyloid is well established, fibrillar deposits with the structural and tinctorial properties of amyloid have been identified in other syndromes although their relevance to the disease state has yet to be established. In type 2 diabetes for example, islet amyloid precursor protein (IAPP) deposits as amyloid in the Islets of Langerhans (Jaikaran, E. T. et al. (2001) *Biochim. Biophys. Acta* 1537, 179-203). The aggregation of IAPP results in oligomeric structures that are toxic to pancreatic cells (Lin, C. Y. et al. (2007) *Diabetes* 56, 1324-1332). Thus, it is suggested that the formation of IAPP amyloid in type 1 diabetic patients contributes to β cell destruction and ushers in the transition to insulin dependence (Jaikaran, E. T. et al. (2001) *Biochim. Biophys. Acta* 1537, 179-203). In another example, plaques containing amyloid fibrils composed of apolipoprotein A-I have been identified in over half of patients with atherosclerotic carotid arteries (Westermark, P. et al. (1995) *Am. J. Pathol.* 147, 1186-1192; Mucchiano, G. I. et al. (2001) *J. Pathol.* 193, 270-275). The deposition of these fibrils was more common in older patients but apoA-I is undoubtedly present early in plaque development (Vollmer, E. et al. (1991) *Virchows Arch. A. Pathol. Anat. Histopathol.* 419, 79-88). As a final example, Apo-A-I amyloid was also recently identified in knee joint menisci obtained from patients having knee replacement surgery and may contribute to the physical deterioration of the joint (Solomon, A. et al. (2006) *Arthritis Rheum.* 54, 3545-3550).

In total, more than 29 proteins have been chemically or serologically identified as constituents of fibrils in amyloid deposits. It is the nature of these proteins that differentiate the diseases, determine the treatment, and establish the prognosis. Although amyloid fibrils are associated with a clinically heterogeneous group of diseases and can form from structurally distinct and functionally diverse precursor proteins, the deposits themselves share a number of remarkably similar characteristics including fibril structure, fibril epitopes and accrual of similar accessory molecules including heparan sulfate proteoglycans (HSPGs). Amyloid is a heterogeneous complex that includes, in addition to fibrils, glycosaminoglycans (GAGs) and in particular the perlecan HSPG (Ancsin, J. B. (2003) *Amyloid* 10, 67-79; Ailles, L. et al. (1993) *Lab. Invest.* 69, 443-448; Kisilevsky, R. (1994) *Mol. Neurobiol.* 9, 23-24; Kisilevsky, R. (1990) *Lab. Invest.* 63, 589-591; Snow, A. D. et al. (1987) *Lab. Invest.* 56, 120-123; Li, J. P. et al. (2005) *Proc. Natl. Acad. Sci. USA* 102, 6473-6477). A partial list of amyloid and amyloid related disorders is provided in Table 1 (below).

To date, the most effective therapeutic intervention for removing amyloid deposits, which may promote recovery of organ function and lead to an improved prognosis, involves the use of amyloid-reactive antibodies as a means of immunotherapy. Several immunotherapies (antibodies) have been developed for amyloid-related diseases, including monoclonal antibody 11-1F4 for the treatment of AL amyloidosis, NEOD001 for patients with AL amyloidosis, GSK2398852 (anti-SAP monoclonal antibody) for amyloidosis, Solanezumab for Alzheimer's disease, intravenous IgG (IVIG) for Alzheimer's disease, and Bapineuzumab for Alzheimer's disease. Each of these approaches has limitations or has not been validated in extensive clinical trials (Phase 2/3).

SUMMARY

In certain example aspects, provided are amyloid-reactive peptides that bind amyloid deposits. For example, the amyloid-reactive peptides bind one or more of the amyloids identified in Table 1. In certain example embodiments, provided are amyloid-reactive fusion peptides that bind amyloid deposits. The amyloid-reactive fusion peptides are fused, for example, to an epitope of a known antibody. In certain example aspects, provided are antibodies that bind the amyloid-reactive peptides. Also provided are the antibodies, including the amyloid-reactive antibodies, that bind the epitope of amyloid-reactive fusion peptides.

In certain example aspects, provided is a method of targeting an amyloid deposit for clearance. The method includes, for example, contacting an amyloid deposit with an amyloid-reactive peptide that binds amyloid deposits. The method also includes contacting the amyloid-reactive peptide with an antibody that binds the amyloid-reactive peptide. Contacting the amyloid-reactive peptide with the antibody that binds the amyloid-reactive peptide pre-targets the amyloid deposit for clearance. Thereafter, pre-targeting of the amyloid deposit results in clearance of the deposit.

TABLE 1

Partial List of Amyloid and Amyloid-Related Disorders

| Amyloid type | Precursor | Systemic (S) or Localized (L) | Aquired (A)/ Herditary (H)/ Organs | Syndrome |
|---|---|---|---|---|
| AL | Immunoglobulin light chain | S, L | A/All but *CNS | Primary, Myleoma |
| AH | Immunoglobulin heavy chain | S, L | A/All but CNS | |
| A$\beta_2$M | $\beta_2$-microglobulin | S, | A/Musculoskeletal | Hemodialysis |
| ATTR | Transthyretin variants | S, L | A/Heart, tenosynovium | Familial, Senile systemic |
| Wild type TTR | Transthyretin | S | H/heart, eye, leptomen | Aging |
| AA | Serum amyloid protein A | S | A/All but CNS | Reactive, chronic inflammation |
| AApoAI | Apolipoprotein AI | S | H/ heart, liver etc | Familial |
| AApoAII | Apolipoprotein AII | S | H/Kidney | |
| AGel | Gelsolin | S | H/PNS, cornea | Familial |
| ALys | Lysozyme | S | H/Kidney | Familial |
| ALect2 | leukocyte chemotactic factor 2 | S | A/Kidney | Renal amyloid |
| AFib | Fibrinogen α variants | S | H/Kidney | Familial |
| ACys | Cystatin variants | S | H/*PNS, skin | |
| ACal | (Pro)calcitonin | L | A/Thyroid | Thyroid tumors |
| AMed | Lactadherin | L | A/Senile aortic media | Aging |
| AIAPP | Islet amyloid polypeptide | L | A/Islets of Langerhans | Type 2 diabetes |
| APro | Prolactin | L | A/Pituitary | Aging pituitary |
| AIns | Insulin | L | A/Injection site | Iatrogenic |
| APrP | Prion protein | L | A/H/, brain | Spongiform encephalopathies |
| Aβ | Aβ precursor protein | L | A/H/brain | Alzheimer's disease and aging |

*PNS = peripheral nervous system; CNS = central nervous system

In certain example aspects, provided is a method for clearing amyloid deposits in a subject. The method includes, for example, selecting a subject having amyloidosis and administering to the subject an amyloid-reactive peptide that binds to the amyloid deposits. In addition to administering amyloid-reactive peptide, the method includes administering to the subject an antibody, or a functional group or fragment thereof, which binds to the amyloid-reactive peptide. Administering the antibody or functional fragment thereof to the subject results in clearance of the amyloid deposit in the subject, thereby treating the subject.

In certain example aspects, the amyloid-reactive peptide includes an epitope bound to the amyloid-reactive peptide. The epitope, for example, is an epitope of a known antibody. When administered to a subject, for example, binding of the antibody or functional fragment thereof to the epitope results in increased clearance of the amyloid deposit. In certain example aspects, the epitope includes a motif for binding an amyloid-reactive antibody. For example, the antibody is an amyloid-reactive antibody and thus can bind the epitope of the amyloid deposit directly.

In certain example aspects, provided is a method for clearing amyloid deposits in a subject. The method includes, for example, selecting a subject with amyloidosis and administering to the subject an effective amount of an amyloid-reactive fusion peptide. The amyloid-reactive fusion peptide comprises an amyloid-reactive peptide that binds to amyloid deposits and an epitope fused to the amyloid-reactive peptide that binds an antibody. The method also includes administering to the subject an effective amount of the antibody or fragment thereof. Binding of the antibody or fragment thereof to the amyloid-reactive fusion peptide results in clearance of the amyloid deposit.

In certain example aspects, provided is a kit. The kit includes, for example, an effective amount of the amyloid-reactive peptides or fusion peptides and an effective amount of antibodies that bind the amyloid-reactive peptides or fusion peptides. The kit also optionally includes instructions for using the kit, such as for administering the amyloid-reactive peptides, fusion peptides, and antibodies as described herein.

In certain example aspects, provided is a substantially pure antibody having binding affinity for an amyloid-reactive peptide, such as the amyloid-reactive peptides identified in Table 2.

These and other aspects, objects, features and advantages of the example embodiments will become apparent to those having ordinary skill in the art upon consideration of the following detailed description of illustrated example embodiments.

BRIEF DESCRIPTION OF THE FIGURES

FIG. 6A shows biotinyl-p5+14 (no mAb) co-localization with amyloid (left panel) and corresponding Congo red-stained tissue (right panel). FIG. 6B likewise shows, in a second example, biotinyl-p5+14 (no mAb) co-localization with amyloid (left panel) and corresponding Congo red-stained tissue (right panel).

FIG. 7A shows mAB clone 4 binding in the presence (left panel) and the absence (right panel) of peptide p5+14. FIG. 7B shows mAB clone 5 binding in the presence (left panel) and the absence (right panel) of peptide p5+14. FIG. 7C shows mAB clone 12 binding in the presence (left panel) and the absence (right panel) of peptide p5+14. FIG. 7D shows mAB clone 13 binding in the presence (left panel) and the absence (right panel) of peptide p5+14.

FIG. 8A shows one predicted structure. FIG. 8B shows a second predicted structure.

FIG. 14A shows a microautoradiograph (top panel) and a corresponding Congo-red micrograph (bottom panel) in spleen tissue. FIG. 14B shows a microautoradiograph (top panel) and a corresponding Congo-red micrograph (bottom panel) in pancreatic tissue. FIG. 14C shows a microautoradiograph (top panel) and a corresponding Congo-red micrograph (bottom panel) in kidney tissue. FIG. 14D shows a microautoradiograph (top panel) and a corresponding Congo-red micrograph (bottom panel) in heart tissue. FIG. 14E shows a microautoradiograph (top panel) and a corresponding Congo-red micrograph (bottom panel) in liver tissue.

FIGS. 15A-15H are a series of microautoradiographs demonstrating that p66 injected into healthy, wild-type mice does not bind to any of the tissues examined in vivo, in accordance with certain example embodiments. More particularly, FIG. 15A shows lack of binding of p66 in healthy kidney tissue. FIG. 15B shows lack of binding of p66 in healthy spleen tissue. FIG. 15C shows lack of binding of p66 in healthy intestinal tissue. FIG. 15D shows lack of binding of p66 in healthy muscle/nerve tissue. FIG. 15E shows lack of binding of p66 in healthy liver tissue. FIG. 15F shows lack of binding of p66 in healthy stomach tissue. FIG. 15G shows lack of binding of p66 in healthy heart tissue. FIG. 15H shows lack of binding of p66 in healthy pancreatic/islet tissue.

FIG. 17A shows biotinyl-12-3 mAB immunohistochemistry staining (top panel) and $^{125}$I-11-1F4 autoradiography (bottom panel) in liver tissue. FIG. 17B shows biotinyl-12-3 mAB immunohistochemistry staining (top panel) and $^{125}$I-11-1F4 autoradiography (bottom panel) in heart tissue. FIG. 17C shows biotinyl-12-3 mAB immunohistochemistry staining (top panel) and $^{125}$I-11-1F4 autoradiography (bottom panel) in kidney tissue. FIG. 17D shows biotinyl-12-3 mAB immunohistochemistry staining (top panel) and $^{125}$I-11-1F4 autoradiography (bottom panel) in spleen tissue.

FIG. 18A shows biotinyl-12-3 mAB immunohistochemistry staining (top panel) and $^{125}$I-11-1F4 autoradiography (bottom panel) in liver tissue. FIG. 18B shows biotinyl-12-3 mAB immunohistochemistry staining (top panel) and $^{125}$I-11-1F4 autoradiography (bottom panel) in heart tissue. FIG. 18C shows biotinyl-12-3 mAB immunohistochemistry staining (top panel) and $^{125}$I-11-1F4 autoradiography (bottom panel) in kidney tissue. FIG. 18D shows biotinyl-12-3 mAB immunohistochemistry staining (top panel) and $^{125}$I-11-1F4 autoradiography (bottom panel) in spleen tissue.

FIG. 19A shows results from pre-injection with p66. FIG. 19B shows results from pre-injection with p5+15.

FIGS. 21A-21D are a series of sensorgrams showing data for mAb 7D8 binding to amino-coupled peptopes by using surface plasmon resonance (SPR), in accordance with certain example embodiments. FIG. 21A shows binding of 7D9 to peptope p75. FIG. 21B shows binding to p77. FIG. 21C shows binding to p76. FIG. 21D shows binding to p78.

FIG. 46A and FIG. 46B show images of individual cells taking up "green" amyloid. Likewise, FIG. 46C and FIG. 46D show images of cells taking up "green" amyloid.

DETAILED DESCRIPTION OF THE EXAMPLE EMBODIMENTS

Overview

Figure 1A:
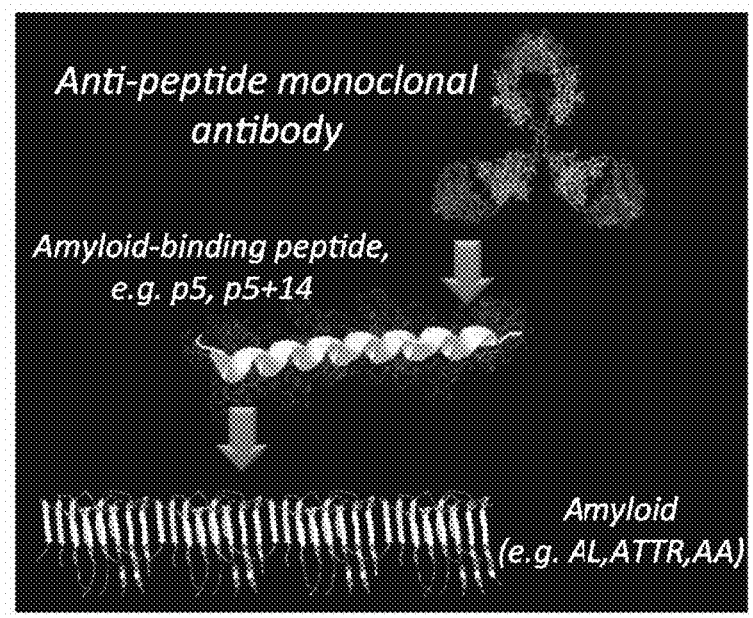
FIG. 1A is a schematic drawing showing targeting of antibodies to amyloids via amyloid-reactive peptides (e.g., p5 or p5+14), in accordance with certain example embodiments.

Described herein are compositions that include amyloid-reactive peptides, amyloid-reactive fusion peptides, and antibodies to amyloid-reactive peptides and fusion peptides. Also described herein are methods of using the same for the treatment of amyloidosis. For example, the amyloid-reactive peptides, amyloid-reactive fusion peptides, and antibodies may be used to target amyloid deposits in subjects with amyloidosis. By targeting amyloid deposits in the subject, the amyloid-reactive peptides, amyloid-reactive fusion peptides, antibodies, and methods described herein initiate clearance of the amyloid deposits by the subject's own immune system. That is, the amyloid-reactive peptides, amyloid-reactive fusion peptides, antibodies, and methods described thus treat the subject having amyloidosis.

More particularly, amyloid-reactive peptides and fusion peptides are provided that bind to one or more components of the amyloid (e.g., protein fibrils or glycosaminoglycans) that make up an amyloid deposit. For example, the amyloid-reactive peptides and fusion peptides may be pan amyloid-reactive peptides and fusion peptides that bind to multiple amyloid deposit types.

Also provided are antibodies that bind amyloid-reactive peptides and fusion peptides. For example, the antibodies are raised against one or more of the amyloid-reactive peptides such that the antibodies bind to the one or more amyloid-reactive peptides. When one or more of the amyloid-reactive peptides are administered to a subject, for example, the amyloid-reactive peptides localize to—and bind to—amyloid deposits within the subject. Thereafter, when the antibodies are administered to the subject, the antibodies bind to the amyloid-reactive peptides. As such, the antibodies bind to the amyloid deposit indirectly via the amyloid-reactive peptides.

Additionally or alternatively, in certain examples the amyloid-reactive peptide is fused to an "epitope" peptide of a known (corresponding) antibody to form an amyloid-reactive fusion peptide. For example, the epitope may be fused to the C-terminal end of the amyloid-reactive peptide. With the fused epitope, the antibody recognizes and binds to the peptide epitope (the "peptope") of the amyloid-reactive peptide. When such peptope-containing amyloid-reactive fusion peptides are administered to a subject, for example, the peptides localize and bind to amyloid deposits within the subject. Administration of the antibodies to the subject then results in binding of the antibodies to the amyloid-reactive fusion peptides via the peptope.

Additionally or alternatively, in certain examples the epitope portion of the amyloid-reactive peptide is a known epitope of an amyloid-reactive antibody. That is, the antibody is known to bind one or more amyloid proteins. Hence, fusion of the amyloid-reactive antibody epitope to the amyloid-reactive peptide allows binding of amyloid-reactive antibody to the amyloid-reactive fusion peptide via the amyloid-reactive antibody epitope. When such amyloid-reactive fusion peptides containing amyloid-reactive antibody epitopes are administered to a subject, the peptides localize and bind to amyloid deposits within the subject. Administration of the amyloid-reactive antibodies to the subject then results in binding of the amyloid-reactive antibodies to the amyloid-reactive fusion peptides via the peptope. Further, because the antibody is an amyloid-reactive antibody, the antibody also binds to amyloid deposits directly.

In such fusion peptide examples, the ability of the pan amyloid-reactive fusion peptides to bind to all or a subset of amyloid deposit types allows administration of a single antibody to be effective against multiple amyloid deposit types. In other words, while the amyloid-reactive antibody may only bind one or a few amyloid types, use of the amyloid-reactive fusion peptides (that include the amyloid-reactive antibody epitope) can pre-target the amyloid-reactive antibody to multiple amyloid types. Use of the amyloid-reactive antibodies has the additional advantage of directly targeting the amyloid deposits to which the amyloid-reactive antibodies are reactive.

Without wishing to be bound by any particular theory, it is believed that binding of the amyloid-reactive antibodies to the amyloid deposit—via binding to the amyloid-reactive peptides or fusion peptides as described herein—results in clearance of the amyloid deposits, for example, through processes such as opsonization and phagocytosis. In other words, it is believed that localization of antibodies to amyloid deposits triggers an immune response in which opsonization and/or phagocytosis remove all or part of the targeted amyloid deposits. By initiating and facilitating clearance of amyloid deposits in a subject suffering from amyloidosis, the amyloid-reactive peptides, amyloid-reactive fusion peptides, antibodies, and methods described herein may be used to treat the subject. Further, by using known amyloid-reactive antibodies to bind to the amyloid-reactive fusion peptides, the methods and compositions described herein allow existing antibodies, including non-amyloid-specific antibodies, to be adapted for use in the treatment of amyloidosis.

SUMMARY OF TERMS

Unless otherwise noted, technical terms are used according to conventional usage. Definitions of common terms in molecular biology may be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710) and other similar references. As used herein, the singular forms "a," "an," and "the," refer to both the singular as well as plural, unless the context clearly indicates otherwise. The abbreviation, "e.g." is derived from the Latin exempli gratia, and is used herein to indicate a non-limiting example. Thus, the abbreviation "e.g." is synonymous with the term "for example." As used herein, the term "comprises" means "includes." All publications, patent applications, patents, and other references mentioned herein are expressly incorporated herein by reference in their entirety.

It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. In case of conflict, the present specification, including explanations of terms, will control. In addition, the materials, methods, and examples are illustrative only and not intended to be limiting. To facilitate review of the various example embodiments of this disclosure, the explanations of specific terms are provided below.

An "amyloid-reactive peptide" is a peptide that binds to amyloid deposits, such as any of the amyloids identified in Table 1. The amyloid-reactive peptide may also be a "pan" amyloid binding peptide, meaning that the amyloid-reactive peptide binds to multiple amyloid types. An "amyloid-reactive fusion peptide," for example, is amyloid-reactive peptide that is fused to another peptide, such as an epitope, resulting in a fusion peptide.

"Administration" or "administering" refers to the introduction of a composition into a subject by a chosen route. For example, if the chosen route is intravenous, the composition is administered by introducing the composition into a vein of the subject. In some examples, the peptides and antibodies disclosed herein are administered to a subject.

"Animal" refers to living multi-cellular vertebrate organisms, a category that includes, for example, mammals and birds.

"Antibody" refers to single chain, two-chain, and multi-chain proteins and glycoproteins belonging to the classes of polyclonal, monoclonal, chimeric and hetero immunoglobulins (monoclonal antibodies being preferred); it also includes synthetic and genetically engineered variants of these immunoglobulins. An "antibody fragment" includes Fab, Fab', F(ab')2, and Fv fragments, as well as any portion of an antibody having specificity toward a desired target epitope or epitopes. A "monoclonal antibody" is an antibody produced by a single clone of B-lymphocytes. Monoclonal antibodies are produced by methods known to those of skill in the art, for instance by making hybrid antibody-forming cells from a fusion of myeloma cells with immune spleen cells.

"Epitope" refers to a site on an antigen recognized by an antibody, as determined by the specificity of the antibody amino acid sequence. Epitopes are also called antigenic determinants. For example, the epitope may be portion of a recombinant protein that is recognized by the particular antibody. Further, the epitope may be a conformational epitope and linear epitope.

"Chimeric antibody" refers to an antibody that includes sequences derived from two different antibodies, which typically are of different species. Most typically, chimeric antibodies include human and murine antibody fragments, generally human constant and murine variable regions.

"Humanized antibody" refers to an antibody derived from a non-human antibody, typically murine, and a human antibody which retains or substantially retains the antigen-binding properties of the parent antibody but which is less immunogenic in humans.

"Complementarity Determining Region," or CDR refers to amino acid sequences that together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. By definition, the CDRs of the light chain are bounded by the residues at positions 24 and 34 (L-CDR1), 50 and 56 (L-CDR2), 89 and 97 (L-CDR3); the CDRs of the heavy chain are bounded by the residues at positions 31 and 35b (H-CDR1), 50 and 65 (H-CDR2), 95 and 102 (H-CDR3), using the numbering convention delineated by Kabat et al., (1991) *Sequences of Proteins of Immunological Interest,* 5th Edition, Department of Health and Human Services, Public Health Service, National Institutes of Health, Bethesda (NIH Publication No. 91-3242).

"Framework region" refers to amino acid sequences interposed between CDRs. These portions of the antibody serve to hold the CDRs in an appropriate orientation for antigen binding.

"Specificity Determining Residue," or SDR refers to amino acid residues of an immunoglobulin that are directly involved in antigen contact.

"Constant region" refers to the portion of the antibody molecule that confers effector functions. In the present invention, the variant antibodies include constant regions derived from human immunoglobulins. The heavy chain constant region can be selected from any of five isotypes: alpha, delta, epsilon, gamma or mu. Heavy chains of various subclasses (such as the IgG subclass of heavy chains) are responsible for different effector functions. Thus, by choosing the desired heavy chain constant region, humanized antibodies with the desired effector function can be produced. The light chain constant region can be of the kappa or lambda type, preferably the kappa type.

"Amino acid" or "amino acid residue" refers to any naturally occurring amino acid, any non-naturally occurring amino acid, any modified including derivatized amino acid, or any amino acid mimetic known in the art. The amino acid may be referred by both their common three-letter abbreviation and single letter abbreviation.

The terms "amyloids," "amyloid deposits," or "amyloid fibrils" refer to insoluble fibrous protein aggregates sharing specific structural traits. Abnormal accumulation of amyloids in organs may lead to amyloidosis. Although they are diverse in their occurrence, all amyloids have common morphologic properties such as stain with specific dyes such as Congo red, and have a characteristic red-green birefringent appearance in polarized light after staining. Amyloids also share common ultrastructural features and common x-ray diffraction and infrared spectra.

"Amyloidosis" refers to a pathological condition or disease characterized by the presence of amyloids, such as the presence of amyloid deposits.

The terms "clear" or "clearance" refer to reducing or removing by a measurable degree. For example, the clearance of an amyloid deposit as described herein relates to reducing or removing the deposit to a measurable or discernable degree.

"Carrier" refers to conventional pharmaceutically acceptable carriers. *Remington's Pharmaceutical Sciences,* by E. W. Martin, Mack Publishing Co., Easton, Pa., 19$^{th}$ Edition (1995), for example, describes compositions and formulations suitable for pharmaceutical delivery of the peptides disclosed herein. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Example carriers include excipients or stabilizers that are nontoxic to the cell, tissue, mammal, or subject being exposed thereto at the dosages and concentrations employed. Often the pharmaceutically acceptable carrier is an aqueous pH buffered solution. Examples of pharmaceutically acceptable carriers also include, without limitation, buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween®, polyethylene glycol (PEG), and Pluronics®. As used herein, a chimeric antibody refers to an antibody which includes sequences derived from two different antibodies, which typically are of different species. Most typically, chimeric antibodies include human and murine antibody fragments, generally human constant and murine variable regions.

"DNA" (deoxyribonucleic acid) refers to a long chain polymer which constitutes the genetic material of most living organisms (some viruses have genes composed of ribonucleic acid (RNA)). The repeating units in DNA polymers are four different nucleotides, each of which contains one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequence of three nucleotides in the mRNA that is transcribed from the DNA.

"Effective amount" or "suitable amount" or "therapeutically effective amount" refers to an amount of a substance sufficient to effect the beneficial or desired clinical or biochemical results. An effective amount can be administered one or more times. For example, an effective amount of a peptide or fusion peptide as described herein is an amount that is sufficient to bind to and allow detection of the amyloids. A peptide or fusion peptide as described herein may be effective, for example, when parenterally administered in amounts above about 1 µg per kg of body weight to about 30 mg/kg. A therapeutically effective amount of an antibody described herein is the amount that is sufficient to bind the peptide or fusion peptide as described herein.

"Immune cell" refers to any cell involved in a host defense mechanism. These can include, for example, T cells, B cells, natural killer cells, neutrophils, mast cells, macrophages, antigen-presenting cells, basophils, eosinophils, and neutrophils. An "immune response" is a response of a cell of the immune system, such as a macrophage, neutrophil, a B cell, or a T cell, to a stimulus.

"Label" refers to a detectable compound or composition that is conjugated directly or indirectly to another molecule to facilitate detection of that molecule. Specific, non-limiting examples of labels include fluorescent tags, chemiluminescent tags, haptens, enzymatic linkages, and radioactive isotopes.

A "mammal" refers to any animal classified as a mammal, including humans, domestic and farm animals, and zoo, sports, or pet animals, such as dogs, cats, cattle, horses, sheep, pigs, and so on. The mammal may be a human.

"Operably linked" refers to a first nucleic acid sequence that is connected to a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

"Opsonize" or "opsonization," as used herein, refer to immunoglobulin-based recognition of a target as "foreign" by the host's cellular immune system. For example, the binding of an immunoglobulin, such as the antibodies described herein, to an amyloid-deposit via an amyloid-reactive peptide or fusion peptide enhances the phagocytization of amyloid fibrils.

"Peptide" refers to any peptide or peptidomimetic structure comprising or consisting of two or more amino acids, including chemical modifications and derivatives of amino acids. For example, the peptide may be modified to include epitope capable of binding an antibody. In certain example embodiments, a peptide may be an amyloid-reactive peptide, meaning that the peptide reacts with an amyloid by binding to the amyloid.

"Polypeptide" refers to a polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein is intended to encompass any amino acid sequence and include modified sequences such as glycoproteins. The term "polypeptide" is specifically intended to cover naturally occurring proteins, as well as those that are recombinantly or synthetically produced. In some examples, a polypeptide is one or more of the peptides disclosed herein. As used herein, the terms "fusion protein" or "fusion polypeptide" or "fusion peptide" refer to a non-naturally occurring protein having the portion of the peptide and another portion that has been added to the protein. For example, an antibody epitope may be covalently bound to the protein to form a fusion protein.

"Protein" refers to a biological molecule encoded by a gene and comprised of amino acids.

"Pharmaceutical agent" refers to a chemical compound or composition capable of inducing a desired therapeutic or prophylactic effect when properly administered to a subject or a cell. For example, a pharmaceutical agent may include a peptide as described herein and an antibody described herein, the administration of which result in clearance of an amyloid deposit.

"Purified" or "isolated" molecule refers to biological or synthetic molecules that are removed from their natural environment and are isolated or separated and are free from other components with which they are naturally associated. The term "purified" does not require absolute purity; rather, it is intended as a relative term. Thus, for example, a purified or "substantially pure" protein preparation is one in which the protein referred to is more pure than the protein in its natural environment within a cell or within a production reaction chamber (as appropriate).

"Recombinant" nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

The term "specifically binds" refers to a non-random binding reaction between two molecules, for example between a peptide of the present invention and an amyloid. The term "specifically binds" may be used interchangeably with "selectively targets" or "selectively associates."

The term "selectively targets" or "selectively associates" with reference to amyloids, refers to, for example, the selective localization or binding to the amyloid. For example, an amyloid-reactive peptide or fusion peptide as described herein pre-targets an amyloid deposit by binding to the deposit. An antibody binding the peptide or fusion peptide then targets the amyloid, such as for opsinization, as described herein.

"Sequence identity" refers to the similarity between two nucleic acid sequences, or two amino acid sequences, and is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith & Waterman *Adv. Appl. Math.* 2: 482, 1981; Needleman & Wunsch *J. Mol. Biol.* 48: 443, 1970; Pearson & Lipman *Proc. Natl. Acad. Sci. USA* 85: 2444, 1988; Higgins & Sharp *Gene* 73: 237-244, 1988; Higgins & Sharp *CABIOS* 5: 151-153, 1989; Corpet et al. Nuc. Acids Res. 16, 10881-90, 1988; Huang et al. *Computer Appls. In the Biosciences* 8, 155-65, 1992; and Pearson et al. *Meth. Mol. Bio.* 24, 307-31, 1994. Altschul et al. (*J. Mol. Biol.* 215:403-410, 1990), presents a detailed consideration of sequence alignment methods and homology calculations.

The NCBI Basic Local Alignment Search Tool (BLAST) (Altschul et al. *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

A "subject" refers to a vertebrate. The vertebrate may be a mammal, for example, a human. The subject may be a human patient. A subject may be a patient suffering from or suspected of suffering from a disease or condition and may be in need of treatment or diagnosis or may be in need of monitoring for the progression of the disease or condition. The patient may also be in on a treatment therapy that needs to be monitored for efficacy. In some example embodiments, a subject includes a subject suffering from amyloidosis, such as Alzheimer's, Huntington's or prion diseases, or peripheral amyloidosis such as seen in patients with light chain (AL) amyloidosis and type 2 diabetes.

The terms "treating" or "treatment" refer to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

A "vector" refers to a nucleic acid molecule as introduced into a host cell, thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses. The term vector includes plasmids, linear nucleic acid molecules, and as described throughout adenovirus vectors and adenoviruses.

Amyloid-Reactive Peptides

In certain example embodiments, provided are amyloid-reactive peptides and amyloid-reactive fusion peptides that specifically bind amyloids and thus are useful in the various methods and pharmaceutical compositions described herein. As "amyloid-reactive" peptides, the peptides bind to and interact with amyloids and/or components of amyloid deposits. For example, the amyloid-reactive peptides and fusion peptides bind one or more components of the fibrils that make up an amyloid deposit. The amyloid type can be any amyloid.

Additionally or alternatively, the amyloid-reactive peptides and fusion peptides may bind one or more other amyloid deposit components, such as heparan sulfate proteoglycans and glycosaminoglycans (GAGs). In certain example embodiments, the amyloid-reactive peptides and fusion peptides are synthetic pan amyloid-reactive peptides that bind to multiple amyloid deposit types. For example, the amyloid-reactive peptides and fusion peptides may bind any one of AA, AL, AH, ATTR, Aβ2M, ALect2, Wild type TTR, AApoAI, AApoAII, AGel, ALys, ALect2, Afib, ACys, ACal, AMedin, AIAPP, APro, AIns, APrP, Aβ, or combinations thereof or other amyloids. In certain example embodiments, the amyloid-reactive peptide is a peptide disclosed in U.S. Pat. No. 8,808,666, which is expressly incorporated herein by reference in its entirety.

Additionally or alternatively, the amyloid-reactive peptides and fusion peptides may include a functional fragment that binds one or more amyloid types. Such fragments, for example, maintain the amyloid binding characteristics of the parent amyloid-reactive peptide. In certain example embodiments, one or more of the amyloid-reactive peptides and fusion peptides described herein bind to multiple amyloid deposit types. For example, the fragment of the amyloid-reactive peptide may be a pan amyloid-reactive peptide fragment that binds to multiple amyloid types.

The amyloid-reactive peptides include, for example, from about 3 to about 55 amino acids. For example, the peptides may include about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 amino acids. In certain example embodiments, the peptides may have a molecular weight of between about 200 Da to about 6 kDa. The molecular weight of the peptides may be about 300 Da, 400 Da, 500 Da, 1 Kda, 2 kDa, 3 kDa, 4 kDa, or 5 kDa, for example.

In certain example embodiments, the amino acids forming all or a part of the amyloid-reactive peptides and fusion peptides described herein may be stereoisomers. Additionally or alternatively, the amino acids forming all or a part of the peptides described herein may be modifications of naturally occurring amino acids, non-naturally occurring amino acids, post-translationally modified amino acids, enzymatically synthesized amino acids, derivatized amino acids, constructs or structures designed to mimic amino acids, and the like. The amino acids forming the peptides of the present invention may be one or more of the 20 common amino acids found in naturally occurring proteins, or one or more of the modified and unusual amino acids. In certain example embodiments, the amino acids may be D- or L-amino acids.

In certain example embodiments, the peptides may also include one or more modified amino acids. The modified amino acid may be a derivatized amino acid or a modified and unusual amino acid. Examples of modified and unusual amino acids include but are not limited to, 2-Aminoadipic acid (Aad), 3-Aminoadipic acid (Baad), β-Amino-propionic acid (Bala, β-alanine), 2-Aminobutyric acid (Abu, piperidinic acid), 4-Aminobutyric acid (4Abu), 6-Aminocaproic acid (Acp), 2-Aminoheptanoic acid (Ahe), 2-Aminoisobutyric acid (Aib), 3-Aminoisobutyric acid (Baib), 2-Aminopimelic acid (Apm), 2,4-Diaminobutyric acid (Dbu), Desmosine (Des), 2,2'-Diaminopimelic acid (Dpm), 2,3-Diaminopropionic acid (Dpr), N-Ethylglycine (EtGly), N-Ethylasparagine (EtAsn), Hydroxylysine (Hyl), allo-Hydroxylysine (AHyl), 3-Hydroxyproline (3Hyp), 4-Hydroxyproline (4Hyp), Isodesmosine (Ide), allo-Isoleucine (AIle), N-Methylglycine (MeGly, sarcosine), N-Methylisoleucine (MeIle), 6-N-Methyllysine (MeLys), N-Methylvaline (MeVal), Norvaline (Nva), Norleucine (Nle), and Ornithine (Orn).

Other examples of modified and unusual amino acids are described generally in Synthetic Peptides: A User's Guide, Second Edition, April 2002, Edited Gregory A. Grant, Oxford University Press; Hruby V J, Al-obeidi F and Kazmierski W: *Biochem J* 268:249-262, 1990; and Toniolo C: *Int J Peptide Protein Res* 35:287-300, 1990; the teachings of all of which are expressly incorporated herein by reference.

In certain example embodiments, the amino acid sequence of the peptides is sequential, without any modified and unusual amino acids interrupting the sequence of D- or L-amino acids. In other embodiments, the sequence may include one or more modified and unusual amino acids as noted above. For example, the sequence of the peptides may be interrupted by one or more modified and unusual amino acids. Accordingly, provided are pseudopeptides and peptidomimetics, including structures that have a non-peptidic backbone that specifically bind amyloids. In certain example embodiments, the amyloid-reactive peptides and fusion peptides include dimers or multimers of peptides that have enhanced affinity for amyloids as compared to their monomers.

In certain example embodiments, the amyloid-reactive peptides and fusion peptides may be rich in positively charged amino acids. For example, the amyloid-reactive peptides and fusion peptides may include at least about 15% positively charged amino acids such as arginine or lysine. In other example embodiments, the amyloid-reactive peptides and fusion peptides may

TABLE 2

Example Amyloid-Reactive Peptide Sequences

| PEPTIDE | PRIMARY SEQUENCE: | SEQ ID NO |
|---|---|---|
| P5 | KAQKA QAKQA KQAQK AQKAQ AKQAK Q | SEQ ID NO: 1 |
| p5R | RAQRA QARQA RQAQR AQRAQ ARQAR Q | SEQ ID NO: 2 |
| p5G | GAQGA QAGQA GQAQG AQGAQ AGQAG Q | SEQ ID NO: 3 |
| p8 | KAKAK AKAKA KAKAK | SEQ ID NO: 4 |
| P9 | KAQAK AQAKA QAKQA AKAQA KAQAK AQAK | SEQ ID NO: 5 |
| p19 | KAQQA QAKQA QQAQK AQQAQ AKQAQ Q | SEQ ID NO: 6 |
| p20 | QAQKA QAQQA KQAQQ AQKAQ AQQAK Q | SEQ ID NO: 7 |
| p31 | KAQKA QAKQA KQAQK AQKAQ AKQAK Q | SEQ ID NO: 8 |
| p37 | KTVKT VTKVT KVTVK TVKTV TKVTK V | SEQ ID NO: 9 |
| p39 | [KAQKA QAKQA KQAQK AQKAQ AKQAK Q]$_D$ | SEQ ID NO: 10 |
| p42 | V[Y]$_D$KVK TKVKT KVKTK VKT | SEQ ID NO: 11 |
| p43 | [AQA]$_D$YS KAQKA QAKQA KQAQK AQKAQ AKQAK Q | SEQ ID NO: 12 |
| p44 | [AQA]$_D$YA RAQRA QARQA RQAQR AQRAQ ARQAR Q | SEQ ID NO: 13 |
| p48 | AQA[YS KAQKA QAKQA KQAQK AQKAQ AKQAK Q]$_D$ | SEQ ID NO: 14 |
| p50 | AQAYS KAQKA QAKQA KQAQK AQKAQ AKQAK Q | SEQ ID NO: 15 |

TABLE 2-continued

Example Amyloid-Reactive Peptide Sequences

| PEPTIDE | PRIMARY SEQUENCE: | SEQ ID NO |
|---|---|---|
| p58 | AQA[Y]$_D$S KAQKA QAKQA KQAQK AQKAQ AKQAK Q | SEQ ID NO: 16 |
| p5 + 14 | KAQKA QAKQA KQAQK AQKAQ AKQAK QAQKA QKAQA KQAKQ | SEQ ID NO: 17 |

Where D = the "D form" enantiomer.

include from about 15% to about 50%, about 20% to about 45%, about 25% to about 40%, or about 30% to about 35% positively charged amino acids, such as arginine or lysine.

In certain example embodiments, particular amyloid-reactive peptides and fusion peptides include one or more of the amino acid sequences set forth as SEQ ID NOS:1-17, as shown in Table 2 (above).

In certain example embodiments, the amyloid-reactive peptides and fusion peptides include a peptides that are at least 60%, at least 65%, at least 70%, at least 75%, at least 80%, at least 85%, at least 90%, or at least 95% identical to one or more of the sequences set forth as SEQ ID NOS:1-17. In certain example embodiments, the amyloid-reactive peptides and fusion peptides may include a functional leader sequence fused to the N-terminus or C-terminus of the peptide. For example, one or more of the sequences shown in Table 2 or Table 6 may include GGGYS- (SEQ ID NO:24) or CGGYS- (SEQ ID NO:25) sequences that are fused to the N-terminus end of the peptide. The leader sequence, for example, may be a cell-penetrating sequence.

In certain example embodiments, the amyloid-reactive peptides are modified to include an epitope to a known antibody. That is, an epitope of a known antibody or functional fragment thereof is attached to one or more of the amyloid-reactive peptides described herein to form an amyloid-reactive fusion peptide. In accordance with the methods described herein, when the amyloid-reactive fusion peptide including the epitope comes in to contact with the antibody to which the epitope is reactive, the antibody binds the epitope (and hence indirectly binds the amyloid-reactive peptide via the epitope). As such, the antibody epitope can be any antibody epitope, for example, that results in binding of the epitope to the antibody to which the epitope is reactive. In certain example embodiments, any of the amyloid-reactive peptides identified in Table 2 (SEQ ID NOS: 1-17) may be fused to such an epitope to form an amyloid-reactive fusion peptide.

In certain example embodiments, the epitope of the amyloid-reactive fusion peptide is added to the extreme N- or C-terminus of the amyloid-reactive peptide, since the ends of the proteins are more likely to be accessible to the antibody and since the addition of the epitope to the end is less likely to affect the function of the protein. Additionally or alternatively, addition of the epitope to an internal site may be used, such as when the ends of the fusion peptide are important for the peptide's function or when processing is taking place at these ends. In certain example embodiments, the amyloid-reactive fusion peptide may include a linker sequence to fuse the epitope to the amyloid-reactive peptide. The linker sequence may be any sequence known in the art that, when used to form the fusion peptide, does not interfere with the function of the peptide. In certain example embodiments, the linker has the following sequence: "SVTVVT" (SEQ ID NO: 21).

In certain example embodiments, the epitope of the fusion peptide is an epitope of an antibody that binds to amyloids (i.e., the epitope is an epitope of an amyloid-reactive antibody). For example, the epitope is an epitope of an antibody that binds AA, AL, AH, ATTR, Aβ2M, ALect2, Wild type, TTR, AApoAI, AApoAII, AGel, ALys, ALect2, Afib, ACys, ACal, AMedin, AIAPP, APro, AIns, APrP, Aβ amyloids, or any other amyloid. In such embodiments, the amyloid-reactive antibodies may bind both (1) the amyloid-reactive peptides including the epitope as well as (2) the amyloid type(s) to which the antibody is directed, as described herein. In certain example embodiments, the epitope may be a His-tag, Myc-tag, or other tag known in the art.

In certain example embodiments, the epitope is one that binds to the 11-1F4 antibody or functional fragments thereof, the 11-1F4 antibody being described in U.S. Pat. No. 8,105,594 and in O'Nuallain et al., *Biochemistry*, 2007, 46 (5), 1240-1247 (both of which are expressly incorporated herein by reference in their entirety). For example, the Len(1-16) peptide, which is a known binding motif of the amyloid-reactive monoclonal antibody 11-1F4, may be used as a basis for the epitope. In such example embodiments, the monoclonal antibody 11-1F4 binds to the Len(1-16)-based peptide-epitope ("peptope") fusion via the epitope amino acid sequence rather than to the amyloid-reactive peptide directly, as described herein. For example, any of the amyloid-reactive peptides in Table 2 may be fused to the Len(1-16)-based sequence "DIVMTQSPDS LAVSLG" (SEQ ID NO:22) to form an amyloid-reactive fusion peptide as described herein. As an example, the amyloid-reactive fusion peptide may include the amyloid-reactive peptide of SEQ ID NO:17 (p5+14) fused to the Len(1-16)-based sequence set forth in SEQ ID NO:22.

In certain example embodiments, an amyloid-reactive peptide is fused to an 11 1F4 antibody epitope having the following 12-mer epitope sequence: "KHYAAFPENLLI" (SEQ ID NO:23). In certain example embodiments, the KHYAAFPENLLI epitope sequence (SEQ ID NO: 23) is fused to any of the amyloid-reactive peptides in Table 2 to form the amyloid-reactive fusion peptide. As an example, the amyloid-reactive peptide having the sequence set forth as SEQ ID NO:17 (p5+14) is fused to the KHYAAFPENLLI sequence (SEQ ID NO: 23) to form an amyloid-reactive fusion peptide. In such example embodiments, the 12-mer-epitope sequence may be indirectly fused to the peptide, such as to the C-terminus of the peptide, via a linker sequence as described herein. For example, the linker sequence may be SVTVVT (SEQ ID NO: 21). In certain example embodiments, an amyloid-reactive fusion peptide including the 11 1F4 antibody 12-mer epitope fused to the p5+14 peptide has the following amino acid sequence (SEQ ID NO: 18 or "p66"), with the underlined portion being an 11-1F4 reactive 12-mer epitope and SVTVVT (SEQ ID NO: 21) being the linker sequence:

```
                                              (SEQ ID NO: 18)
    KAQKA QAKQA KQAQK AQKAQ AKQAK QAQKA QKAQA
    KQAKQ SVTVVT KHYAAFPENLLI
```

In certain example embodiments, the amyloid-reactive fusion peptide has the following sequence (SEQ ID NO:19), where X is an amino acid of a linker sequence and the underlined portion is the 11-1F4 12-mer epitope:

```
    KAQKA QAKQA KQAQK AQKAQ AKQAK QAQKA QKAQA
    KQAKQ-XXXXXX-KHYAAFPENLLI
```

In certain example embodiments, an amyloid-reactive fusion peptide including the 11-1F4 antibody 12-mer epitope has the following amino acid sequence (SEQ ID NO:20), with the underlined portion being the 11-1F4 reactive epitope, X being an amino acid of a linker sequence, and "n" being the number of linker amino acids:

```
    KAQKA QAKQA KQAQK AQKAQ AKQAK QAQKA QKAQA
    KQAKQ-[X]_n-KHYAAFPENLLI
```

For example, "n" may equal any number of amino acids, so long as the function of the amyloid-reactive peptide and the epitope is preserved. For example, "n" may equal about 1, 2, 3, 4, 5, 6, 7, 8, 9, 10, 11, 12, 13, 14, 15, 16, 17, 18, 19, 20 amino acids.

In certain example embodiments, the amyloid-reactive fusion peptide including a 11-1F4 antibody 12-mer epitope is at least 60%, at least 65%, at least 70%, at least 75%, at least 80%, at least 85%, at least 90%, or at least 95% identical to any of the sequences set forth as SEQ ID NOS: 18-20.

In certain example embodiments, the epitope may include an epitope or functional fragment thereof of monoclonal antibodies 2A4, 7D8, and 8G9. These antibodies, for example, are amyloid-reactive antibodies that bind to specific amyloid fibrils. See J. S. Wall, et al., AL Amyloid Imaging and Therapy with a Monoclonal Antibody to a Cryptic Epitope on Amyloid Fibrils, *PLoS ONE* 7(12): e52686 (2012); J. S. Wall et al., Generation and Characterization of anti-AA Amyloid-Specific Monoclonal Antibodies; Frontiers of Immunology doi:10.3389/fimmu.2011.00032 (2011) (both of which are expressly incorporated herein by reference in their entirety). As such, epitopes or functional fragments thereof to these antibodies, for example, may be fused to the amyloid-reactive peptides described herein to create fusion peptides having epitopes to one or more of the 2A4, 7D8, or 8G9 antibodies. Hence, in certain example embodiments, the epitope described herein includes a 2A4, 7D8, or 8G9 antibody-binding motif. With the epitope or functional fragment thereof of antibodies 2A4, 7D8, or 8G9, such fusion peptides can target one or more of the 2A4, 7D8, or 8G9 antibodies to a variety of amyloid types for clearance as described herein.

In certain example embodiments, the amyloid-reactive peptide is fused to a 4-mer peptide sequence having the epitope sequence HEDT (SEQ ID NO: 52). That is, the HEDT epitope sequence (SEQ ID NO: 52) can be fused to any of the amyloid-reactive peptides in Table 2 to form the amyloid-reactive fusion peptide. For example, the amyloid-reactive peptide having the sequence set forth as SEQ ID NO:1 (or p5) can be fused to the HEDT epitope (SEQ ID NO: 52) to form an amyloid-reactive fusion peptide. In another example, the amyloid-reactive peptide having the sequence set forth as SEQ ID NO:11 (or p42), with or without the D form enantiomer, can be combined with the HEDT epitope (SEQ ID NO: 52). In such example embodiments, the HEDT 4-mer epitope sequence (SEQ ID NO: 52) may be indirectly fused to the peptide, such as to the C-terminus of the peptide, via a linker sequence as described herein. For example, the linker sequence may be the amino acid sequence QAQ, GGG, GPG, or VTV. When the 4-mer is fused to SEQ ID NO: 1, for example, the sequence may be any of the amino sequences set forth as SEQ ID NOs. 26-29 (see Table 6, below).

In certain example embodiments, the amyloid-reactive fusion peptide including the 4-mer HEDT epitope (SEQ ID NO: 52) fused to the p5 (SEQ ID NO:1) peptide has the following amino acid sequence (SEQ ID NO: 30), with the underlined portion being HEDT (SEQ ID NO: 52), X being an amino acid of a linker sequence, and "n" being the number of linker amino acids:

KAQKA QAKQA KQAQK AQKAQ AKQAK QAQKA QKAQA
KQAKQ-$[X]_n$-HEDT

For example, "n" may equal any number of amino acids, so long as the function of the amyloid-reactive peptide and the epitope is preserved. For example, "n" may equal about 1, 2, 3, 4, 5, 6, 7, 8, 9, 10, 11, 12, 13, 14, 15, 16, 17, 18, 19, 20 amino acids.

In certain example embodiments, the amyloid-reactive fusion peptide including a 4-mer HEDT (SEQ ID NO: 52) epitope is at least 60%, at least 65%, at least 70%, at least 75%, at least 80%, at least 85%, at least 90%, or at least 95% identical to any of the sequences set forth as SEQ ID NOS: 26-29.

In certain example embodiments, such as when ATTR-amyloid targeting is the primary goal, then the peptope may include the sequence p5+14 fused to the HEDT epitope (SEQ ID NO: 52) as described herein may be useful. The p5+14 (SEQ ID NO: 17) exhibits pan-amyloid reactivity but has demonstrated greater affinity for human ATTR amyloid extracts. A peptope based on the p5+14 core would thus allow pre-targeting of mAbs 2A4, 7D8, or 8G9 optimally to ATTR but would also potentially enhance the utility of the mAbs 2A4, 7D8, or 8G9 to patients with all visceral amyloid including patients with cerebral amyloid angiopathy. For example, the fusion peptide may comprise the following sequence (SEQ ID NO: 31), with the underlined portion being a linker sequence: KAQKA QAKQA KQAQK AQKAQ AKQAK QAQKA QKAQA KQAKQ-QAQ-HEDT.

In certain example embodiments, the amyloid-reactive peptide is fused to a variable 4-mer peptide sequence having the amino acid epitope sequence $X_1$-ED-$X_2$ (SEQ ID NO: 53), where $X_1$ and $X_2$ are any amino acid. That is, the $X_1$-ED-$X_2$ epitope sequence (SEQ ID NO: 53) can be fused to any of the amyloid-reactive peptides in Table 2 to form the amyloid-reactive fusion peptide as described herein. For example, the amyloid-reactive peptide having the sequence set forth as SEQ ID NO:1 (or p5) or SEQ ID NO: 11 can be fused to the $X_1$-ED-$X_2$ epitope (SEQ ID NO: 53) to form an amyloid-reactive fusion peptide. In such example embodiments, the $X_1$-ED-$X_2$ 4-mer epitope sequence (SEQ ID NO: 53) may be indirectly fused to the peptide, such as to the C-terminus of the peptide, via a linker sequence as described herein. For example, the linker sequence may be the amino acid sequence QAQ, GGG, GPG, or VTV. When the amyloid reactive peptide set forth in SEQ ID NO: 1 is fused to the $X_1$-ED-$X_2$ 4-mer epitope (SEQ ID NO: 53) via a QAQ linker (underlined), for example, the sequence of the fusion peptide is (SEQ ID NO: 32):

KAQKA QAKQA KQAQK AQKAQ AKQAK Q-QAQ-$X_1$-ED-$X_2$ where $X_1$ and $X_2$ are any amino acid. Additionally or alternatively, the fusion peptide may comprise the following sequence (SEQ ID NO: 33), with the underlined portion being a linker sequence:

KAQKA QAKQA KQAQK AQKAQ AKQAK QAQKA QKAQA KQAKQ-QAQ-$X_1$-ED-$X_2$ where $X_1$ and $X_2$ are any amino acid. In certain example embodiments, the amyloid reactive fusion peptide that includes the 4-mer having the $X_1$-ED-$X_2$ epitope (SEQ ID NO: 53) is 95% identical to SEQ ID NOS: 32 or 33, with the $X_1$-ED-$X_2$ epitope (SEQ ID NO: 53) being conserved. Exemplary $X_1$-ED-$X_2$ epitopes ("$X_1$-ED-$X_2$" disclosed as SEQ ID NO: 53), which are found in immunoglobulin light chains are provided in Table 3.

TABLE 3

Exemplary $X_1$-ED-$X_2$ SAA and Immunoglobulin Light Chain Epitopes ("$X_1$-ED-$X_2$" disclosed as SEQ ID NO: 53)

| SAA or immunoglobulin light chain | $X_1$-ED-$X_2$ Sequence | GenBank Accession No. |
|---|---|---|
| SAA1 | AEDS, (SEQ ID NO: 34) | |
| SAA2 | AEDS, (SEQ ID NO: 34) | |
| SAA3 | AEDS, (SEQ ID NO: 34) | |
| SAA4 | AEDS, (SEQ ID NO: 34) | |
| anti-Sm immunoglobulin kappa light chain V region; monoclonal antibody 4B4 kappa chain | AEDV, (SEQ ID NO: 35) | AAB26897 |
| immunoglobulin variable region used by the ITC52 kappa light chain (subgroup V kappa II | PEDS, (SEQ ID NO: 36) | AAC61608 |
| immunoglobulin variable region used by the ITC48 kappa light chain (subgroup V kappa IV) | AEDV, (SEQ ID NO: 35) | AAC61606 |
| anti-RhD monoclonal T125 kappa light chain precursor | SEDF, (SEQ ID NO: 37) | AAW82027 |
| immunoglobulin kappa light chain precursor | AEDV, (SEQ ID NO: 35) | CAA45496 |
| immunoglobulin kappa light chain variable region | PEDF, (SEQ ID NO: 38) | AAT44350 |
| immunoglobulin kappa light chain variable region | PEDF, (SEQ ID NO: 38) | AAT44349 |
| immunoglobulin kappa light chain variable region | PEDF, (SEQ ID NO: 38) | AAT44348 |
| immunoglobulin kappa light chain | PEDF, (SEQ ID NO: 38) | CAA09185 |
| immunoglobulin kappa light chain | SEDF, (SEQ ID NO: 37) | CAA09181 |
| immunoglobulin kappa light chain variable region | SEDF, (SEQ ID NO: 37) | AAU14891 |
| anti-rabies SOJA immunoglobulin kappa light chain | PEDF, (SEQ ID NO: 38) | AAO17825 |
| anti-streptococcal/anti-myosin immunoglobulin kappa light chain variable region | SEDF, (SEQ ID NO: 37) | AAB68786 |
| anti-streptococcal/anti-myosin immunoglobulin kappa light chain variable region | PEDF, (SEQ ID NO: 38) | AAB68785 |
| anti-HLA-A2/anti-HLA-A28 immunoglobulin kappa light chain variable region | PEDF, (SEQ ID NO: 38) | AAC99644 |
| immunoglobulin kappa light chain V region; anti-DNA antibody 18/2 | PEDF, (SEQ ID NO: 38) | AAB62946 |

TABLE 3-continued Exemplary $X_1$-ED-$X_2$ SAA and Immunoglobulin Light Chain Epitopes
("$X_1$-ED-$X_2$" disclosed as SEQ ID NO: 53)

| SAA or immunoglobulin light chain | $X_1$-ED-$X_2$ Sequence | GenBank Accession No. |
|---|---|---|
| immunoglobulin kappa light chain | PEDF, (SEQ ID NO: 38) | BAF75949 |
| anti-HIV-1 gp120 immunoglobulin 48d kappa light chain | PEDF, (SEQ ID NO: 38) | AAR88370 |
| immunoglobulin kappa light chain | PEDL, (SEQ ID NO: 39) | BAA97671 |
| anti-Entamoeba histolytica immunoglobulin kappa light chain | PEDF, (SEQ ID NO: 38) | BAA82105 |
| anti-Entamoeba histolytica immunoglobulin kappa light chain | TEDV, (SEQ ID NO: 40) | BAA82102 |
| immunoglobulin kappa light chain | PEDF, (SEQ ID NO: 38) | AAC41705 |
| anti-GM2 ganglioside IgM monoclonal kappa light chain variable region | AEDV, (SEQ ID NO: 35) | AAC26480 |
| anti-SARS-CoV immunoglobulin kappa light chain variable region | PEDV, (SEQ ID NO: 41) | AAT51719 |
| anti-SARS-CoV immunoglobulin kappa light chain variable region | PEDF, (SEQ ID NO: 38) | AAT51718 |
| immunoglobulin kappa light chain VLJ region | PEDF, (SEQ ID NO: 38) | BAD27502 |
| immunoglobulin kappa light chain VLJ region | SEDF, (SEQ ID NO: 37) | BAD27497 |
| anti-HIV-1 gp120 immunoglobulin 47e kappa light chain | PEDF, (SEQ ID NO: 38) | AAR88378 |
| anti-HIV-1 gp120 immunoglobulin 16c kappa light chain | PEDF, (SEQ ID NO: 38) | AAR88374 |
| anti-HIV-1 gp120 immunoglobulin 411g kappa light chain | SEDF, (SEQ ID NO: 37) | AAR88372 |
| immunoglobulin kappa light chain variable region | PEDF, (SEQ ID NO: 38) | AAF14212 |
| immunoglobulin kappa light chain variable region | PEDF, (SEQ ID NO: 38) | AAF14211 |
| immunoglobulin kappa light chain variable region | PEDF, (SEQ ID NO: 38) | AAF14210 |
| immunoglobulin kappa light chain variable region | PEDF, (SEQ ID NO: 38) | AAF14209 |
| immunoglobulin V-region kappa light chain | PEDI, (SEQ ID NO: 42) | AAR02415 |
| immunoglobulin kappa light chain | PEDF, (SEQ ID NO: 38) | AAM46647 |
| immunoglobulin kappa light chain | AEDV, (SEQ ID NO: 35) | AAM46643 |
| anti-Entamoeba histolytica immunoglobulin kappa light chain | PEDF, (SEQ ID NO: 38) | BAA82103 |
| immunoglobulin light chain kappa variable region | AEDV, (SEQ ID NO: 35) | AAL65723 |
| immunoglobulin light chain kappa variable region | PEDF, (SEQ ID NO: 38) | AAL65718 |
| immunoglobulin light chain kappa variable region | SEDF, (SEQ ID NO: 37) | AAL65717 |
| immunoglobulin light chain kappa variable region | SEDF, (SEQ ID NO: 37) | AAL65716 |

TABLE 3-continued

Exemplary $X_1$-ED-$X_2$ SAA and Immunoglobulin Light Chain Epitopes
("$X_1$-ED-$X_2$" disclosed as SEQ ID NO: 53)

| SAA or immunoglobulin light chain | $X_1$-ED-$X_2$ Sequence | GenBank Accession No. |
|---|---|---|
| immunoglobulin light chain kappa variable region | PEDF, (SEQ ID NO: 38) | AAL65714 |
| immunoglobulin light chain kappa variable region | PEDF, (SEQ ID NO: 38) | AAL65713 |
| immunoglobulin light chain kappa variable region | PEDF, (SEQ ID NO: 38) | AAL65712 |
| immunoglobulin light chain kappa variable region | PEDF, (SEQ ID NO: 38) | AAL65711 |
| immunoglobulin light chain kappa variable region | PEDF, (SEQ ID NO: 38) | AAL65710 |
| immunoglobulin light chain kappa variable region | LEDG, (SEQ ID NO: 43) PEDF, (SEQ ID NO: 38) | AAL65709 |
| immunoglobulin light chain kappa variable region | LEDG, (SEQ ID NO: 43) PEDF, (SEQ ID NO: 38) | AAL65708 |
| immunoglobulin light chain kappa variable region | PEDF, (SEQ ID NO: 38) | AAL65707 |
| immunoglobulin light chain kappa variable region | PEDF, (SEQ ID NO: 38) | AAL65706 |
| immunoglobulin light chain kappa variable region | PEDF, (SEQ ID NO: 38) | AAL65705 |
| immunoglobulin light chain kappa variable region | PEDF, (SEQ ID NO: 38) | AAL65704 |
| immunoglobulin light chain kappa variable region | PEDF, (SEQ ID NO: 38) | AAL65703 |
| immunoglobulin kappa light chain variable region | SEDF, (SEQ ID NO: 37) | AAC64146 |
| immunoglobulin kappa light chain variable region | SEDF, (SEQ ID NO: 37) | AAC64144 |
| immunoglobulin kappa light chain variable region | PEDF, (SEQ ID NO: 38) | ABI64139 |
| anti-pneumococcal capsular polysaccharide immunoglobulin kappa light chain | AEDV, (SEQ ID NO: 35) | AAL04535 |
| immunoglobulin light chain kappa variable region | AEDV, (SEQ ID NO: 35) | AAL65722 |
| immunoglobulin light chain kappa variable region | AEDV, (SEQ ID NO: 35) | AAL65720 |
| immunoglobulin light chain V-J region | PEDF, (SEQ ID NO: 38) | BAA19563 |
| immunoglobulin light chain V-J region | AEDE, (SEQ ID NO: 44) | BAA19562 |
| immunoglobulin light chain V-J region | AEDE, (SEQ ID NO: 44) | BAA19561 |
| immunoglobulin light chain V-J region | PEDF, (SEQ ID NO: 38) | BAA19560 |
| immunoglobulin light chain V-J region | PEDF, (SEQ ID NO: 38) | BAA19559 |
| immunoglobulin light chain V-J region | AEDV, (SEQ ID NO: 35) | BAA19558 |
| immunoglobulin light chain V-J region | PEDI, (SEQ ID NO: 42) | BAA19556 |
| immunoglobulin kappa light chain variable region | PEDF, (SEQ ID NO: 38) | AAA71907 |
| immunoglobulin kappa light chain variable region | AEDV, (SEQ ID NO: 35) | AAA71905 |

TABLE 3-continued

Exemplary $X_1$-ED-$X_2$ SAA and Immunoglobulin Light Chain Epitopes
("$X_1$-ED-$X_2$" disclosed as SEQ ID NO: 53)

| SAA or immunoglobulin light chain | $X_1$-ED-$X_2$ Sequence | GenBank Accession No. |
|---|---|---|
| immunoglobulin G1 Fab light chain variable region | AEDV, (SEQ ID NO: 35) | BAF49281 |
| immunoglobulin G1 Fab light chain variable region | PEDF, (SEQ ID NO: 38) | BAF48998 |
| immunoglobulin G1 Fab light chain variable region | PEDF, (SEQ ID NO: 38) | BAF48996 |
| kappa light chain V-region | AEDM, (SEQ ID NO: 45) | CAA37675 |
| immunogloburin G1 Fab light chain variable region | SEDF, (SEQ ID NO: 37) | BAF48994 |
| immunogloburin G1 Fab light chain variable region | PEDF, (SEQ ID NO: 38) | BAF48992 |
| Ig kappa chain precursor V-J-C region | AEDV, (SEQ ID NO: 35) | A53261 |
| Ig kappa chain precursor V region | AEDV, (SEQ ID NO: 35) | A49137 |
| Ig kappa chain precursor V-I region | SEDI, (SEQ ID NO: 46) | PN0445 |
| Ig kappa chain precursor V-III region (EVI-15) | PEDF, (SEQ ID NO: 38) | A32274 |
| Ig kappa chain V-IV region (Dep) | AEDV, (SEQ ID NO: 35) | A34153 |
| Ig kappa chain V-IV region (Fue) | AEDV, (SEQ ID NO: 35) | B34153 |
| Ig kappa chain V-II region (Pec) | AEDV, (SEQ ID NO: 35) | C34153 |
| Chain L, Igg Fab Fragment (Cd25-Binding). | AEDA, (SEQ ID NO: 47) | 1MIM_L |
| Chain H, Igg Fab Fragment (Cd25-Binding). | HEDS, (SEQ ID NO: 48) | 1MIM_H |
| Ig mu chain C region, secreted splice form | CEDD, (SEQ ID NO: 49) | MHHU |
| immunoglobulin kappa-chain VJ region | AEDV, (SEQ ID NO: 35) | AAA58923 |
| recombinant monoclonal antibody IgM 12 kappa light chain variable region | PEDF, (SEQ ID NO: 38) | ABA41551 |
| immunoglobulin light chain | AEDE, (SEQ ID NO: 44) | CAA65054 |
| immunoglobulin light chain lambda variable region | AEDE, (SEQ ID NO: 44) | AAL65769 |
| immunoglobulin light chain lambda variable region | AEDE, (SEQ ID NO: 44) | AAL65767 |
| immunoglobulin light chain lambda variable region | AEDE, (SEQ ID NO: 44) | AAL65765 |
| immunoglobulin light chain lambda variable region | TEDE, (SEQ ID NO: 50) | AAL65764 |
| immunoglobulin light chain lambda variable region | AEDE, (SEQ ID NO: 44) | AAL65763 |
| immunoglobulin light chain lambda variable region | SEDE, (SEQ ID NO: 51) | AAL65762 |
| immunoglobulin light chain lambda variable region | SEDE, (SEQ ID NO: 51) | AAL65761 |
| immunoglobulin light chain lambda variable region | SEDE, (SEQ ID NO: 51) | AAL65760 |
| immunoglobulin light chain lambda variable region | AEDE, (SEQ ID NO: 44) | AAL65759 |

TABLE 3-continued

Exemplary $X_1$-ED-$X_2$ SAA and Immunoglobulin Light Chain Epitopes
("$X_1$-ED-$X_2$" disclosed as SEQ ID NO: 53)

| SAA or immunoglobulin light chain | $X_1$-ED-$X_2$ Sequence | GenBank Accession No. |
|---|---|---|
| immunoglobulin light chain lambda variable region | AEDE, (SEQ ID NO: 44) | AAL65758 |
| immunoglobulin light chain V-J region | PEDF, (SEQ ID NO: 38) | BAA19563 |
| immunoglobulin light chain V-J region | AEDE, (SEQ ID NO: 44) | BAA19562 |
| immunoglobulin light chain V-J region | AEDE, (SEQ ID NO: 44) | BAA19561 |
| immunoglobulin light chain V-J region | PEDF, (SEQ ID NO: 38) | BAA19560 |
| immunoglobulin light chain V-J region | PEDF, (SEQ ID NO: 38) | BAA19559 |
| immunoglobulin light chain V-J region | AEDV, (SEQ ID NO: 35) | BAA19558 |
| immunoglobulin light chain V-J region | PEDI, (SEQ ID NO: 42) | BAA19556 |
| 30-lambda immunoglobulin light chain variable region | AEDE, (SEQ ID NO: 44) | AAK95335 |

The amyloid-reactive peptides and amyloid-reactive fusion peptides having an antibody epitope described herein may be made by any technique known to those of skill in the art, including chemical synthesis or recombinant means using standard molecular biological techniques. The peptides may be synthesized in solution or on a solid support in accordance with conventional techniques. Various automatic synthesizers are commercially available and can be used in accordance with known protocols. (See, for example, Stewart and Young, Solid Phase Peptide Synthesis, 2d ed. *Pierce Chemical Co.*, 1984; Tam et al., J. Am. Chem. Soc., 105: 6442, 1983; Merrifield, *Science,* 232: 341-347, 1986; and Barany and Merrifield, The Peptides, Gross and Meienhofer, eds., *Academic Press*, New York, pp. 1-284, 1979, each of which is expressly incorporated herein by reference in its entirety).

Alternatively, recombinant DNA technology may be employed wherein a nucleotide sequence which encodes an amyloid-reactive peptide as described herein is inserted into an expression vector, transformed or transfected into an appropriate host cell, cultivated under conditions suitable for expression, and isolating the peptide.

In certain example embodiments, the amyloid-reactive peptides and fusion peptides may be obtained by isolation or purification. Protein purification techniques involve, at one level, the homogenization and crude fractionation of cells, tissue, or organs to peptide and non-peptide fractions. Other protein purification techniques include, for example, precipitation with ammonium sulfate, polyethylene glycol (PEG), antibodies and the like, or by heat denaturation, followed by: centrifugation; chromatography steps such as ion exchange, gel filtration, reverse phase, hydroxylapatite and affinity chromatography; isoelectric focusing; gel electrophoresis, for example polyacrylamide gel electrophoresis; and combinations of these and other techniques.

Various chromatographic techniques include but are not limited to ion-exchange chromatography, gel exclusion chromatography, affinity chromatography, immuno-affinity chromatography, and reverse phase chromatography. A particularly efficient method of purifying peptides is fast performance liquid chromatography (FPLC) or even high performance liquid chromatography (HPLC).

The order of conducting the various purification steps may be changed, for example, or certain steps may be omitted, and still result in a suitable method for the preparation of a substantially purified peptide.

The peptides may be a part of a polypeptide or protein and may be produced by biochemical or enzymatic fragmentation of the polypeptide or protein. Accordingly, the peptides of the present invention may be (a) produced by chemical synthesis, (b) produced by recombinant DNA technology, (c) produced by biochemical or enzymatic fragmentation of larger molecules, (d) produced by methods resulting from a combination of methods a through d listed above, or (e) produced by any other means for producing peptides known to those of skill in the art.

During chemical synthesis, the amyloid-reactive peptides may be modified at the N- or C-terminus, thereby providing for improved stability and formulation, resistance to protease degradation, and the like. Examples of modifications of amino acids include pegylation, acetylation, alkylation, formylation, amidation. Moreover, various amino acids that do not naturally occur along the chain may be introduced to improve the stability of the peptides.

In certain example embodiments, also provided are nucleic acid molecules encoding the amyloid-reactive peptides and fusion peptides described herein. For example, the nucleic acid molecules include a nucleic acid sequence encoding an amino acid sequence at least 95% identical to the amino acids set forth as any one of SEQ ID NOS: 1-20, such as at least 95%, at least 96%, at least 97%, at least 98%, at least 99%, or 100% identical to the amino acids set forth as any one of SEQ ID NOS: 1-20. In the context of the compositions and methods described herein, a nucleic acid sequence that encodes at least one amyloid-reactive peptide or fusion peptide, such as described herein, is incorporated into a vector capable of expression in a host cell (for example an adenoviral vector), using established molecular biology procedures. For example nucleic acids, such as cDNAs, that encode at least one amyloid-reactive peptide or fusion peptide can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR or other in vitro amplification.

Example procedures sufficient to guide one of ordinary skill in the art through the production of vector capable of expression in a host cell that includes a polynucleotide sequence that encodes at least one amyloid-reactive peptide or fusion as described herein can be found for example in Sambrook et ah, Molecular Cloning: A Laboratory Manual, 2d ed., *Cold Spring Harbor Laboratory Press,* 1989; Sambrook et ah, Molecular Cloning: A Laboratory Manual, 3d ed., *Cold Spring Harbor Press,* 2001; Ausubel et al., Current Protocols in Molecular Biology, *Greene Publishing Associates,* 1992 (and Supplements to 2003); and Ausubel et al, Short Protocols in Molecular Biology: A Compendium of Methods from Current Protocols in Molecular Biology, 4th ed., Wiley & Sons, 1999 (each of which are hereby expressly incorporated in their entirety).

Typically, a polynucleotide sequence encoding at least one amyloid-reactive peptide or fusion peptide is operably linked to transcriptional control sequences including, for example a promoter and a polyadenylation signal. A promoter is a polynucleotide sequence recognized by the transcriptional machinery of the host cell (or introduced synthetic machinery) that is involved in the initiation of transcription. A polyadenylation signal is a polynucleotide sequence that directs the addition of a series of nucleotides on the end of the mRNA transcript for proper processing and trafficking of the transcript out of the nucleus into the cytoplasm for translation.

Exemplary promoters include viral promoters, such as cytomegalovirus immediate early gene promoter ("CMV"), herpes simplex virus thymidine kinase ("tk"), SV40 early transcription unit, polyoma, retroviruses, papilloma virus, hepatitis B virus, and human and simian immunodeficiency viruses. Other promoters are isolated from mammalian genes, including the immunoglobulin heavy chain, immunoglobulin light chain, T-cell receptor, HLA DQ α and DQ β, β-interferon, interleukin-2, interleukin-2 receptor, MHC class II, HLA-DRα, β-actin, muscle creatine kinase, prealbumin (transthyretin), elastase I, metallothionein, collagenase, albumin, fetoprotein, β-globin, c-fos, c-HA-ras, insulin, neural cell adhesion molecule (NCAM), α1-antitrypsin, H2B (TH2B) histone, type I collagen, glucose-regulated proteins (GRP94 and GRP78), rat growth hormone, human serum amyloid A (SAA), troponin I (TNI), platelet-derived growth factor, and dystrophin, dendritic cell-specific promoters, such as CD1 Ic, macrophage-specific promoters, such as CD68, Langerhans cell-specific promoters, such as Langerin, and promoters specific for keratinocytes, and epithelial cells of the skin and lung.

The promoter can be either inducible or constitutive. An inducible promoter is a promoter that is inactive or exhibits low activity except in the presence of an inducer substance. Examples of inducible promoters include, but are not limited to, MT II, MMTV, collagenase, stromelysin, SV40, murine MX gene, α-2-macroglobulin, MHC class I gene h-2kb, HSP70, proliferin, tumor necrosis factor, or thyroid stimulating hormone gene promoter.

Typically, the promoter is a constitutive promoter that results in high levels of transcription upon introduction into a host cell in the absence of additional factors. Optionally, the transcription control sequences include one or more enhancer elements, which are binding recognition sites for one or more transcription factors that increase transcription above that observed for the minimal promoter alone. It may be desirable to include a polyadenylation signal to effect proper termination and polyadenylation of the gene transcript. Example polyadenylation signals have been isolated from bovine growth hormone, SV40 and the herpes simplex virus thymidine kinase genes. Any of these or other polyadenylation signals can be utilized in the context of the adenovirus vectors described herein.

Methods of generating fusion peptides, such as the amyloid-reactive fusion peptides described herein, are also well known to those of skill in the art. Such proteins can be produced, for example, by chemical attachment using bifunctional cross-linking reagents, by de novo synthesis of the complete fusion peptide, or by attachment of a DNA sequence encoding the pre-targeting peptide to a DNA sequence encoding the second peptide or protein, followed by expression of the intact peptide or fusion peptide.

Host cells for expressing the amyloid-reactive peptides and fusion peptides described herein include prokaryotes or eukaryotes. Suitable prokaryote hosts include bacterial host cells such as *E. Coli.* Various strains of *E. coli* include but are not limited to HB101, DH5, DH10, and MC1061. Suitable eukaryote hosts include yeasts and mammalian cells. Examples include but are not limited to *Saccharomyces* (e.g. *S. cerevisiae*); 293 (human embryonic kidney) (ATCC CRL-1573); 293F (Invitrogen, Carlsbad Calif.); 293T and variant 293T/17 (293tsA1609neo and variant ATCC CRL-11268) (human embryonic kidney transformed by SV40 T antigen); COS-1 and COS 7 (monkey kidney CVI line transformed by SV40)(ATCC CRL1651); BHK (baby hamster kidney cells) (ATCC CRL10); CHO (Chinese hamster ovary cells); mouse Sertoli cells; CVI (monkey kidney cells) (ATCC CCL70); VERO76 (African green monkey kidney cells) (ATCC CRL1587); HeLa (human cervical carcinoma cells) (ATCC CCL2); MDCK (canine kidney cells) (ATCC CCL34); BRL3A (buffalo rat liver cells) (ATCC CRL1442); W138 (human lung cells) (ATCC CCL75); HepG2 (human liver cells) (HB8065); and MMT 060652 (mouse mammary tumor) (ATCC CCL51).

Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, HeLa, mouse L-929 cells, 3T3 lines derived from Swiss, Balb-c or NIH mice, BHK or HaK hamster cell lines.

The amyloid-reactive peptides and fusion peptides described herein may be produced by transforming or transfecting host cells with nucleic acids encoding the amyloid-reactive peptides and fusion peptides. Methods for transforming and transfecting host cells with nucleic acids are well known and routinely performed. The nucleic acid sequences encoding the amyloid-reactive peptides and fusion peptides described herein also may be introduced into cultured mammalian cells by, for example, calcium phosphate-mediated transfection (Wigler et al., Cell 14: 725, 1978; Corsaro and Pearson, Somatic Cell Genetics 7: 603, 1981; Graham and Van der Eb, *Virology* 52: 456, 1973). Other techniques for introducing cloned DNA sequences into mammalian cells, such as electroporation (Neumann et al., *EMBO J.* 1: 841-845, 1982), or lipofection may also be used. In order to identify cells that have integrated the cloned DNA, a selectable marker is generally introduced into the cells along with the gene or cDNA of interest. Examples of selectable markers for use in cultured mammalian cells include genes that confer resistance to drugs, such as neomycin, hygromycin, and methotrexate. The selectable marker may be an amplifiable selectable marker, for example, the DHFR gene and the DHFRr. Selectable markers are reviewed by Thilly (Mammalian Cell Technology, Butterworth Publishers, Stoneham, Mass.) and the choice of selectable markers is well within the level of ordinary skill in the art.

Antibodies to Amyloid-Reactive Peptides and Fusion Peptides

As provided herein, any antibodies that bind amyloid-reactive peptides and fusion peptides can be used within the scope of the methods and compositions described herein. More particularly, the various amyloid-reactive peptides and fusion peptides described herein bind to amyloids. Hence, binding of an antibody to one or more of the amyloid-reactive peptides and fusion peptides results in targeting of the antibody to the amyloid. As such, an antibody that binds to the amyloid-reactive peptides and fusion peptides described herein may be used within the scope of the present disclosure to target antibodies to amyloid deposits.

In certain example embodiments, the antibodies specifically bind any one of the amyloid-reactive peptides having the sequence set forth in SEQ ID NOS. 1-17 in Table 2. In certain example embodiments, the antibodies bind to one or more functional, peptide fragments of the amyloid-reactive peptides that are at least 60%, at least 65%, at least 70%, at least 75%, at least 80%, at least 85%, at least 90%, or at least 95% identical to one or more of the sequences set forth as SEQ ID NOS:1-17 in Table 2.

In certain example embodiments, antibodies to the amyloid-reactive peptides are generated by immunizing a suitable host with peptide p43 (SEQ ID NO: 12) and AA amyloid containing material. In such embodiments, the generated antibodies may be reactive to amyloid-reactive peptides p5, p9, p31, p43, p44, p50, p58, and p5+14 (see Table 4 (below) for antibody reactivity and Table 2 (above) for corresponding sequence identification number designations of the peptides). In certain example embodiments, provided are cell lines producing the antibodies provided in Table 4 below. Also provided are sub-clones and variant clones of such cell lines, which still produce an antibody with amyloid-reactive protein binding properties of as described herein.

The antibodies described herein may be human, humanized, or chimeric antibodies. In certain example embodiments, the antibodies may be human, humanized, or chimeric antibodies that specifically bind to any one of the amyloid-reactive peptides having the sequence set forth as SEQ ID NOS. 1-17 or fragments thereof. For example, the antibodies may be human, humanized, or chimeric antibodies that specifically bind functional peptide fragments of the amyloid-reactive peptides that are at least 60%, at least 65%, at least 70%, at least 75%, at least 80%, at least 85%, at least 90%, or at least 95% identical to one or more of the sequences set forth as SEQ ID NOS. 1-17. In certain example embodiments, the antibodies may be human, humanized, or chimeric antibodies that bind an epitope of the amyloid-reactive fusion peptides described herein. For example, the antibody may be a humanized 11-1F4 antibody or functional fragment thereof that binds the Len(1-16) epitope of the 11-1F4 12-mer epitope described herein.

In certain example embodiments, the human antibody is of human isotype IgG1, IgG2, IgG3 or IgG4. In certain example embodiments, the humanized antibody is of human isotype IgG1, IgG2, IgG3 or IgG4. In certain example embodiments, the chimeric antibody is of human isotype IgG1, IgG2, IgG3 or IgG4. In certain example embodiments, the antibody is a mouse antibody or rabbit antibody. In certain example embodiments, the antibody is a polyclonal antibody. In certain example embodiments, the antibody is a monoclonal antibody. For example, the antibody is a monoclonal antibody that recognizes a specific epitope on or attached to the amyloid-reactive peptide.

In certain example embodiments, the antibodies are amyloid-reactive antibodies. For example, the antibody can be a monoclonal antibody (or "mAB") that recognizes an epitope that is common to both an amyloid-reactive fusion peptide and a specific amyloid. Example amyloids to which the amyloid-reactive antibodies may bind include but are not limited to one or more of AA, AL, AH, ATTR, Aß2M, ALect2, Wild type, TTR (wt), AApoAI, AApoAII, AGel, ALys, ALect2, Afib, ACys, ACal, AMedin, AIAPP, APro, AIns, APrP, or Aβ amyloids. In such example embodiments, the amyloid-reactive peptide is fused to an epitope recognized by the antibody as described herein. Hence, the amyloid-reactive antibody recognizes the fused epitope of the amyloid-reactive fusion peptide. The amyloid-reactive antibody also recognizes an amyloid directly, such as via a common epitope of the amyloid from which the epitope is derived.

In certain example embodiments, the antibody is an 11-1F4 antibody or functional fragments thereof that binds an amyloid-reactive fusion peptide. The 11-1F4 antibody, for example, has been shown to bind AL amyloid in patients with AL. Yet not all subjects are immunoreactive to 11-1F4 and this mAb does not bind ATTR or AA amyloid in vivo. Therefore, to advantageously enhance the utility of the 11-1F4 antibody, a binding motif of the 11-1F4 antibody may be fused to an amyloid-reactive peptide as described herein.

For example, an 11-1F4 binding motif may be fused to one or more pan amyloid-reactive peptides as described herein to result in an amyloid-reactive fusion peptide. The 11-1F4 antibody, which when used alone has the disadvantages noted above, can then advantageously be used as a single antibody to target multiple amyloid types via binding to the pan amyloid-reactive fusion peptide. In other words, the use of 11-1F4 or fragments thereof can be expanded beyond interaction with a few amyloid types and can be used in subjects otherwise not immunoreactive.

In certain example embodiments, the 11-1F4 antibodies may bind a Len(1-16)-based epitope that is fused to the amyloid-reactive peptide of the amyloid-reactive fusion peptide. Additionally or alternatively, the 11-1F4 antibody may bind to an amyloid-reactive fusion peptide having the sequence set forth as SEQ ID NOS:18, which includes an 11-1F4 12-mer binding motif and linker region. Additionally or alternatively, the 11-1F4 antibody may bind to an amyloid-reactive fusion peptide having the sequence set forth as any one of SEQ ID NOS:19-20, which includes an 11-1F4 12-mer binding motif and a variable linker region.

In accordance with the methods described herein, use of an amyloid-reactive antibody that binds to a pan amyloid-reactive fusion peptide has the advantage of (1) using a single antibody to target a specific amyloid directly and (2) using the same, single antibody to target a vast array of other amyloid types via the amyloid-reactive peptide (when the antibody alone may not otherwise bind the variety of amyloid types). For example, with the present disclosure, use of the 11-1F4 antibody is greatly expanded to treat a variety of amyloid-based diseases via targeting of the 11-1F4 antibody to multiple amyloid types via an amyloid-reactive fusion peptide that includes an 11-1F4 binding motif.

In certain example embodiments, the antibody is the 2A4, 7D8, or 8G9 monoclonal antibody, derivatives, or functional fragments thereof, such as humanized, chimeric and fragmented versions of these 2A4, 7D8, or 8G9 mAb. See J. S. Wall, et al., AL Amyloid Imaging and Therapy with a Monoclonal Antibody to a Cryptic Epitope on Amyloid Fibrils, *PLoS ONE* 7(12):e52686 (2012); J. S. Wall et al., Generation and Characterization of anti-AA Amyloid-Specific Monoclonal Antibodies; *Frontiers of Immunology* doi: 10.3389/fimmu.2011.00032 (2011). For example, the 7D8 antibody may be used to bind amyloids directly, or the fusion peptides described herein. The 7D8 antibody, for example, is known to bind both human and murine AA amyloid, as well as human ALκ and ALλ, amyloid deposits via a cryptic epitope expressed on the C-terminally truncated or fibrillar form of the precursor proteins, respectively. The 7D8 mAb has been shown to not significantly bind ATTR amyloid, for example—at least not as well as it does bind AL amyloid (See FIGS. 25-27 and 32-41). But when used in combination with the fusion peptides described herein, binding to ATTR amyloid was greatly enhanced (see examples below).

In certain example embodiments, the antibodies or antigen-binding fragments thereof that (a) compete for binding to an epitope that includes $X_1$-ED-$X_2$ (SEQ ID NO: 53) with a 2A4, 7D8, or 8G9 antibody; (b) bind to the same epitope that includes $X_1$-ED-$X_2$ (SEQ ID NO: 53) as a 2A4, 7D8, or 8G9 antibody; (c) have an antigen-binding domain of a 2A4, 7D8, or 8G9 antibody; or (d) include the six complementarity determining regions (CDRs) of a 2A4, 7D8, or 8G9 antibody. The invention also provides chimeric or humanized versions of a 2A4, 7D8, or 8G9 antibody. Such antibodies or antigen-binding fragments are described in International Patent Application WO2009/086539 (PCT/US2008/088493), the contents of which are expressly incorporated herein in its entirety. Example antibodies, which specifically bind to an epitope that includes $X_1$-ED-$X_2$ (SEQ ID NO: 53), also include antibodies having at least one, two, or three of the complementarity determining regions (CDRs) of a light chain of a 2A4, 7D8 or 8G9 antibody. Antibodies of the invention, which specifically bind to an epitope that includes $X_1$-ED-$X_2$ (SEQ ID NO: 53), also include antibodies having at least one, two, or three of the CDRs of a heavy chain of a 2A4, 7D8, or 8G9 antibody.

CDRs can be identified according to methods known in the art. For example, numbering systems for identifying CDRs are in common use. The Kabat definition is based on sequence variability, and the Chothia definition is based on the location of the structural loop regions. The AbM definition is a compromise between the Kabat and Chothia approaches. The CDRs of the light chain variable region are bounded by the residues at positions 24 and 34 (CDR1-L), 50 and 56 (CDR2-L), and 89 and 97 (CDR3-L) according to the Kabat, Chothia, or AbM algorithm. According to the Kabat definition, the CDRs of the heavy chain variable region are bounded by the residues at positions 31 and 35B (CDR1-H), 50 and 65 (CDR2-H), and 95 and 102 (CDR3-H) (numbering according to Kabat). According to the Chothia definition, the CDRs of the heavy chain variable region are bounded by the residues at positions 26 and 32 (CDR1-H), 52 and 56 (CDR2-H), and 95 and 102 (CDR3-H) (numbering according to Chothia). According to the AbM definition, the CDRs of the heavy chain variable region are bounded by the residues at positions 26 and 35B (CDR1-H), 50 and 58 (CDR2-H), and 95 and 102 (CDR3-H) (numbering according to Kabat). See Martin et al. (1989) *Proc. Natl. Acad. Sci. USA* 86: 9268-9272; Martin et al. (1991) *Methods Enzymol.* 203: 121-153; Pedersen et al. (1992) *Immunomethods* 1: 126; and Rees et al. (1996) In Sternberg M. J. E. (ed.), *Protein Structure Prediction*, Oxford University Press, Oxford, pp. 141-172.

The antibodies described herein further include an antibody that binds specifically to an epitope comprising $X_1$-ED-$X_2$ (SEQ ID NO: 53), wherein $X_1$ and $X_2$ are any amino acid, having variable regions derived from variable regions of a 2A4, 7D8, or 8G9 antibody. Antibodies having variable regions of 2A4, 7D8, or 8G9 antibodies are also included.

The antibodies described herein further include chimeric antibodies, human antibodies, humanized antibodies, single chain antibodies, tetrameric antibodies, tetravalent antibodies, multispecific antibodies domain-specific antibodies, domain-deleted antibodies or fusion proteins.

In certain example embodiments, functional fragments of the antibodies described herein may be used in accordance with the methods and compositions provided herein. For example, fragments comprising only a portion of the primary antibody structure may be produced wherein the fragment substantially retains the immunoreactive properties the antibody. Such fragments include, for example, fragments produced by proteolytic cleavage of intact antibodies by methods well known in the art, or fragments produced by inserting stop codons at the desired locations in the nucleotide sequence using site-directed mutagenesis. For example, a stop codon can be inserted after CH1 to produce Fab fragments or after the hinge region to produce F(ab') 2fragments. Single chain antibodies and fusion proteins that include at least an immunoreactive fragment are also included within the scope of the invention. In certain example embodiments, the antibody or fragment thereof may be directly or indirectly attached to effector moieties having therapeutic activity. Suitable effector moieties include cytokines, cytotoxins, radionuclides, drugs, immunomodulators, therapeutic enzymes, anti-proliferative agents, etc. Methods for attaching antibodies to such effectors are well known in the art.

Antibodies to the amyloid-reactive peptides and fusion peptides provided herein can be prepared using any method. For example, any substantially pure amyloid-reactive peptide or fragment thereof can be used as an immunogen to elicit an immune response in an animal such that specific antibodies are produced. For example, any of amyloid-reactive peptides or fragments thereof having the sequence set forth as SEQ ID NOS: 1-17 may be used as an immunizing antigen to generate antibodies to the amyloid-reactive peptides.

In certain example embodiments, any of amyloid-reactive peptides described herein or fragments thereof may be combined with murine AA amyloid-containing material (amyloid-enhancing factor or "AEF"). The complex of amyloid-reactive peptides or fragments thereof with the AEF can then be used as the immunogen. For example, peptide p43 (SEQ ID NO: 12) may be mixed with AEF. Mice may then be immunized with a suspension of complexed AEF/p43 to generate the antibodies to the amyloid-reactive peptide (see Table 4 herein).

Additionally or alternatively, the immunogen used to immunize an animal can be chemically synthesized or derived from translated cDNA. Further, the immunogen can be conjugated to a carrier polypeptide, if desired. Commonly used carriers that are chemically coupled to an immunizing polypeptide include, without limitation, keyhole limpet hemocyanin (KLH), thyroglobulin, bovine serum albumin (BSA), and tetanus toxoid.

The preparation of polyclonal antibodies is well known to those skilled in the art. See, e.g., Green et al, Production of Polyclonal Antisera, in *Immunochemical Protocols* (Manson, ed.), pages 15 (Humana Press 1992) and Coligan et al, Production of Polyclonal Antisera in Rabbits, Rats, Mice and Hamsters, in *Current Protocols in Immunology*, section 2.4.1 (1992). In addition, those of skill in the art will know of various techniques common in the immunology arts for purification and concentration of polyclonal antibodies, as well as monoclonal antibodies (Coligan, et al., Unit 9, Current Protocols in Immunology, Wiley *Interscience,* 1994).

The preparation of monoclonal antibodies is also well known to those skilled in the art. See, e.g., Kohler & Milstein, Nature 256:495 (1975); Coligan et al, sections 2.5.1 2.6.7; and Harlow et al, *Antibodies: A Laboratory Manual*, page 726 (Cold Spring Harbor Pub. 1988). Briefly, monoclonal antibodies can be obtained by injecting mice with a composition comprising an antigen, such as one of the amyloid-reactive peptides described herein, verifying the presence of antibody production by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein A Sepharose, size exclusion chromatography, and ion exchange chromatography. See, e.g., Coligan et al, sections 2.7.1 2.7.12 and sections 2.9.1 2.9.3; Barnes et al, Purification of Immunoglobulin G (IgG), in *Methods In Molecular Biology*, VOL. 10, pages 79 104 (Humana Press 1992).

In addition, methods of in vitro and in vivo multiplication of monoclonal antibodies is well known to those skilled in the art. Multiplication in vitro can be carried out in suitable culture media such as Dulbecco's Modified Eagle Medium or RPMI 1640 medium, optionally replenished by mammalian serum such as fetal calf serum, or trace elements and growth sustaining supplements such as normal mouse peritoneal exudate cells, spleen cells, and bone marrow macrophages. Production in vitro provides relatively pure antibody preparations and allows scale up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells (e.g., osyngeneic mice) to cause growth of antibody producing tumors. In certain example embodiments, the animals are primed with a hydrocarbon, especially oils such as pristane (tetramethylpentadecane) prior to injection. After one to three weeks, the desired monoclonal antibody is recovered from the body fluid of the animal. In some cases, the antibodies provided herein can be made using non-human primates. General techniques for raising therapeutically useful antibodies in baboons can be found, for example, in Goldenberg et al, International Patent Publication WO 91/11465 (1991) and Losman et al, Int. J. Cancer, 46:310 (1990).

In certain example embodiments, the antibodies can be humanized monoclonal antibodies. Humanized monoclonal antibodies can be produced by transferring mouse complementarity determining regions (CDRs) from heavy and light variable chains of the mouse immunoglobulin into a human variable domain, and then substituting human residues in the framework regions of the murine counterparts. The use of antibody components derived from humanized monoclonal antibodies alleviates potential problems associated with the immunogenicity of murine constant regions when treating humans. General techniques for cloning murine immunoglobulin variable domains are described, for example, by Orlandi et al., *Proc. Natl Acad. Sci. USA,* 86:3833 (1989). Techniques for producing humanized monoclonal antibodies are described, for example, by Jones et al., *Nature,* 321:522 (1986); Riechmann et al, Nature, 332:323 (1988); Verhoeyen et al, *Science,* 239:1534 (1988); Carter et al, *Proc. Nat'l. Acad. Sci. USA,* 89:4285 (1992); Sandhu, Crit. Rev. Biotech., 12:437 (1992); and Singer et al, *J. Immunol,* 150:2844 (1993).

Methods and Pharmacological Compositions

Therapeutic methods are provided for the treatment of amyloidosis, including amyloid diseases such as Alzheimer's disease, Huntington's or prion diseases, or peripheral such as seen in patients with light chain (AL) amyloidosis and type 2 diabetes. In certain example embodiments, the method includes selecting a subject with amyloidosis within whom amyloid deposits are to be cleared. The method also includes administering an effective amount of one or more amyloid-reactive peptides or amyloid-reactive fusion peptides to the subject. In certain example embodiments, the subject may be administered one or more of the peptides having the sequence set forth as SEQ ID NOS:1-20. The methods further include administering an effective amount of one or more antibodies described herein to the subject. Administration of the effective amount of the amyloid-reactive peptides or fusion peptides—and the antibodies described herein—results in clearance of amyloid deposit in the subject.

Also provided herein are methods for clearing amyloid deposits. For example, an amyloid deposit is contacted with an amyloid-reactive peptide or amyloid-reactive fusion peptide as described herein. The amyloid-reactive peptide or amyloid-reactive fusion peptide is then contacted with an antibody. The antibody binds the amyloid-reactive peptide and targets the amyloid deposit for clearance. Contacting the amyloid-reactive peptide or fusion peptide with the antibody that binds the amyloid-reactive peptide or fusion peptide targets the amyloid deposit for clearance.

In certain example embodiments, binding of the antibody or functional fragment thereof to an epitope fused to the amyloid-reactive fusion peptide results in increased clearance of the amyloid deposit from the subject. For example, when the antibody is an amyloid-reactive antibody, administration of the antibody alone (without the amyloid-reactive peptide) may result in some clearance of an amyloid deposit. However, when the amyloid-reactive antibody is administered following the administration of the amyloid-reactive fusion peptide, increased clearance is achieved. That is, the level of clearance may be greater via the use of the amyloid-reactive fusion peptide versus use of the amyloid-reactive antibody alone. In certain example embodiments, an increase in clearance may be observed in a subject. For example, the subject may initially be provided with amyloid-reactive antibody alone with limited improvement, i.e., little reduction in amyloid deposits. However, administration of the amyloid-reactive fusion peptide and amyloid-reactive antibody as described herein may result in greater clearance of the amyloid deposits and hence improvement in the subject.

In certain example embodiments, the methods provided herein include eliciting an immune response at the site of antibody binding to the antibody deposit via the amyloid-reactive peptide or fusion peptide. For example, administering an amyloid-reactive peptide or fusion peptide and antibody to a subject or contacting an amyloid deposit with the amyloid-reactive peptide or fusion peptide and antibody results in accumulation of immune cells as the site of the deposit. The immune cells, for example, may be macrophages or other any other cells known or implicated in an immune response that clear amyloid deposits. Advantageously, the methods and pharmaceutical compositions provided herein are able to target amyloid deposits for clearance while not affecting healthy tissue.

In certain example embodiments, the antibody is administered to a subject or placed in to contact with the amyloid deposit after a sufficient clearance period. For example, in a subject with amyloidosis the antibody is administered after a sufficient clearance period that allows unbound amyloid-reactive peptide to be cleared from the subject's system. That is, the antibody is provided to the subject after a sufficient time passes for the amyloid-reactive peptides or fusion peptide to bind amyloids and for excess amyloid-reactive peptides or fusion peptides to be eliminated from the subject. Hence, in certain example embodiments the antibody is administered at about 1, 2, 3, 4, 5, 6, 7, 8, 9, 10, 12, 14, 16, 18, 20, 24, 30, 36, 42, 48, 54, 60, 66, 72, 78, 84, or 96 hours after administration of the amyloid-reactive peptide or fusion peptide.

Figure 1B:
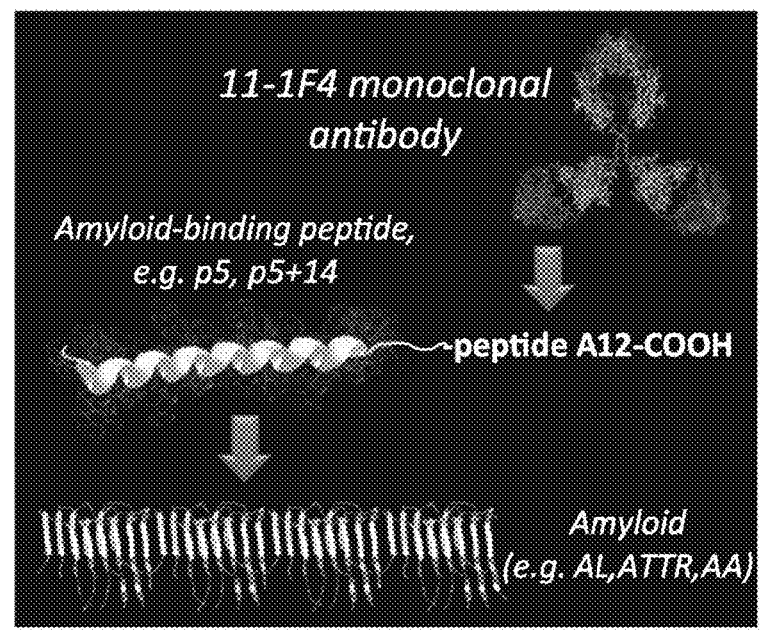
FIG. 1B is a schematic drawings showing targeting of antibodies to amyloids via amyloid-reactive via an antibody epitope (e.g., peptide A12) bound to the amyloid-reactive peptide (e.g., p5 or 05+14), in accordance with certain example embodiments.

In accordance with the methods described herein, FIG. 1A-B provides schematic drawings showing an example of targeting of antibodies to amyloids. As shown in FIG. 1A, the example amyloid-reactive peptide p5 or p5+14 pre-targets AL, ATTR, and AA amyloids. An anti-p5 antibody peptide then targets the p5 peptide. As shown in FIG. 1B, for example, an A12-based epitope of the 11-1F4 antibody (the 11-1F4 12-mer described herein) is fused to the C-terminus end of the p5 or p5+14 peptide. With the bound epitope, the amyloid-reactive peptide p5 or p5+14 pre-targets AL, ATTR, and AA amyloids and then 11-1F4 antibody binds the epitope. Binding of the 11-1F4 antibody to the epitope thus targets the 11-1F4 antibody to the p5 or p5+14 peptide and hence to the amyloid (FIG. 1B).

Figure 19A:
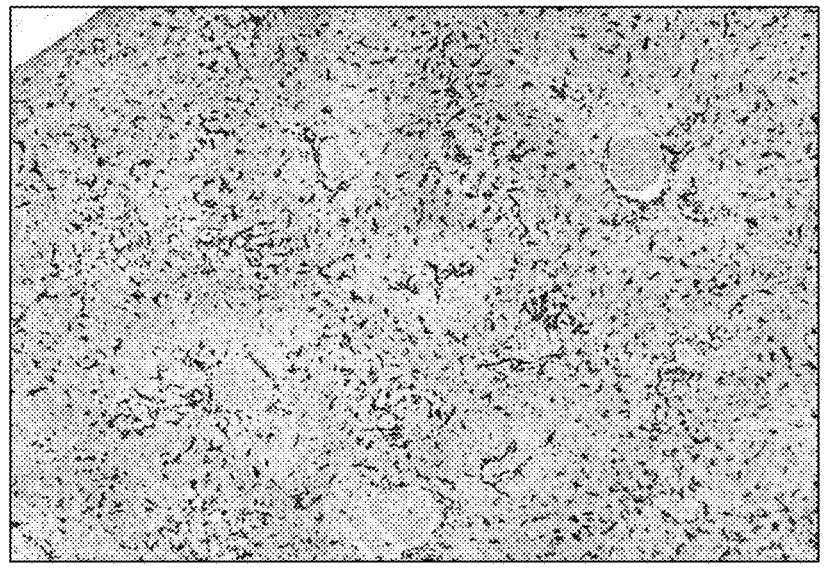
FIGS. 19A-19B are a pair of micrographs showing evaluation of liver macrophages in AA mice at 72 h post injection of 11-1F4 monoclonal antibody pre-injected with p66 or p5+14, in accordance with certain example embodiments. The combination of p66 with 11-1F4 monoclonal antibody results in increased macrophage accumulation in the liver around amyloid deposits.
Figure 19B:
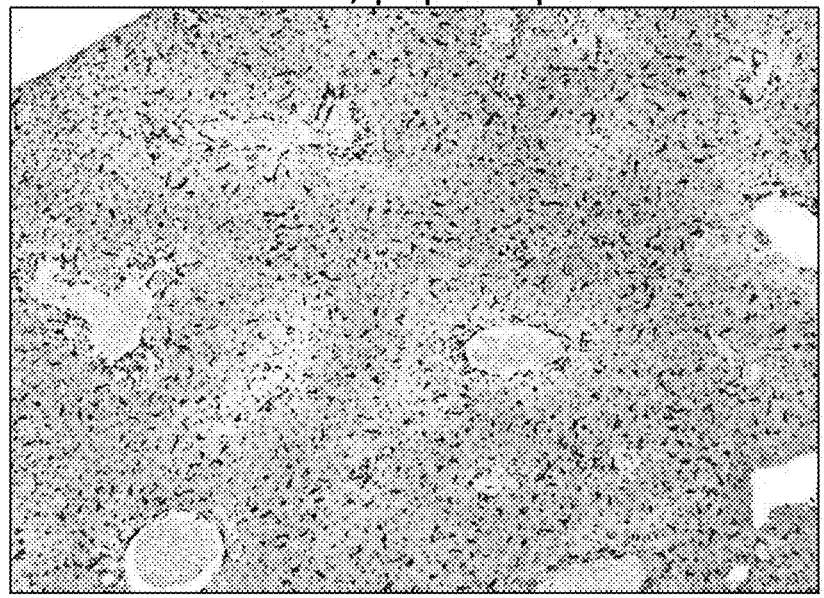

Without wishing to be bound by any particular theory, it is believed that pre-targeting of the antibodies described herein to amyloid deposits via amyloid reactive peptides elicits a host immune response to the site of the amyloid deposit. The immune response, in turn, results in clearance of the amyloid deposits, for example, through processes such as opsonization and phagocytosis. For example, anti-amyloid antibodies have been shown to clear injected amyloidomas in mice (U.S. Pat. No. 8,105,594). Further, an example immune response in the liver is illustrated in FIGS. 19A-19B, where macrophages are shown to accumulate to targeted amyloids in mice in vivo. For example, mice injected with peptide p66 and 11-1F4 antibody show induced macrophage infiltration at the site of amyloids at 72 hours post treatment (See FIGS. 19A-19B).

In certain example methods provided herein, a subject is administered an effective amount of p66 peptide or functional fragment thereof. Thereafter, such as 24-48 hours later, the subject is administered an effective amount of the 11-1F4 antibody or functional fragment thereof. Administration of the 11-1F4 antibody results in clearance of the amyloid deposits in the subject. In certain example embodiments provided herein, an amyloid deposit is contacted with p66 peptide or functional fragment thereof. Thereafter, the amyloid deposit is contacted with the 11-1F4 antibody or functional fragment thereof. Contacting the amyloid deposit with the 11-1F4 antibody results in clearance of the amyloid deposit. For example, administering the 11-1F4 antibody to the subject—or contacting an amyloid deposit with the 11-1F4 antibody—elicits an immune response at the site of the amyloid deposit, such as by eliciting macrophage or other immune cell accumulation to the site of the amyloid deposit.

In certain example embodiments, a subject is administered an effective amount of peptide with the amino acid sequence set forth as any one of SEQ ID NOS: 26-29 or functional fragments thereof. For example, the subject is administered an effective amount of the peptide having the sequence set forth as SEQ ID NO: 26. Thereafter, such as 24-48 hours later, the subject is administered an effective amount of the 7D8 antibody or functional fragment thereof. Administration of the 7D8 antibody results in clearance of the amyloid deposits in the subject. For example, administering the 7D8 antibody or functional fragment thereof to the subject—or contacting a peptope bound to an amyloid deposit with the 7D8 antibody or functional fragment thereof—elicits an immune response at the site of the amyloid deposit, such as by eliciting macrophage or other immune cell accumulation to the site of the amyloid deposit. In certain example embodiments, the subject is administered the 2A4 or 8G9 antibody, which, in accordance with the methods described herein, results in clearance of an amyloid deposit.

Also provided herein are pharmaceutical compositions for the treatment of amyloid diseases, including pharmaceutical compositions that may be used in any of the methods provided herein. The purpose of a pharmaceutical composition is to facilitate administration of a compound or substance to the subject, such as the peptides and antibodies described herein. The pharmaceutical compositions include, for example, amyloid-reactive peptides or fusion peptides. The compositions also include antibodies as described herein. In certain example embodiments, a single pharmaceutical composition for administration to a subject includes both (1) amyloid-reactive peptides or fusion peptides and (2) antibodies as described herein, whereas in other embodiments the amyloid-reactive peptides or fusion peptides and antibodies for administration to a subject are in separate pharmaceutical compositions. Such pharmaceutical compositions comprise an effective amount of the amyloid-reactive peptide (or amyloid-reactive fusion peptide) and the antibodies to treat amyloidosis in a subject, such as by clearing amyloid deposits in the subject.

In certain example embodiments, the pharmaceutical compositions will include an appropriate solid or liquid carrier, depending upon the particular mode of administration chosen. The pharmaceutically acceptable carriers and excipients useful are conventional and known to those skilled in the art. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, other proteins, such as human serum albumin or plasma preparations. If desired, the pharmaceutical composition to be administered can also contain minor amounts of non-toxic auxiliary substances, such as wetting or emulsifying agents, preservatives, and pH buffering agents and the like, for example sodium acetate or sorbitan monolaurate.

Water may be the preferred carrier when the pharmaceutical composition is administered intravenously. Saline solutions and aqueous dextrose and glycerol solutions can also be employed as liquid carriers, particularly for injectable solutions. The composition can also optionally contain minor amounts of wetting or emulsifying agents, or pH buffering agents. Such compositions can take the form of solutions, suspensions, emulsion, tablets, pills, capsules, powders, sustained-release formulations and the like. The compositions can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Examples of these and other suitable pharmaceutical carriers are described in *Remington's Pharmaceutical Sciences* (above).

In certain example embodiments, the compositions may also include a solubilizing agent and a local anesthetic such as lignocaine to ease pain at the site of the injection. The ingredients are supplied either separately or mixed together in unit dosage form, for example, as a dry lyophilized powder or water free concentrate in a hermetically sealed container such as an ampule indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided so that the ingredients may be mixed prior to administration.

Administration of therapeutic compositions can be by any common route as long as the target tissue is available via that route. This includes orthotopic, intradermal subcutaneous, intramuscular, intraperitoneal, or intravenous injection routes. Additionally or alternatively, the route may be oral, nasal, ocular, buccal, or other mucosal or topical administration. Such pharmaceutical compositions are usually administered as pharmaceutically acceptable compositions that include physiologically acceptable carriers, buffers or other excipients, as described herein.

The dosage form of the pharmaceutical composition will be determined by the mode of administration chosen. For instance, in addition to injectable fluids, topical, inhalation, oral and suppository formulations can be employed. Topical preparations can include eye drops, ointments, sprays and the like. Inhalation preparations can be liquid (e.g., solutions or suspensions) and include mists, sprays and the like. Oral formulations can be liquid (e.g., syrups, solutions or suspensions), or solid (e.g., powders, pills, tablets, or capsules). Suppository preparations can also be solid, gel, or in a suspension form. For solid compositions, conventional non-toxic solid carriers can include pharmaceutical grades of mannitol, lactose, starch, or magnesium stearate. Actual methods of preparing such dosage forms are known, or will be apparent, to those skilled in the art.

An effective amount of the pharmaceutical composition is determined based on the intended goal, for example, such as clearance of amyloid deposits. The appropriate dose will vary depending on the characteristics of the subject, for example, whether the subject is a human or non-human, the age, weight, and other health considerations pertaining to the condition or status of the subject, the mode, route of administration, and number of doses, and whether the pharmaceutical composition includes nucleic acids or viruses. Generally, the pharmaceutical compositions described herein are administered for the purpose treating amyloidosis, via clearance of the amyloid deposits. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated. In certain example embodiments, a unit dosage can be about 0.1 to about 10 mg per subject per day. Dosages from about 0.1 up to about 100 mg per subject per day may be used, particularly if the agent is administered to a secluded site and not into the circulatory or lymph system, such as into a body cavity, or into a lumen of an organ.

In certain example embodiments, the pharmaceutical compositions can be delivered by way of a pump (see Langer, supra; Sefton, *CRC Crit. Ref Biomed. Eng.* 14:201, 1987; Buchwald et al., *Surgery* 88:507, 1980; Saudek et al., *N. Engl. J. Med.* 321:574, 1989) or by continuous subcutaneous infusions, for example, using a mini-pump. An intravenous bag solution can also be employed. One factor in selecting an appropriate dose is the result obtained, as measured by the methods disclosed here, as are deemed appropriate by the practitioner. Other controlled release systems are discussed in Langer (*Science* 249:1527-33, 1990).

In certain example embodiments, a pump is implanted (for example see U.S. Pat. Nos. 6,436,091; 5,939,380; and 5,993,414). Implantable drug infusion devices are used to provide patients with a constant and long-term dosage or infusion of a therapeutic agent, including the pharmaceutical compositions described herein. Such device can be categorized as either active or passive.

Active drug or programmable infusion devices feature a pump or a metering system to deliver the composition into the patient's system. An example of such an active infusion device currently available is the Medtronic SYN-CHROMED™ programmable pump. Passive infusion devices, in contrast, do not feature a pump, but rather rely upon a pressurized drug reservoir to deliver the agent of interest. An example of such a device includes the Medtronic ISOMED™.

In certain example embodiments, the pharmaceutical compositions are delivered by sustained-release systems. Suitable examples of sustained-release systems include suitable polymeric materials (such as, semi-permeable polymer matrices in the form of shaped articles, for example films, or mirocapsules), suitable hydrophobic materials (for example as an emulsion in an acceptable oil) or ion exchange resins, and sparingly soluble derivatives (such as, for example, a sparingly soluble salt). Sustained-release compositions can be administered orally, parenterally, intracisternally, intraperitoneally, topically (as by powders, ointments, gels, drops or transdermal patch), or as an oral or nasal spray. Sustained-release matrices include polylactides (U.S. Pat. No. 3,773,919, EP 58,481), copolymers of L-glutamic acid and gamma-ethyl-L-glutamate (Sidman et al., *Biopolymers* 22:547-556, 1983, poly(2-hydroxyethyl methacrylate)); (Langer et al., *J. Biomed. Mater. Res.* 15:167-277, 1981; Langer, *Chem. Tech.* 12:98-105, 1982, ethylene vinyl acetate (Langer et al., Id.) or poly-D-(−)-3-hydroxybutyric acid (EP 133,988).

Polymers can be used for ion-controlled release. Various degradable and nondegradable polymeric matrices for use in controlled drug delivery are known in the art (Langer, Accounts Chem. Res. 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994).

In certain other example embodiments, liposomes are used for controlled release as well as drug targeting of the pharmaceutical compositions described herein (Betageri et al., *Liposome Drug Delivery Systems*, Technomic Publishing Co., Inc., Lancaster, Pa., 1993). Numerous additional systems for controlled delivery of therapeutic proteins are known (for example, U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; and U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342; and U.S. Pat. No. 5,534,496).

Single or multiple administrations of the compositions are administered depending on the dosage and frequency as required and tolerated by the subject. In one embodiment, the dosage is administered once as a bolus, but in another embodiment can be applied periodically until a therapeutic result is achieved. Generally, the dose is sufficient to treat or ameliorate symptoms or signs of disease without producing unacceptable toxicity to the subject. Systemic or local administration can be utilized.

In certain example embodiments, provided is a kit. The kit, for example, typically includes one or more of the amyloid-reactive peptides or fusion peptides described herein or functional fragments thereof, such as one or more of the amyloid-reactive peptides or fusion peptides having the sequence set forth as SEQ ID NOS:1-20 (or functional fragments thereof). The kit also includes an antibody as described herein or functional fragments thereof. The amyloid-reactive peptides or fusion peptides and antibodies of the kit, for example, may be formulated as described herein into one or more pharmaceutical compositions. The kit can include instructional materials disclosing means of use of the amyloid-reactive peptides or fusion peptides and antibodies The instructional materials may be written, in an electronic form (e.g. computer diskette or compact disk) or may be visual (e.g. video files). The kits may also include additional components to facilitate the particular application for which the kit is designed, i.e., the treatment of amyloidosis.

EXAMPLES

The following examples further illustrate the invention but should not be construed as in any way limiting its scope.

Example 1—Targeting of Antibodies to Amyloids with Amyloid-Reactive Peptides

Peptide Synthesis and Purification

Peptides were chemically synthesized and purified by high pressure liquid chromatography (HPLC [1100 series; Agilent]) by elution from a reverse-phase C3 matrix in a linear gradient of 0-50% acetonitrile in water with 0.05% trifluoroacetic acid. Peptide peaks were eluted from the column using a flow rate of 1 mL/min; 1-mL fractions were collected, peak fractions were pooled, and the mass was determined by MS using a single quadropole MS (Applied Biosystems). The purified peptides were lyophilized as 5 mg aliquots and we re-suspended in phosphate-buffered saline (150 mM NaCl, pH7.2; PBS) before use. The re-suspended peptides were stored at 4° C. until use.

Antibody Production

Five murine monoclonal antibodies were produced by using, as an immunogen, the peptide p43 mixed with murine AA amyloid-containing material (amyloid-enhancing factor). More particularly, mice were immunized with a suspension of complexed AEF/p43 (peptide and AEF were mixed and the complexes washed by centrifugation at 16,000×g before resuspending in sterile PBS). Mice received four injections of AEF/p43 immunogen (50 µg—total mass in the complexes) prepared in PBS/Alum adjuvant. Following immunization, the mice were euthanized and the mouse splenocytes were isolated and fused with SP 2/0 myeloma cells by standard PEG fusion, plated, and after 10 days in culture supernatants were screened for immunoreactivity with immunogen by direct ELISA. The wells of a 96-well microplate were coated (sequentially) with AEF and p43 peptide. Culture supernatant from fused clones was added to the wells and bound mouse antibodies were detected using horseradish peroxidase (HRP)-labeled anti-mouse IgG. ABTS was used as the colorimetric substrate and the reactivity was measured using a plate reader (Synergy HT) at 405 nm. Cells in wells with reactive supernatants, based on the ELISA described above, were subcloned by limiting dilution and subsequent clones re-screened by ELISA for reactivity with AEF/p43, as above. Supernatants from immunopositive subclones were then re-tested for binding to peptide or AEF alone coated onto the wells of a 96-well ELISA plate. Clones reactive with AEF alone were not utilized further; all other clones (clones 4, 5, 8, 12, and 13) reacted with both p43/AEF complexes and p43 alone. Peptide p43-reactive clones were propagated, isotyped (all were shown to be IgG1, kappa), and cryopreserved. For subsequent experiments (monoclonal antibodies) mAbs were purified from the subclone supernatants by protein A-affinity chromatography. In some cases, the purified mAbs were labeled with biotin by covalent linkage, using standard procedures (Pierce). Peptide reactive antibodies were further characterized for reactivity on a panel of amyloid-reactive, and related peptides by europium-linked immunosorbent assay (EuLISA). The five antibody clones, i.e., clone 4, 5, 8, 12, and 13 were then further examined as described below.

Peptide Reactivity of Subclones

The reactivity of each of the five purified and biotinylated mAbs with synthetic peptides, related in structure to p43 (see Table 2, SEQ ID NO: 12), was tested by EuLISA. More particularly, wells of a 96-well microplate were coated with 200 ng of synthetic peptide by incubation overnight. The wells were blocked by using a solution of 1% (w/v) BSA in phosphate buffered saline (pH 7.2) before addition of purified, biotinylated mAbs (clone 4, 5, 8, 12, or 13) added at 100 ng/well. Detection of bound mAb was achieved by addition of europium-conjugated streptavidin followed by enhancement solution (Perkin Elmer). The time resolved fluorescence was measured using a Victor 3 plate reader (Wallac, Perkin Elmer).

As shown in Tables 3 and 4, each of the clones was reactive with peptides with the heptad amino acid repeat, Lys-X-X-Lys-X-X-X composed of L-amino acids, where X is Ala or Gln. Alteration of the spacing of the Lys residues or substitution of Lys for Arg, or use of D-amino acids in the heptad resulted in loss or decrease of antibody binding.

TABLE 4

| Antibody Clone | Immunogen | Isotype | Peptide Reactivity |
|---|---|---|---|
| 4-2 | p43 + AEF | IgG1κ | p5+; p9+/−; p31+; p43+; p50+; p58+; p5 + 14+ |
| 5-1 | p43 + AEF | IgG1κ | p5+; p9+/−; p31+; p43+; p50+; p58+; p5 + 14+ |
| 8-1 | p43 + AEF | IgG1κ | p43+; p44+/− |
| 12-3 | p43 + AEF | IgG1κ | p5+; p9+/−; p31+; p43+; p50+; p58+; p5 + 14+ |
| 13-2 | p43 + AEF | IgG1κ | p5+; p9+/−; p31+; p43+; p50+; p58+; p5 + 14+ |

TABLE 5

(p43-AEF) Monoclonal Antibody Clone Reactivity Table

| | mAb Clone: | | | | |
|---|---|---|---|---|---|
| Peptide: | 4-2 | 5-1 | 8-1 | 12-3 | 13-2 |
| p5 | + | + | − | + | + |
| p5R | − | − | − | − | − |
| p5G | − | − | − | − | − |
| p8 | − | − | − | − | − |
| p9 | +/− | +/− | − | +/− | +/− |
| p19 | − | − | − | − | − |
| p20 | − | − | − | − | − |
| p31 | + | + | − | + | + |
| p37 | − | − | − | − | − |
| p39 | − | − | − | − | − |
| p42 | − | − | − | − | − |
| p43 | + | + | + | + | + |
| p44 | − | − | +/− | − | − |
| p48 | − | − | − | − | − |
| p50 | + | + | − | + | + |
| p58 | + | + | − | + | + |
| p5 + 14 | + | + | − | + | + |

Amyloid Fibril Pre-Targeting with p43 and p5+14 Peptides

The reactivity of each of the five mAbs to synthetic amyloid fibrils was tested by europium-linked immunosorbent assay (EuLISA). More particularly, wells of a 96-well microplate were coated with 500 ng of either murine AA amyloid-associated amyloid extract (AEF) or synthetic light chain-associated (AL) synthetic fibrils composed of the λ6 variable domain (rVλ6Wil, aka WIL) by incubation overnight. The wells were blocked by using a solution of 1% (w/v) BSA in phosphate buffered saline (pH 7.2) before addition of either peptide p43 (the immunogen) or peptide p5+14 (100 ng/well). The wells were then washed and biotinylated mAbs (clone 4, 5, 8, 12, or 13) added at 100 ng/well. Detection of bound mAb was achieved by addition of europium-conjugated streptavidin followed by enhancement solution (Perkin Elmer). The time resolved fluorescence was measured using a Victor 3 plate reader (Wallac, Perkin Elmer).

Figure 2:
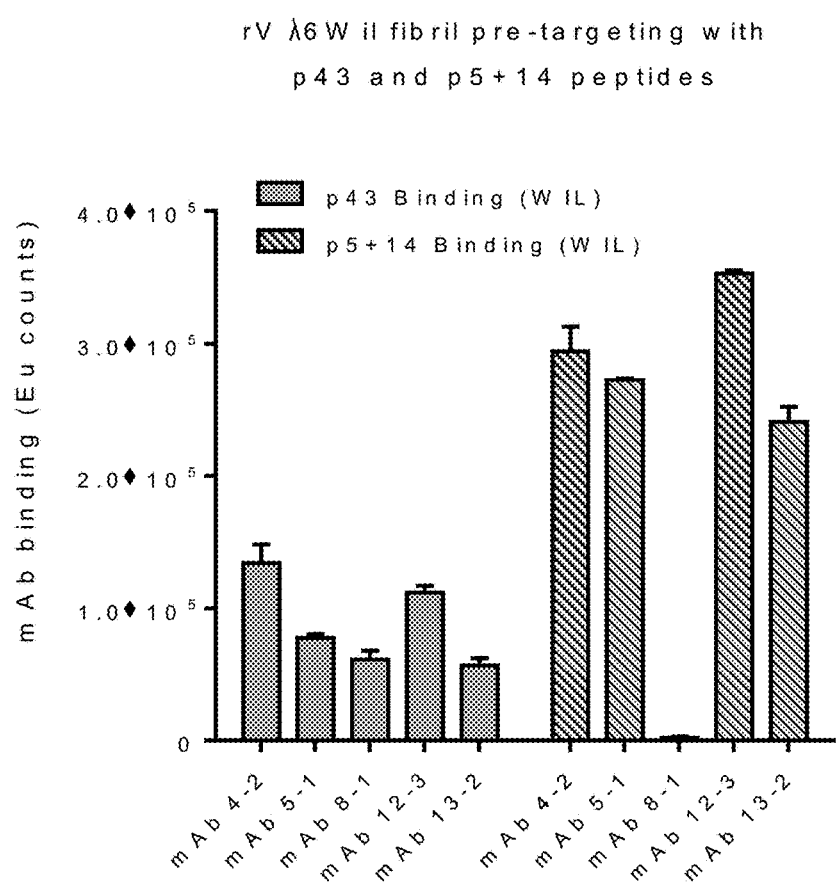
FIG. 2 is a graph demonstrating targeting of monoclonal antibody clones 4, 5, 12, and 13 to synthetic light chain-associated (AL) fibrils composed of the λ6 variable domain (rVλ6Wil, aka WIL), coated with peptide p43 or p5+14, in accordance with certain example embodiments.
Figure 3:
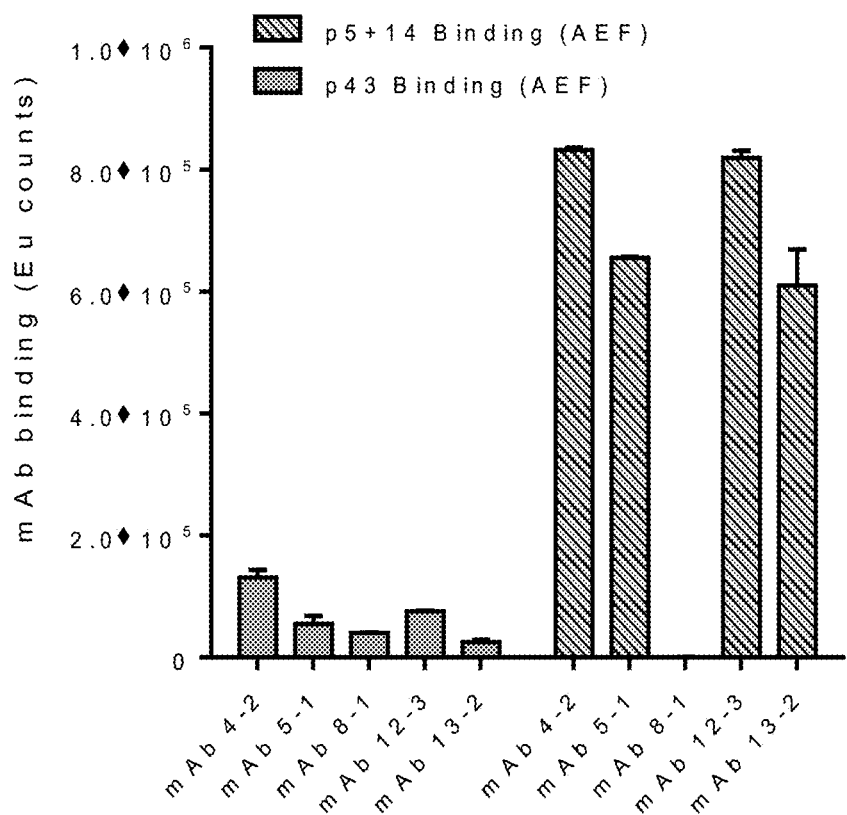
FIG. 3 is a graph demonstrating targeting of antibody clones 4, 5, 12, and 13 to murine AA amyloid-associated amyloid extract (AEF), coated with peptide p43 or p5+14, in accordance with certain example embodiments.

As shown in FIG. 2, all mAbs were reactive in the presence of fibrils coated with peptide p43, the immunogen. However, only clones 4, 5, 12, and 13 bound amyloid fibrils in the presence of peptide p5+14. There was no binding of the mAbs to the fibrils in the absence of pre-targeting peptide. As shown in FIG. 3, similar data were obtained when the peptides were used to pre-target murine AA amyloid extract (amyloid enhancing factor; AEF).

Capture of Pre-Targeting Peptide

To determine whether mAb clones 4, 5, 12, and 13 clones are capable of capturing biotinylated peptide p5+14 from solution, we used a standard ELISA assay. More particularly, 96-well ELISA microplates were coated overnight with the indicated mAbs (500 ng/well), the wells were blocked with PBS/BSA solution before addition of biotinylated p5+14 peptide (100 ng/well). Biotinylated peptides, p5R and p31G (aka p5G) were used as a negative control. Following a wash step, detection of captured peptide was achieved by addition of europium-conjugated streptavidin as described above.

Figure 4:
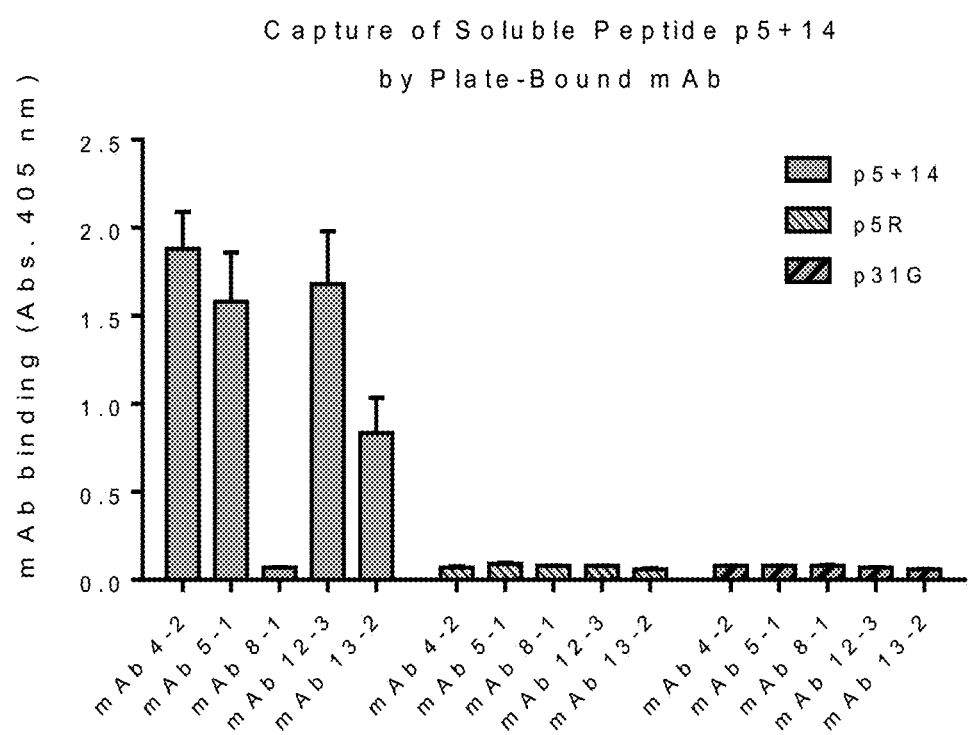
FIG. 4 is a graph demonstrating that monoclonal antibody clones 4, 5, 12, and 13 are capable of capturing biotinylated peptide p5+14 from solution, in accordance with certain example embodiments.

As shown in FIG. 4, mAb clones 4, 5, 12, and 13 were shown capable of capturing biotinylated peptide p5+14 from solution when they were adsorbed onto the wells of the microplate. In contrast, the biotinylated forms of peptides p5R and p5G that are not reactive with any of the clones were not captured (FIG. 4). The mAb clone 8 does not bind peptide p5+14 when bound to rVλ6Wil fibrils, nor AA-AEF, and did not capture biotinylated p5+14 in solution.

Binding to AA-AEF Amyloid Extract

Figure 5:
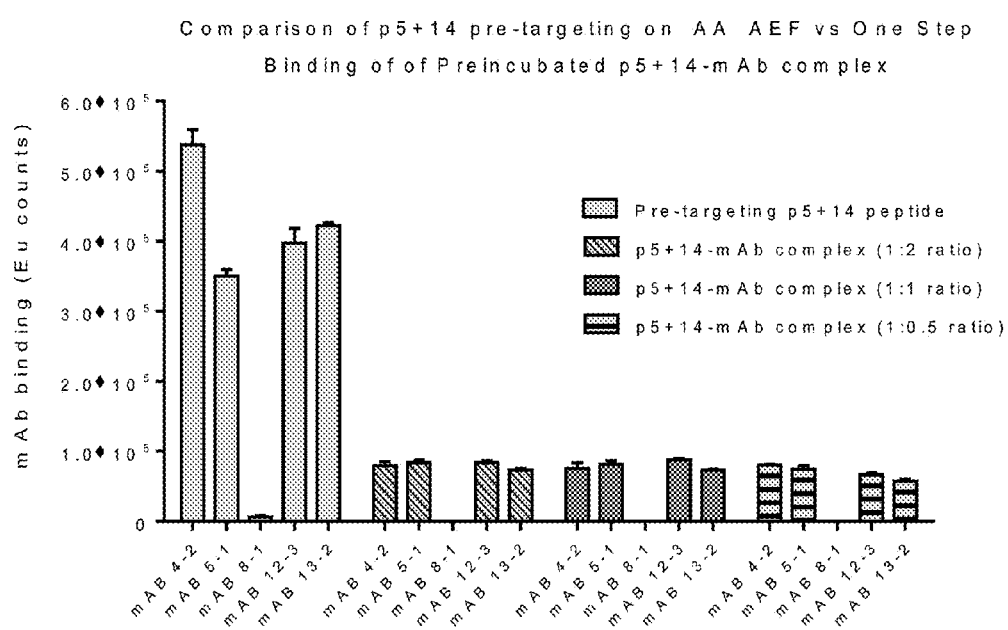
FIG. 5 is a graph showing the comparison of pre-targeting on AA AEF vs. standard one-step binding of pre-incubated complex, in accordance with certain example embodiments.

In another assay, the ability of the mAb clones to bind AA-AEF amyloid extract was examined after being pre-incubated with the amyloid-targeting peptide p5+14 to form a complex. More particularly, ELISA wells were coated with AA amyloid-associated extract (AEF: 500 ng/well overnight), The wells were blocked by using a solution of 1% (w/v) BSA in phosphate buffered saline (pH 7.2) before addition of a solution of peptide p5+14 and biotinylated mAb (4, 5, 8, 12, or 13) at 1:2, 1:1, or 1:0.5 peptide:mAb molar ratio—pre-incubated for 90 min. After one hour incubation, the plates were washed and detection of bound mAb was achieved by addition of europium-conjugated streptavidin followed by enhancement solution, as described above. As shown in FIG. 5, the binding was compared to standard pre-targeting with p5+14 before adding the mAb clones.

Pre-Targeting Immunohistochemistry

The pre-targeting efficacy of peptide p5+14 in conjunction with mAb clones 4, 5, 12, or 13 was further evaluated using human ATTR-laden formalin-fixed paraffin embedded tissue sections. More particularly, six micrometer-thick sections, cut from formalin-fixed, paraffin embedded human transthyretin (TTR) amyloid-laden tissue, were subjected to antigen retrieval by incubation with CitraPlus (BioGenex, San Ramon, Calif.) for 30 min at 90° C. Peptide p5+14 was added to the tissue at ~3 μg/mL (30× molar excess over mAb) and incubated overnight at 4° C. Unbound reagent was removed by washing in PBST for 30 min. Tissues (with or without p5+14) were immunostained with a 3 μg/mL solution of biotinylated anti-peptide mAb (clones 4, 5, 12, or 13). Slides were developed by addition of streptavidin-HRP (Vectastain Elite ABC kit, Vector Labs) followed by 3,3'-diaminobezidene (Vector Labs).

By way of positive control, a biotinylated-p5+14 peptide (without mAb) was used to directly stain TTR amyloid in this tissue (red arrows, below), as described above.

Figure 6A:
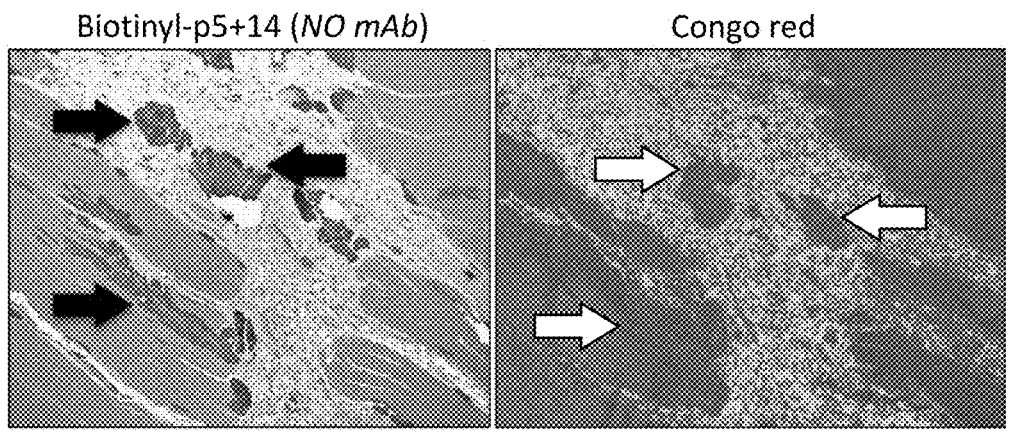
FIGS. 6A-6B are a pair of micrographs demonstrating that peptide p5+14 co-localizes with amyloid deposits, which are also observed in the Congo red-stained tissue section-, in accordance with certain example embodiments. More particularly.
Figure 6B:
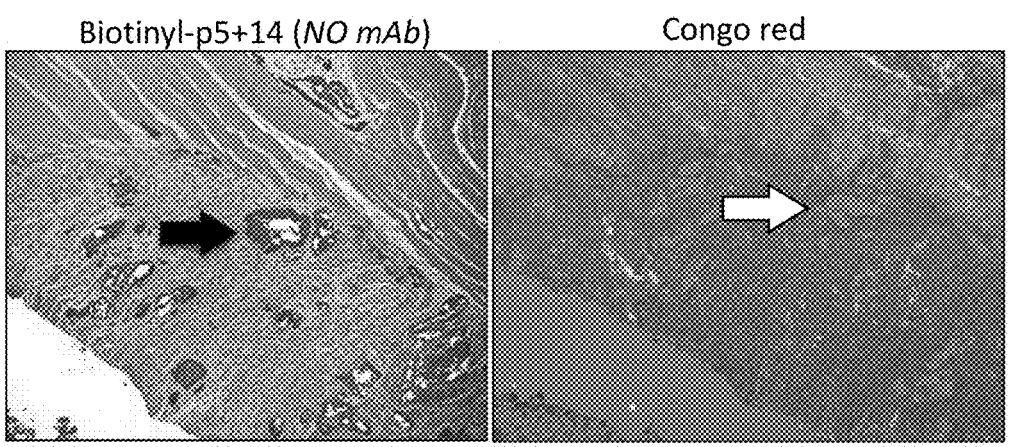
Figure 7A:
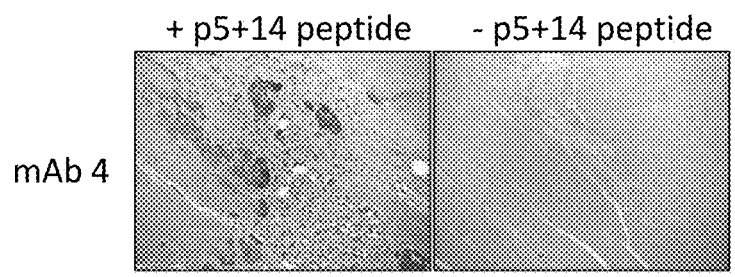
FIGS. 7A-7D are a series of micrographs comparing the binding of monoclonal antibody clones 4, 5, 12, and 13 to amyloid deposits in the presence and absence of peptide, in accordance with certain example embodiments. More particularly.
Figure 7B:
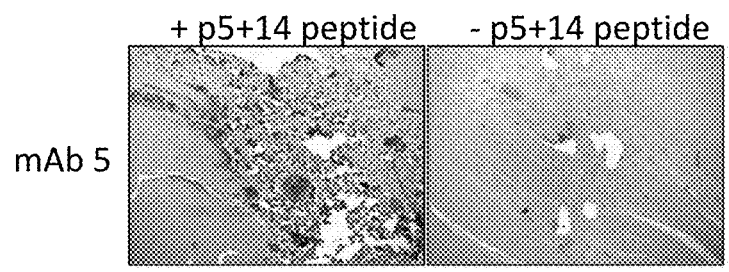
Figure 7C:
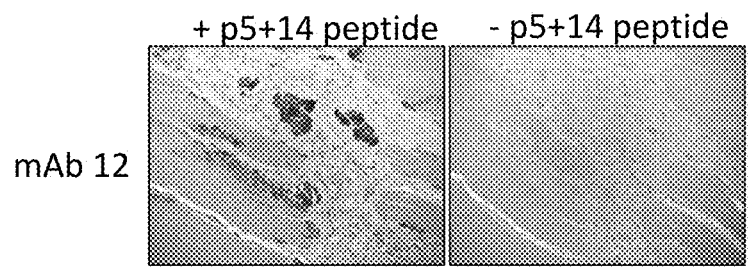
Figure 7D:
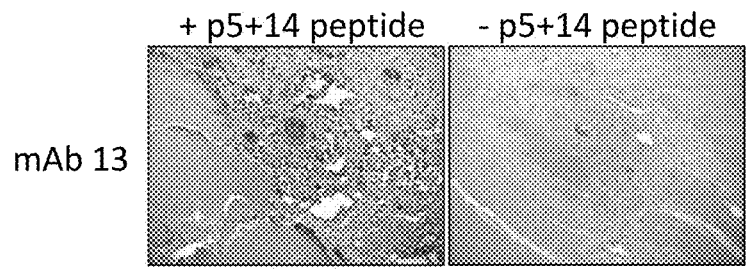

To confirm the presence and distribution of amyloid in the tissue a consecutive slide was stained with Congo red. Briefly, tissues were incubated in Congo red solution (0.8% w/v Congo red, 0.2% KOH w/v in 80% ethanol) for 1 h at RT. Sections were then washed in water and counterstained by suspending in Mayer's hematoxylin for 2 min. After rinsing for 5 min in tap water the tissues were dehydrated in ethanol ×2 and Americlear before being coverslipped using a toluene-based mounting medium. As shown in FIGS. 6A-6B, the presence of amyloid was evidenced as green-red birefringent material in the Congo red-stained tissues when viewed microscopically using cross-polarized illumination (white arrows).

When directly biotinylated and added to tissue sections containing human ATTR amyloid, p5+14 peptide co-localizes with amyloid deposits which are also observed in the Congo red-stained tissue section (FIGS. 6A-6B). When non-biotinylated peptide p5+14 is added to the tissue sections and bound to the ATTR amyloid as a pre-targeting agent for the biotinylated anti-peptide mAb, the amyloid was readily visualized in the tissue section as brown deposits. Little or no "background" staining was observed. In contrast, when the biotinylated mAbs were added in the absence of the pre-targeting p5+14 peptide there was no binding to the amyloid or healthy surrounding tissues (FIGS. 7A-7D).

Discussion

These data indicate that the p5+14 peptide (or a similar variant) can be used to pre-target amyloid before addition of immunotherapeutic antibodies, such as the subcloned mAbs 4, 5, 12, or 13. The mAbs are capable of binding directly to and targeting the amyloid-bound peptide, thereby triggering opsonization of the amyloid via a cellular immune response (see below) that is capable of removing the tissue amyloid deposits. In addition, the amyloid pre-targeting peptide can be radiolabeled and may be used as a molecular imaging agent, in addition to the first step in a pre-targeting anti-amyloid immunotherapy protocol, as described in previous work (Wall et al. 2015, *Molecules* 2015 Apr. 27; 20(5):7657-82. (PMID). Notably, because the pre-targeting peptide p5+14, and similar reagents, have been shown to bind many types of amyloid (regardless of the precursor protein from which the fibrils are formed) pre-targeting immunotherapy using, e.g., peptide p5+14 with a suitable reactive mAb can be effective in many, if not all forms of amyloidosis.

Example 2—Pre-Targeting with Amyloid-Reactive Fusion Peptide

Figure 8A:
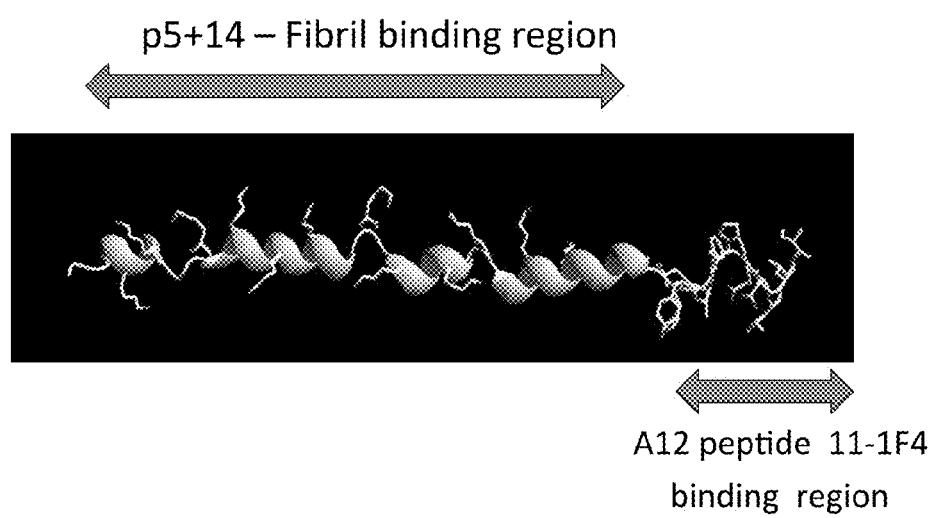
FIGS. 8A-8B are schematic drawings showing two predicted structures of p66 based on the amino acid sequence of p66, in accordance with certain example embodiments. More particularly.
Figure 8B:
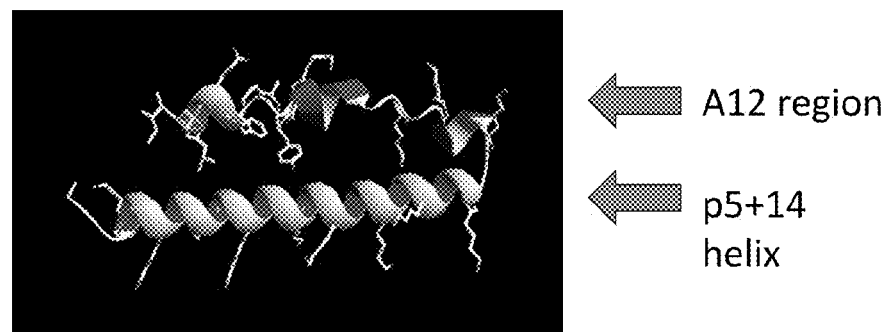

Visceral amyloidosis is characterized by the deposition of protein fibrils in vital organs leading to dysfunction and death. At present, more than 27 different proteins have been identified as components of amyloid fibrils in man, notably, immunoglobulin light chains (AL amyloid), transthyretin (ATTR), and serum amyloid protein A (AA). Immunotherapy, using amyloid fibril-reactive antibodies is being developed as a novel treatment. One antibody (mAb), designated 11-1F4 has been shown to bind AL amyloid in patients with AL. Yet not all patients were immunoreactive and this mAb does not bind ATTR or AA amyloid in vivo. Therefore, to enhance the utility of 11-1F4, we have developed a synthetic bifunctional peptide ("peptope"—designated p66 (SEQ ID NO:18) that combines a pan-amyloid-reactive peptide with a 12-mer 11-1F4 epitope sequence. The p66 peptide was generated using the Peptide Synthesis and Purification described above in Example 1. Using iTASSER (Iterative Threading ASSEmbly Refinement), we predicted two principle structures based on the amino acid sequence of p66 (FIG. 8A and FIG. 8B).

Interaction of Murine 11-1F4 with Peptide p66 and "Natural" Epitope

To show that the epitope part of p66 is not compromised by the presence of the parent p5+14 parent sequence, we evaluated the interaction of murine 11-1F4 with peptide p66 and the "natural" epitope isolated from a κ4 immunoglobulin light chain, designated Len(1-22). More particularly, costar high-binding, 96-well, microplates were coated with 50 µl per well of 0.83 mM p66 (peptope) peptide or Vκ4Len(1-22) peptide (the "natural epitope" of 11-1F4 present at the N-terminal of denatured kappa 4 light chain proteins) overnight at 37° C. The plates were washed with 1× solution of phosphate buffered saline with 0.05% (v/v) tween 20 (PBST)—similar wash steps were performed between each step. As a "blocking step" the plates were incubated for 1 h at 37° C. with 200 µl of 1% (w/v) BSA in PBS per well. The murine 11-1F4 mAb binding was assayed by titration from 100 nM (in BSAT-PBS, 0.05% (v/v) tween 20, 1% (w/v) BSA) as a starting concentration and diluted 1:2 across the microplate and incubation for 1 h at 37° C. Biotinylated goat anti-mouse secondary antibodies (Sigma) were used at a 1:3000 dilution in BSAT. Europium-conjugated streptavidin (Perkin Elmer) was added (1:1000 dilution of stock) as a detection medium and the plate incubated for 1 h 37° C. Bound 11-1G4 was quantified following addition of enhancement solution (Perkin Elmer) and the time-resolved fluorescence measured using a Victor 3 Wallac plate reader (Perkin Elmer).

Figure 9:
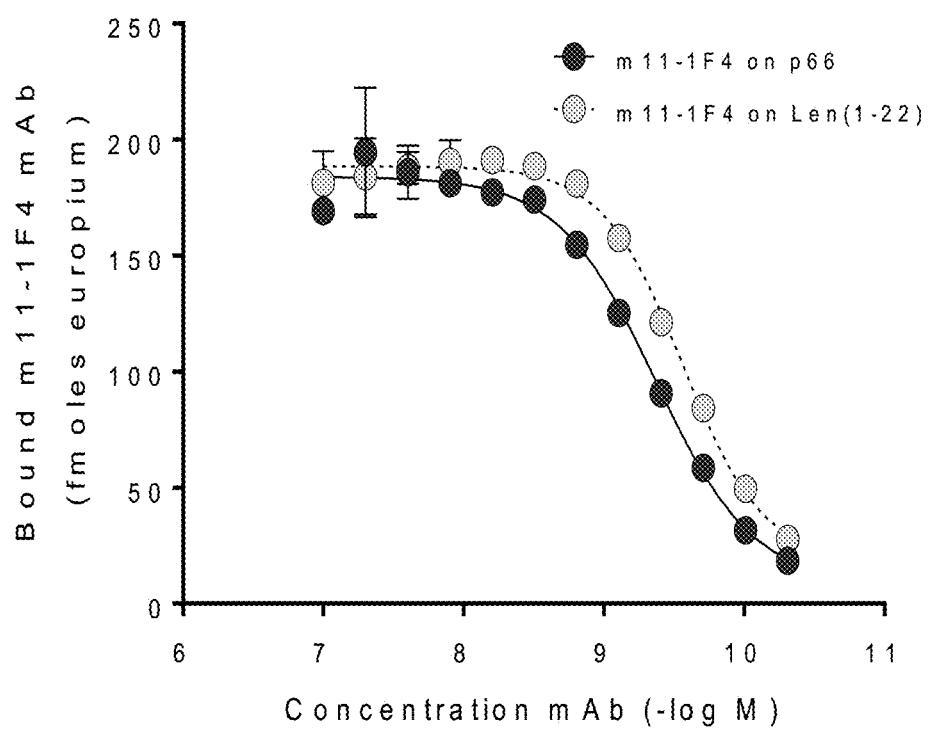
FIG. 9 is a graph showing 11-1F4 binding to p66 (11-1F4 peptope) as compared to known 11-1F4 epitope peptides [Len(1-22)], thereby demonstrating that the epitope portion of p66 is not compromised by the presence of the p5+14 sequence, in accordance with certain example embodiments.

We found that murine 11-1F4 bound both p66 and Len (1-22) when dried onto the surface of a microplate (FIG. 9), thus showing that the epitope part of p66 is not compromised by the presence of the parent p5+14 parent sequence. The estimated affinity (EC50-concentration of mAb at 50% maximal binding) was estimated to be ~0.5 nM for each peptide (FIG. 9).

Interaction of Murine 11-1F4 with Synthetic Amyloid Fibrils

Figure 10:
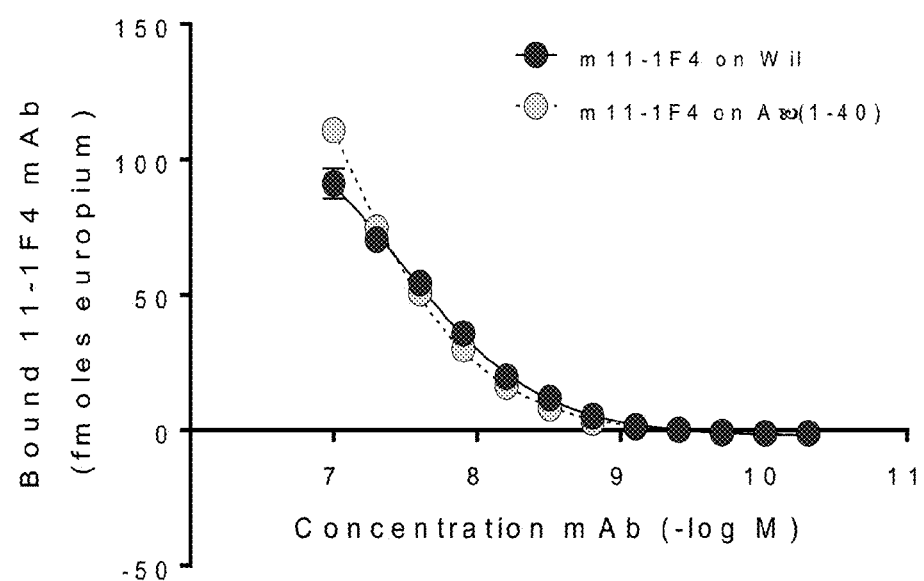
FIG. 10 is a graph demonstrating that 11-1F4 binds both Wil and Aβ(1-40) amyloid fibrils with low affinity, in accordance with certain example embodiments.

To assess the interaction of 11-1F4 with synthetic amyloid fibrils, we evaluated the interaction of murine 11-1F4 with synthetic amyloid fibrils composed of the λ6 light chain Wil-associated with light chain (AL) amyloidosis, or Aβ(1-40), associated with Alzheimer's disease and cerebral amyloid angiopathy. More particularly, Costar high binding plates were coated with 50 µl per well of 0.83 mM of synthetic amyloid fibrils composed of rVλ6Wil (AL fibrils) or Aβ(1-40) overnight at 37° C. The plates were washed with 1× solution of phosphate buffered saline with 0.05% (v/v) tween 20 (PBST)—similar wash steps were performed between each step. As a "blocking step" the plates were incubated for 1 h at 37° C. with 200 µl of 1% (w/v) BSA in PBS per well. The murine 11-1F4 mAb was added from 100 nM (in BSAT), as a starting concentration, and diluted 1:2 across the microplate and incubation for 1 h at 37° C. Biotinylated goat anti-mouse secondary antibodies (Sigma) were used at a 1:3000 dilution in BSAT. Europium-conjugated streptavidin (Perkin Elmer) was added (1:1000 dilution of stock) as a detection medium and the plate incubated for 1 h 37° C. Bound 11-1G4 was quantified following addition of enhancement solution (Perkin Elmer) and the time-resolved fluorescence measured using a Victor 3 Wallac plate reader (Perkin Elmer). We found that murine 11-1F4 bound both Wil and Aβ(1-40) fibrils, but did not saturate even at 0.1 µM 11-1F4 mAb (FIG. 10).

Figure 11:
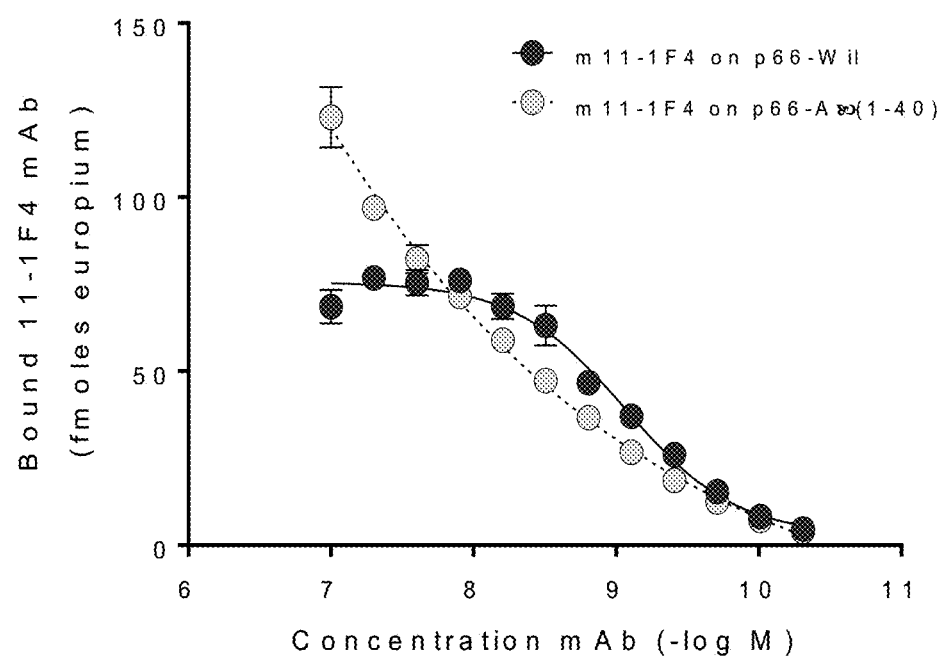
FIG. 11 is a graph demonstrating that the reactivity of the 11-1F4 monoclonal antibody is enhanced, particularly to Wil fibrils but also to the Aβ(1-40) fibrils, in the presence of p66, in accordance with certain example embodiments.

Effect of p66 on the Interaction of Murine 11-1F4 with Synthetic Amyloid Fibrils To assess the interaction of 11-1F4 antibodies with synthetic amyloid fibrils, we evaluated the interaction of murine 11-1F4 with synthetic amyloid fibrils composed of the λ6 light chain Wil-associated with light chain (AL) amyloidosis, or Aβ(1-40), associated with Alzheimer's disease and cerebral amyloid angiopathy. More particularly, we assessed the interactions in the presence of p66. Costar high binding plates were coated with 50 µl per well of 0.83 mM of synthetic amyloid fibrils composed of rVλ6Wil (AL fibrils) or Aβ(1-40) overnight at 37° C. The plates were washed with 1× solution of phosphate buffered saline with 0.05% (v/v) tween 20 (PBST)—similar wash steps were performed between each step. As a "blocking step" the plates were incubated for 1 h at 37° C. with 200 μl of 1% (w/v) BSA in PBS per well. Peptide p66 (peptope) was added to the fibril-containing wells (100 μl of a 0.83 mM stock solution) and the plate incubated for 1 h at 37° C. After a wash step to remove unbound peptope, the murine 11-1F4 mAb was added from 100 nM (in BSAT), as a starting concentration, and diluted 1:2 across the microplate and incubation for 1 h at 37° C. Biotinylated goat anti-mouse secondary antibodies (Sigma) were used at a 1:3000 dilution in BSAT. Europium-conjugated streptavidin (Perkin Elmer) was added (1:1000 dilution of stock) as a detection medium and the plate incubated for 1 h 37° C. Bound 11-1G4 was quantified following addition of enhancement solution (Perkin Elmer) and the time-resolved fluorescence measured using a Victor 3 Wallac plate reader (Perkin Elmer). We found that when p66 was added to fibrils coated to the microplate well the reactivity of the 11-1F4 mAb was enhanced, particularly to the WIl fibrils, but also to the Wil fibrils (FIG. 11).

Effect of BSA-Blocking on p66 Binding to Synthetic Fibrils

Figure 12:
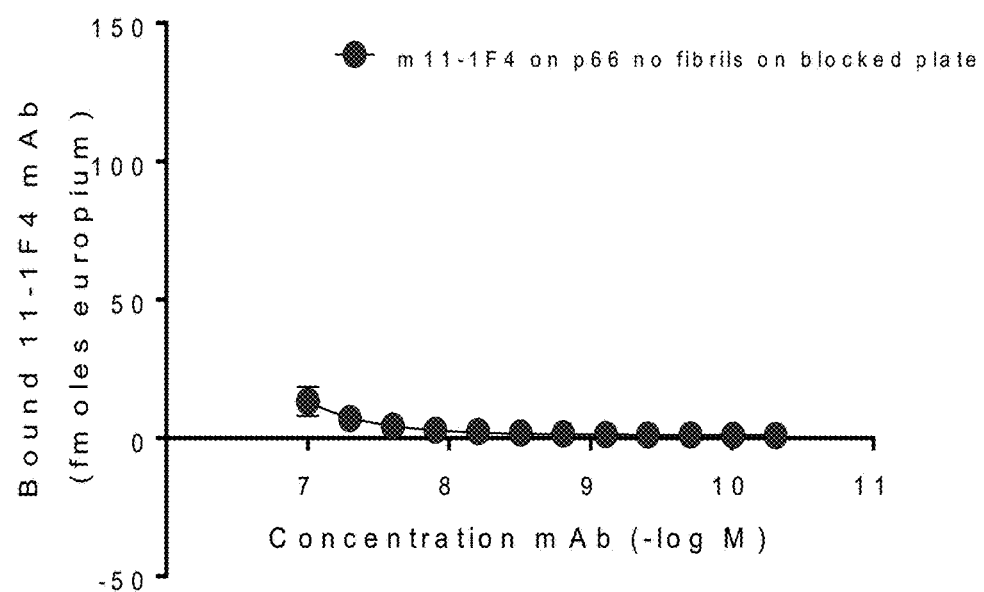
FIG. 12 is a graph demonstrating that fibril material is required for binding of p66 and hence for p66-mediated targeting of antibodies, in accordance with certain example embodiments.

To assess the interaction of 11-1F4 antibodies with synthetic amyloid fibrils, we evaluated the interaction of murine 11-1F4 with synthetic amyloid fibrils composed of the λ6 light chain Wil—associated with light chain (AL) amyloidosis, or Aβ(1-40), associated with Alzheimer's disease and cerebral amyloid angiopathy. More particularly, we assessed the blocking ability of BSA on fibril binding. Costar high binding plates were "blocked" by addition of 200 μl of 1% (w/v) BSA in PBS per well and incubation for 1 h at 37° C. Peptide p66 (peptope) was added to the blocked wells (100 μl of a 0.83 mM stock solution) and the plate incubated for 1 h at 37° C. After a wash step to remove unbound peptope, the murine 11-1F4 mAb was added from 100 nM (in BSAT), as a starting concentration, and diluted 1:2 across the microplate and incubation for 1 h at 37° C. Biotinylated goat anti-mouse secondary antibodies (Sigma) were used at a 1:3000 dilution in BSAT. Europium-conjugated streptavidin (Perkin Elmer) was added (1:1000 dilution of stock) as a detection medium and the plate incubated for 1 h 37° C. Bound 11-1G4 was quantified following addition of enhancement solution (Perkin Elmer) and the time-resolved fluorescence measured using a Victor 3 Wallac plate reader (Perkin Elmer). We found that when p66 was added to BSA-blocked wells in the absence of fibrils, no peptide bound and no mAb reactivity was observed (FIG. 12).

Binding of p66 and p5+14 to Synthetic and Naturally-Occurring Amyloid

To evaluate the binding of p66 and p5+14 to synthetic and naturally-occurring amyloid, peptides p66 or p5+14 were radiolabeled with iodine-125 (I-125, $^{125}$I) using oxidation with chloramine T (1 mg/ml in water freshly made. Free 1-125 was removed from the reaction mixture by size exclusion chromatography using a Sephadex G-25 solid phase and a 0.1% (w/v) gelatin in PBS mobile phase. Fractions of ~250 μl were collected and the radioactivity in each measured using a gamma counter (Packard Cobra II auto-gamma counter). Peptide fractions with peak radioactivity were pooled and used for the "pull-down" assays.

For the pull down assay, $^{125}$I-labeled peptide binding to murine: (m) AA and wild type (WT) liver homogenates (25 μl); rVλ6Wil (AL), Aβ(1-40) and islet amyloid polypeptide (IAPP) synthetic fibrils (25 μg), and; transthyretin-associated (ATTR), ALκ4-Cab and ALλ1-Ship human amyloid extracts (50 μg). The $^{125}$I-peptides were prepared in PBST (0.15 M NaCl) or PBST with 1 M NaCl. Ten μl (~5 ng, ~100,000 counts per min [cpm]) of the $^{125}$I-peptide solution was added to each test sample in a 200 μl volume. The reaction mixtures were rotated for 1 h at RT, then centrifuged twice at 16,000×g for 10 min. After each step the supernatants were removed and collected in test tubes. The pellets, obtained following the second spin were resuspended in PBST. The radioactivity in both the supernatant and pellet samples were measured using a Packard Cobra II auto-gamma counter. The bound peptide, expressed as % total was calculated according to:

Bound peptide (% total)=(Pellet cpm)/(Pellet cpm+ Supernatant cpm)

Figure 13A:
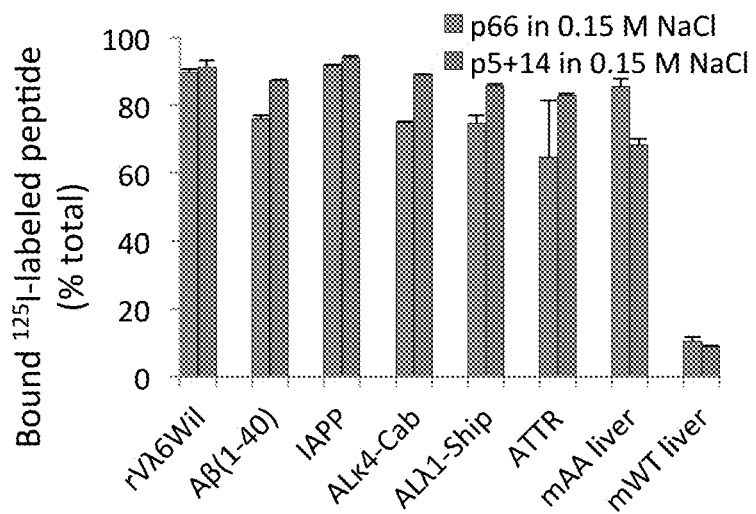
FIG. 13A is a graph showing that peptide p66 and p5+14 bind equally well to synthetic and naturally-occurring amyloid samples in 0.15 M NaCl, in accordance with certain example embodiments.
Figure 13B:
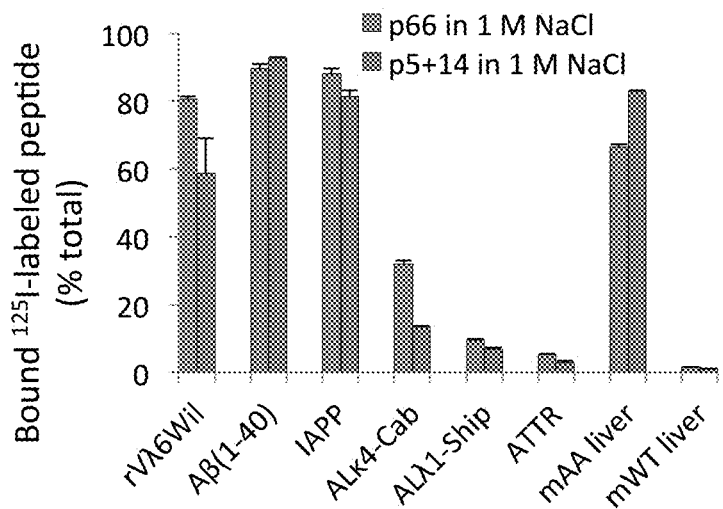
FIG. 13B is a graph showing that peptide p66 and p5+14 bind equally well to synthetic and naturally-occurring amyloid samples in 1.0 M NaCl (FIG. 13B), in accordance with certain example embodiments.
Figure 14A:
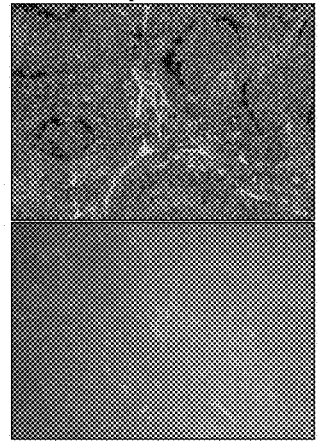
FIGS. 14A-14E are a series of microautoradiographs and Congo-red-stained micrographs demonstrating that p66 injected into mice selectively binds amyloid deposits in a variety of tissues in vivo, in accordance with certain example embodiments. More particularly.
Figure 14B:
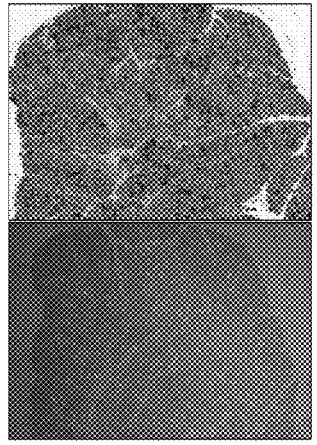
Figure 14C:
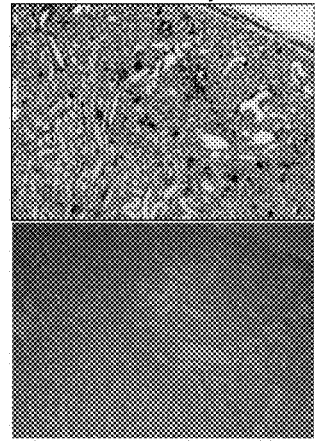
Figure 14D:
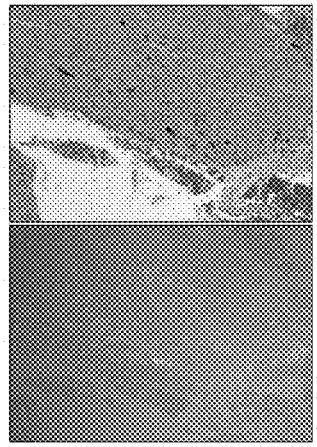
Figure 14E:
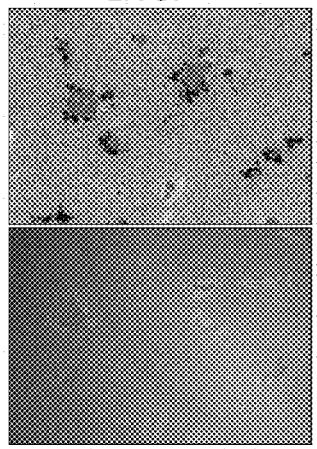

We found that both peptide p66 (the 11-1F4 peptope) and p5+14 bound equally well to synthetic and naturally-occurring amyloid samples in 0.15 M NaCl (FIG. 13A) and 1.0 M NaCl (FIG. 13B), indicating that the presence of the 11-1F4 epitope sequence did not alter the binding to, or affinity for, the amyloid samples.

Example 3—In Vivo Binding of Radiolabeled $^{125}$I-p66 Peptope to AA Amyloid in Mice Since there are no good mouse models of AL amyloidosis, we chose to investigate the reactivity of peptide p66 with systemic AA amyloidosis in a mouse model. Notably, the murine 11-1F4 mAb does not bind to AA amyloid in this mouse. Thus, this system will serve as an excellent tool to demonstrate induction of 11-1F4 reactivity by using the p66 peptide. Micro autoradiography was used to demonstrate uptake of the p66 peptide (labeled with iodine-125; $^{125}$I) in AA amyloid deposits in the mouse. Peptide p66 was produced and purified as described in Example 1. The p66 peptide was radiolabeled with $^{125}$I as described above in Example 2. Other detailed methods are provided below.

Murine Model of AA Amyloidosis

Systemic visceral AA amyloidosis was induced in H2-L$^d$-huIL-6 Tg Balb/c transgenic mice that constitutively express the human interleukin-6 transgene, by iv injection of 10 μg of purified, splenic AA amyloid (amyloid enhancing factor; AEF) in 100 μL of sterile phosphate-buffered saline (PBS). Peptide p66 was evaluated in mice at 4-6 wk post AEF injection when amyloid load was significant.

SPECT/CT Imaging of $^{125}$I-p5+14 in AA and WT Mice

Imaging was performed using WT or AA amyloid mice (n=3) that were injected with ~5 μg of $^{125}$I-p66, 125 μCi in the lateral tail vein. After the appropriate uptake time (data for 4 and 72 h pi shown), mice were euthanized by isoflurane inhalation overdose. SPECT images were acquired using an Inveon trimodality imaging platform (Siemens Preclinical Solution, Knoxville, Tenn.) running Inveon Acquisition Workplace software (ver. 2.0). Low energy ($^{125}$I; 25-45 keV) gamma photons were acquired at each of 60, 16-sec projections with 90 mm of bed travel. A 1 mm-diameter, 5-pinhole (Mouse Whole Body) collimator was used at 30 mm from the center of the field of view. Data were reconstructed post hoc onto an 88×88×312 matrix with isotropic 0.50 mm voxels using a 3D ordered subset expectation maximization (OSEM) algorithm (8 iterations; 6 subsets).

CT data were acquired using an x-ray voltage biased to 80 kVp with a 500 mA anode current, with 4×4 binning. A 225 msec exposure was used, and 360, 1-degree projections were collected. The data were reconstructed using an implementation of the Feldkamp filtered back-projection algorithm onto a 512×512×1296 matrix with isotropic 0.106 mm voxels. SPECT and CT datasets were automatically co-registered and visualized by using the Inveon Research Workplace visualization software package (Siemens Preclinical Solution, Knoxville, Tenn.). Mice were administered, IP, ~300 μL of Iohexol CT contrast agent diluted 1:1 in sterile PBS, 5 min before the imaging data were acquired.

Biodistribution Measurements

Samples of liver, spleen, pancreas, kidneys, small and large intestines, stomach and heart were harvested post mortem from every mouse undergoing imaging with $^{125}$I-p66. A sample of each was placed into a tared, plastic vial, weighed and the $^{125}$I radioactivity measured using an automated Wizard 3 gamma counter (1480 Wallac Gamma Counter, Perkin Elmer). The biodistribution data were expressed as % injected dose/g tissue (% ID/g). In addition, samples of each tissue were fixed in 10% buffered-formalin for 24 h and embedded in paraffin for autoradiography.

Micro-Autoradiography and CR Staining

For autoradiography, 6-μm-thick sections were cut from formalin-fixed, paraffin-embedded blocks, containing tissues from mice that had received $^{125}$I-p66. The sections were placed on Plus microscope slides (Fisher Scientific), dipped in NTB-2 emulsion (Eastman Kodak), stored in the dark, and developed after a 4 day exposure. Each section was counterstained with hematoxylin and eosin. Detection of amyloid was achieved in consecutive tissue sections by staining with an alkaline Congo red solution (0.8% w/v Congo red, 0.2% w/v KOH, 80% ethanol) for 1 h at room temperature followed by conunterstain with Mayer's hematoxylin for 2 min.

All tissue sections were examined using a Leica DM500 light microscope fitted with cross-polarizing filters (for Congo red). Digital microscopic images were acquired using a cooled CCD camera (SPOT; Diagnostic Instruments).

Results and Discussion

Figure 16A:
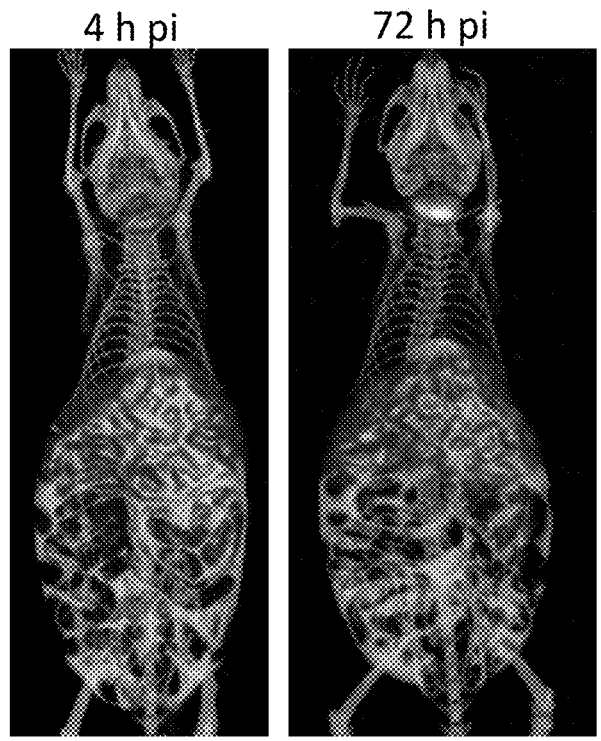
FIG. 16A is an image showing SPECT/CT imaging of $^{125}$I-p66 in AA mice at 4 and 72 h post injection (pi), in accordance with certain example embodiments.
Figure 16B:
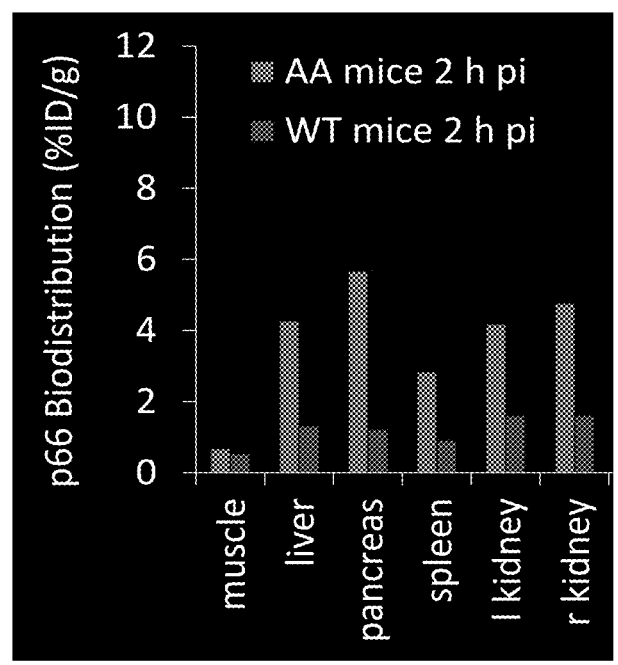
FIG. 16B is a graph showing tissue biodistribution of $^{125}$I-p66 in AA and WT (healthy, amyloid-free) mice at 2 h post injection (pi) in vivo, in accordance with certain example embodiments.
Figure 17A:
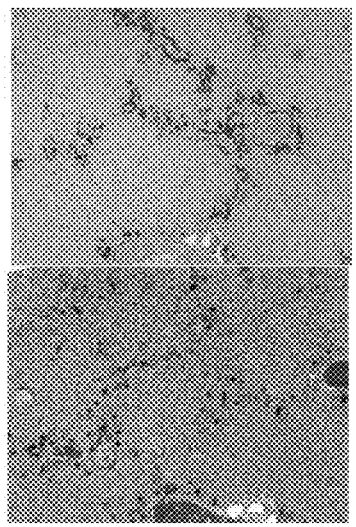
FIGS. 17A-17D are a series of micrographs and microautoradiographs from various tissue types showing evaluation of mice at 24 h post injection of 11-1F4 monoclonal antibody into AA mice pre-targeted with peptide p66 in vivo, in accordance with certain example embodiments. Peptide p66 is shown co-localizing with $^{125}$I-11-1F4 monoclonal antibody and AA amyloid. More particularly.
Figure 17B:
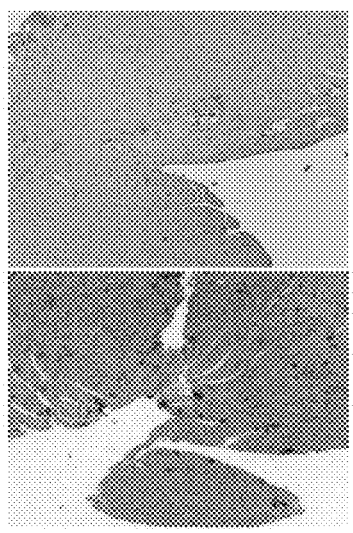
Figure 17C:
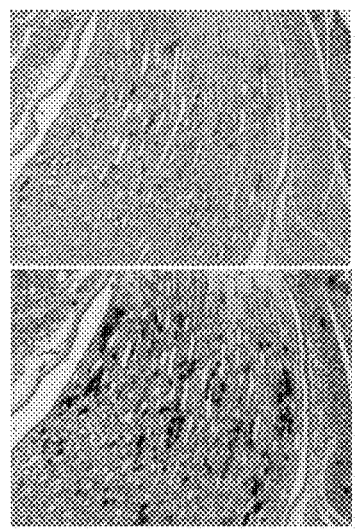
Figure 17D:
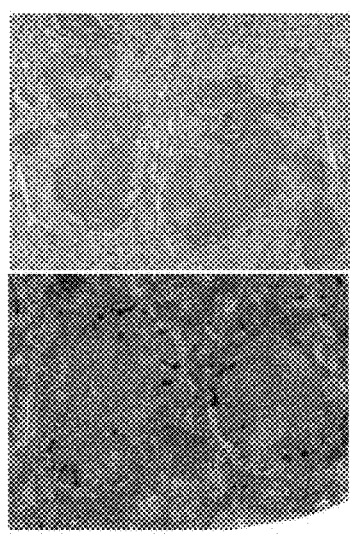
Figure 18A:
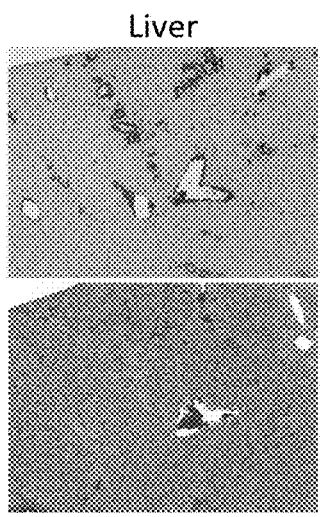
FIGS. 18A-18D are a series of micrographs and microautoradiographs from various tissue types showing evaluation of mice at 24 h post injection of $^{125}$I-11-1F4 monoclonal antibody into AA mice pre-targeted with p5+14 control peptide, in accordance with certain example embodiments. The 11-1F4 monoclonal antibody does not localize to amyloids when the mice are pre-treated with p5+14 control peptide alone. More particularly.
Figure 18C:
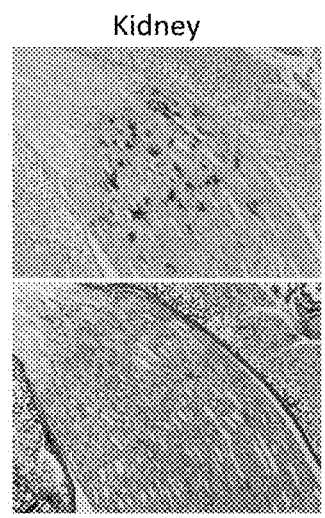
Figure 18B:
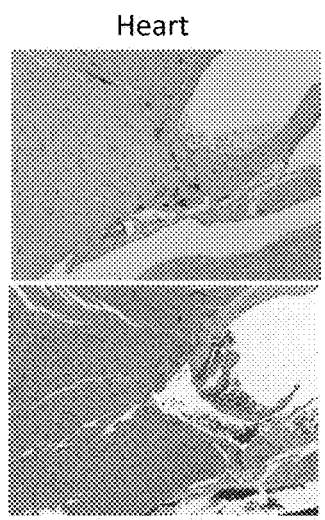
Figure 18D:
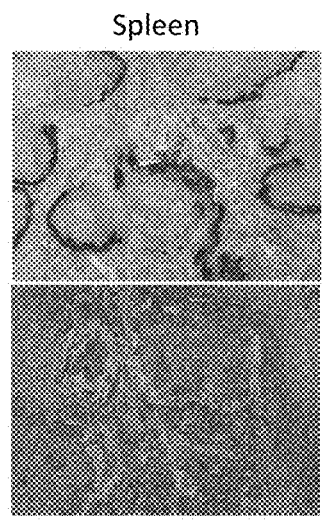

Radiolabeled ($^{125}$I) p66 injected into mice with systemic AA amyloidosis specifically bound the amyloid deposits as evidenced by the deposition of black silver grains in the autoradiographs (indicative of $^{125}$I-p66) at the sites of amyloid deposition, seen as green-gold birefringence in the Congo red-stained tissues (FIGS. 14A-14E). Further, micro autoradiography demonstrated that $^{125}$I-p66 peptide does not bind healthy tissues (FIGS. 15A-15H). More particularly, radiolabeled ($^{125}$I) p66 injected into healthy WT mice did not bind to any tissue that was studied, as evidenced by the LACK of black silver grains in the autoradiographs (indicative of $^{125}$I-p66) (FIGS. 15A-15H). Lastly, as shown in FIGS. 16A-16B, reactivity of $^{125}$I-p66 with amyloid in vivo, notably the liver, spleen, pancreas, and intestines was confirmed by SPECT/CT imaging and tissue biodistribution measurements. The reactivity with amyloid in vivo was sufficiently stable that the amyloid in the liver could be readily visualized, by SPECT imaging, at least 72 h post injection of the peptide (FIG. 16A and FIG. 16B).

Example 4—Pre-Targeting of $^{125}$I-11-1F4 to Systemic AA Amyloid In Vivo

The murine mAb 11-1F4 mAb does not efficiently bind to AA amyloid in the murine model of AA amyloidosis. Therefore, we sought to demonstrate specific AA amyloid binding in mice by $^{125}$I-11-1F4 by using peptope p66 as a pre-targeting agent. Micro autoradiography, combined with immunohistochemical detection of amyloid-bound p66 in the tissue, was used to demonstrate $^{125}$I-11-1F4 and p66 peptope binding to AA amyloid deposits in the mouse. As a control, the mice received an IV injection of peptide p5+14, instead of p66. Peptide p66 was produced and purified as described in Example 1. The p66 peptide was radiolabeled with $I^{125}$ as described above in Example 2. Other detailed methods are provided below.

Murine Model of AA Amyloidosis

Systemic visceral AA amyloidosis was induced in H2-L$^d$-huIL-6 Tg Balb/c transgenic mice that constitutively express the human interleukin-6 transgene, by iv injection of 10 μg of purified, splenic AA amyloid (amyloid enhancing factor; AEF) in 100 μL of sterile phosphate-buffered saline (PBS). Peptide p66 pre-targeting of $^{125}$I-11-1F4 was evaluated in mice at 3-4 wk post AEF injection when amyloid load was modest.

In Vivo Pre-Targeting

Three cohorts of 3 mice, each received ~400 μg of unlabeled peptide p66, and a second group of 3 cohorts were given peptide p5+14 as a control. Twenty-four hours after the peptide injection all mice were administered ~150 μCi (~20 μg) of $^{125}$I-11-1F4 IV in the lateral tail vein. One group of p66 mice (n=3) and one group of p5+14 control mice (n=3) were euthanized at 24, 48 and 72 h post injection of 11-1F4 mAb and the organs harvested at necropsy for fixation, followed by microautoradiographic and immunohistochemical analyses.

Micro-Autoradiography and Congo Red Staining

For autoradiography, 6-μm-thick sections were cut from formalin-fixed, paraffin-embedded blocks, containing tissues from mice that had received $^{125}$I-p66. The sections were placed on Plus microscope slides (Fisher Scientific), dipped in NTB-2 emulsion (Eastman Kodak), stored in the dark, and developed after a 4 day exposure. Each section was counterstained with hematoxylin and eosin. Detection of amyloid was achieved in consecutive tissue sections by staining with an alkaline Congo red solution (0.8% w/v Congo red, 0.2% w/v KOH, 80% ethanol) for 1 h at room temperature followed by counterstain with Mayer's hematoxylin for 2 min.

Immunohistochemistry

Formalin-fixed paraffin embedded tissue sections, from mice treated with p66 peptope or peptide p5+14 were subjected to antigen retrieval using citrate buffer (pH 6; Dako) 30 min at 90° C. The tissue was then blocked with hydrogen peroxide, casein, and avidin and biotin, per manufacturer's instructions. The biotinylated peptide-reactive mAb (clone 12-3 [described above]) was then added (1.6 μg/mL in PBS) an the samples incubated for 2 h at RT, O/N at 4° C., followed by another 2 h period at RT. After washing the tissue, slides were developed by adding Vector ABC Elite, for 40 min at RT, followed by Vector DAB.

The presence of macrophages was detected by staining with mAb Iba-1 (1:8000 diln) followed by addition of biotinylated rabbit anti-mouse secondary reagent (Vector Rabbit Elite kit). The slides were developed, as described above. All tissue sections were examined using a Leica DM500 light microscope fitted with cross-polarizing filters (for Congo red). Digital microscopic images were acquired using a cooled CCD camera (SPOT; Diagnostic Instruments).

Results and Discussion

At 24 h post injection of 11-1F4 mAb into AA mice pre-targeted with peptope p66, $^{125}$I-11-1F4 localizes with p66 (FIGS. 17A-17D). More particularly, brown coloration in the immunohistochemical stain is indicative of the presence of peptide p66 associated specifically with AA amyloid in the tissues (FIGS. 17A-17D). Black punctate coloration in the autoradiographs is indicative of the presence of $^{125}$I-11-1F4, which is seen exclusively co-localized with the p66-coated AA amyloid (FIGS. 17A-17D).

In contrast, evaluation of mice at 24 h post injection of 11-1F4 mAb into AA mice pre-targeted with p5+14 control peptide did not show co-localization (FIGS. 18A-18D). That is, despite the presence of brown p5+14-coated AA amyloid in all tissues evaluated, there was little evidence of $^{125}$I-11-1F4 co-localized with the amyloid, as evidenced by the absence of black silver grains in the microautoradiographs (FIGS. 18A-18D).

Lastly, liver macrophages in AA mice at 72 h post injection of 11-1F4 mAb pre-injected with p66 or p5+14 showed induced macrophage infiltration (FIGS. 19A-19B). More particularly, brown coloration was associated with the Iba-1 positive macrophages in the mouse liver. These preliminary data suggest that the combination of p66 with 11-1F4 (FIG. 19A) in AA mice induced macrophage infiltration into the liver and clustering of macrophages around amyloid deposits to a greater degree that p5+14 in conjunction with the 11-1F4 mAb (FIG. 19B).

Example 5—Peptides for Pre-Targeting Monoclonal Antibody 7D8 to Amyloid

The goal of this study was to characterize the reactivity of monoclonal antibody ("mAb") 7D8 with peptope peptides including an amyloid-targeting sequence and the four amino acid epitope for mAb 7D8. A series of peptope peptide sequences differing only in the spacer region were generated and tested for their ability to bind mAb 7D8 using in vitro assays.

Briefly, the mAb 7D8 was generated using the C-terminal four amino acids of murine AA(1-75), i.e., -HEDT-COO$^-$ ("HEDT" disclosed as SEQ ID NO: 52), as an immunogen. We therefore hypothesized that by generating a p5-epitope fusion peptide (a peptope) it would be possible to extend and enhance the reactivity of mAb 7D8 with non-AA/AL amyloid deposits as well as those AL patients may lack direct reactivity with 7D8 and therefore expand the utility of the mAb. The combination of the peptope with 7D8 will provide a novel pre-targeting system for amyloid immunotherapy with this reagent.

Materials & Methods

Four peptope sequences were synthesized (AnaSpec, Fremont, Calif.) based on the peptide p5 and the -HEDT-epitope (SEQ ID NO: 52). Each of the peptopes varied only in the 3-amino acid intervening sequence (the spacer). Peptide p5 was used as the amyloid reactive peptide, as opposed to p5+14, because the shorter sequence permitted more efficient synthesis of pure peptope peptides. All peptides were purified by reverse phase (RP) HPLC and lyophilized before use. More particularly, the peptope peptides eluted from a C3 reverse phase solid matrix using an acidified acetonitrile gradient, as a single peak at ~18% acetonitrile. The peptides were purified by RP-HPLC, the peak elution fractions were pooled, lyophilized, and rehydrated in water and the concentration determined by using a micro-BCA assay. Working solutions of peptides in PBS were generated by adding a one-tenth volume of 10×PBS before use.

As synthesized, each of the peptides included the GGGYS- (SEQ ID NO:24) or CGGYS- (SEQ ID NO:25) sequences that were fused to the N-terminus end of the peptide. The peptope primary structure, without the leader sequences, is shown in Table 6, below, with the space sequence underlined.

TABLE 6

| Peptope Primary Structure | Peptide Name | Amino Acids | Molecular Weight | Net Charge |
| --- | --- | --- | --- | --- |
| KAQKA QAKQA KQAQK AQKAQ AKQAK Q (SEQ ID NO: 1) | p5 | 31 | 3303.7 | +8 |
| KAQKA QAKQA KQAQK AQKAQ AKQAK QAQHE DT (SEQ ID NO: 26) | p75 | 37 | 3939.7 | +6 |
| KAQKA QAKQA KQAQK AQKAQ AKQAK QGGGH EDT (SEQ ID NO: 27) | p76 | 38 | 3911.6 | +6 |
| KAQKA QAKQA KQAQK AQKAQ AKQAK QGPGH EDT (SEQ ID NO: 28) | p77 | 38 | 3951.7 | +6 |
| KAQKA QAKQA KQAQK AQKAQ AKQAK QVTVH EDT (SEQ ID NO: 29) | p78 | 38 | 4039.8 | +6 |

We have previously demonstrated, by alanine-scanning, the importance of the aspartate (D) and glutamate (E) side chains, as well as the presence of the terminal carboxylate moiety for 7D8 binding. The 7D8 mAb was shown to bind not only AA amyloid, but also human ALκ and ALλ amyloids by virtue of a cryptic -ED- epitope in the light chain variable domain sequence at position ~84 and 85.

Peptide p5 is a 31 amino acid, synthetic, heparin-binding peptide with a +8 net charge that has been shown to bind AA amyloid quantitatively in vivo using the H2/IL-6 murine model of systemic amyloidosis. Furthermore, a radio-iodinated variant has been shown to bind to Aβ amyloid deposits in the cerebrovasculature of TG2576 mice. Additionally, using biotinylated p5 we have demonstrated reactivity with human ALκ, ALλ, ATTR, AA and AIAPP in formalin-fixed tissue sections.

ELISA Binding Studies

Figure 20A:
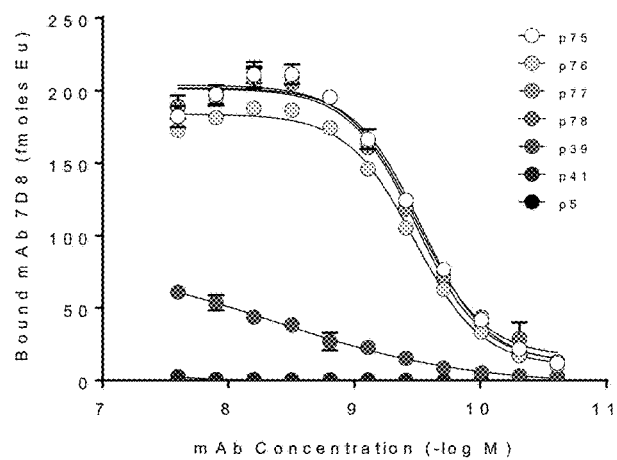
FIGS. 20A-20B are a pair of graphs showing 7D8 antibody binding to all peptopes (FIG. 20A) and biotinyl-7D8 antibodies binding to all peptopes (FIG. 20B) dried on the surface of microplates and assayed by ELISA, in accordance with certain example embodiments. The EC50 for 7D8 was ~0.3 nM for all peptopes and there was no significant difference between the binding of 7D8 with the different peptopes. Thus, the nature of the spacer amino acid sequence introduced between the p5 and epitope did not influence mAb binding to the peptope. When biotinylated mAb 7D8 was evaluated, similar reactivity was observed; however, the EC50 in these assays for all peptopes was ~1 nM. In both assays, no binding to the p5 peptide sequence lacking the epitope, was observed.
Figure 20B:
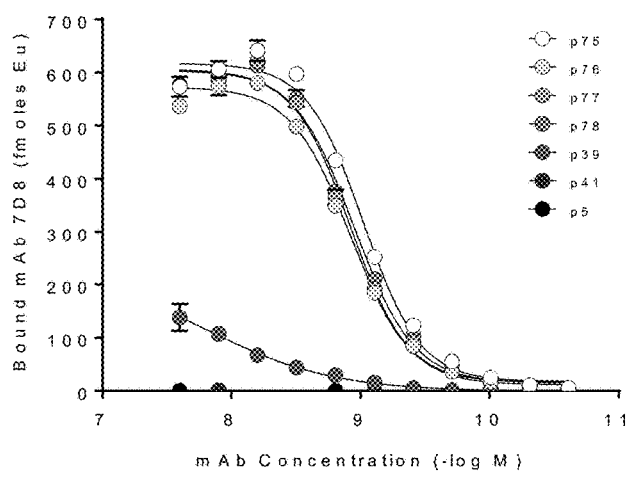

Peptides (p75-78 and control reagents; peptide 39 [CG-GHEDT] (SEQ ID NO: 54), peptide 41 [CGGHEDT-MADQE] (SEQ ID NO: 55) and peptide p5 (SEQ ID NO: 1), were prepared at 1 µg/ml in PBS and 50 µl was added to each well of 1 96-well microplate (Costar EIA/RIA high binding). The peptides were dried onto the well at 37° C. overnight. Sample wells were blocked for 1 h by addition of 200 µL of 1% BSA in PBS. Primary antibodies (7D8 or biotinylated 7D8) and secondary antibodies (biotinylated goat anti mouse) were added in 100 µL of a diluent of 1% BSA and 0.05% tween 20 in PBS. The 7D8 primary antibody was tested with a 1:2 dilution series beginning at 50 nM. A 1/3000 dilution of the secondary biotinylated goat anti-mouse IgG antibody (Sigma) was added for 1 h and the microplate washed. When the biotinylated 7D8 mAb was used the secondary antibody step was omitted. Binding was visualized by addition of a 1/1000 dilution of europium/streptavidin (Perkin Elmer) for 1 h and developed with enhancement solution (Perkin Elmer) before quantifying the signal using a time-resolved fluorescence plate reader (Wallac). Results of the ELISA experiments are shown in FIGS. 20A-20B.

Surface Plasma Resonance

Analyses were performed using a BIAcore X surface plasmon resonance instrument (GE Healthcare) and all reagents were obtained from GE Healthcare. For chip preparation, the peptides were attached to CM-5 chips using the amino-coupling method supplied with the instrument software. Briefly, chips were activated by injection (35 μL) of a mixture of ECD/NHS at a flow rate of 5 μL/min. Immediately thereafter, 35 μL of the test peptide (peptope p75, p76, p77, or p78), diluted to 1 μg/mL in NaOAc buffer, pH 5.5, was injected. After peptide coupling, the remaining active groups on the chip were blocked by injection of 35 μL of 1 M ethanolamine-HCl pH 8.5. Test peptides p75, p76, p77, or p78 were coupled to the Fc-1 channel and peptide p5, which served as a control, was coupled to the Fc-2 channel. A sensorgram was initiated on each chip in HBS-EP buffer at 10 μL per min. An initial regeneration step consisting of a 20 μL injection of pH 2.5 glycine buffer was performed and the baseline allowed to equilibrate. Antibody 7D8 was diluted to a stock of 10 μg/mL in HBS-EP buffer which was further diluted to a 0.4 μg/mL (~2.7 nM) working dilution immediately before injection. The antibody was injected (50 μL) and the data collected for 200 seconds using a delayed wash cycle. The chip was subjected to a regeneration step before the next test injection. Binding data were extracted from the sensorgram, aligned, and analyzed using the BIAevaluation software by fitting to the following binding models (i) Langmuir, (ii) Langmuir with mass transfer, and (iii) Interaction of a bivalent analyte [A+B→AB; AB+B→$AB_2$].

Binding data for mAb 7D8 binding to amino-coupled peptopes by using surface plasmon resonance (SPR) is shown in FIGS. 21A-21D. We anticipate that the coupling of the peptopes to the SPR chip via the lysine sidechains is analogous to how the peptope will engage with amyloid fibrils and amyloid-associated hypersulfated heparan sulfate. Thus, the availability of the 7D8 epitope sequence is likely to be similar to that seen in the amyloid bound peptope.

Using this technique the 7D8 was shown to bind to all peptopes. Based on the "shape" of the sensogram it is evident that 7D8 binds peptopes p75 and p77 with a similar kinetic profile. (FIGS. 21A and 21B). Also, p76 and p78 appear to have similar kinetic binding profiles (FIGS. 21C and 21D). These differences could be due to small inconsistencies in the amount of peptide bound to the flow cell during chip preparation. The absolute amount of peptide bound is difficult to control or to quantitate.

Kinetic analysis of the binding data (shown in Table 7 below), indicated that the "Langmuir binding with mass transfer" analysis provided the best fit, based on $Chi^2$ statistical calculations. These analyses revealed very similar dissociation constants (KD) for all peptopes, i.e., 1.5-3 nM, which is consistent with the $EC_{50}$ estimations based on the ELISA data.

TABLE 7

Langmuir

| | ka (1/Ms) | kd (1/s) | Rmax (RU) | RI (RU) | Conc of analyte | KA (1/M) | KD (M) | Req (RU) | kobs (1/s) | Chi2 |
|---|---|---|---|---|---|---|---|---|---|---|
| p75 | 3.69E+05 | 2.33E−03 | 2.18E+03 | 17.4 | 2.7 nM | 1.59E+08 | 6.30E−09 | 654 | 3.33E−03 | 6.61 |
| p76 | 2.95E+06 | 6.67E−03 | 351 | 28 | 2.7 nM | 4.43E+08 | 2.26E−09 | 191 | 0.0146 | 20.6 |
| p77 | 5.19E+04 | 4.98E−03 | 8.16E+03 | 12 | 2.7 nM | 1.04E+07 | 9.60E−08 | 223 | 5.12E−03 | 6.86 |
| p78 | 2.42E+06 | 5.98E−03 | 633 | 18.9 | 2.7 nM | 4.05E+08 | 2.47E−09 | 331 | 0.0125 | 63.5 |

Langmuir with Mass Transfer

| | ka (1/Ms) | kd (1/s) | Rmax (RU) | kt (RU/(M*s)) | RI (RU) | Conc of analyte | KA (1/M) | KD (M) | Req (RU) | kobs (1/s) | Chi2 |
|---|---|---|---|---|---|---|---|---|---|---|---|
| p75 | 5.95E+06 | 8.53E−03 | 765 | 9.14E+08 | 16.2 | 2.7 nM | 6.98E+08 | 1.43E−09 | 500 | 0.0246 | 0.287 |
| p76 | 8.96E+06 | 0.0137 | 302 | 1.43E+09 | 23.3 | 2.7 nM | 6.33E+08 | 1.58E−09 | 191 | 0.0372 | 11.8 |
| p77 | 1.96E+08 | 0.653 | 429 | 4.57E+08 | 1.38 | 2.7 nM | 3.00E+08 | 3.33E−09 | 192 | 1.18 | 2.41 |
| p78 | 1.29E+07 | 0.0188 | 502 | 1.65E+09 | 11 | 2.7 nM | 6.85E+08 | 1.46E−09 | 326 | 0.0536 | 15.9 |

Bivalent Analyte

| | ka1 (1/Ms) | kd1 (1/s) | ka2 (1/RUs) | kd2 (1/s) | Rmax (RU) | RI (RU) | Conc of analyte | Chi2 |
|---|---|---|---|---|---|---|---|---|
| p75 | 8.53E+04 | 0.0674 | 8.22E−04 | 0.0628 | 4.79E+03 | 6.56 | 2.7 nM | 9.11 |
| p76 | 6.09E+05 | 0.0736 | 2.38E−03 | 0.0774 | 861 | 22.4 | 2.7 nM | 11 |
| p77 | 4.46E+04 | 0.0295 | 3.76E−05 | 0.0224 | 5.43E+03 | 9.36 | 2.7 nM | 6.43 |
| p78 | 6.37E+04 | 9.72E−03 | 1.10E−07 | 2.63E−05 | 9.16E+03 | 40 | 2.7 nM | 132 |

Discussion

The mAb 7D8 binds all peptope sequences as evidenced by using ELISA and SPR techniques. Binding is independent of the nature of the spacer sequence used in the peptope. The affinity of the interaction was ~1 nM as estimated from $EC_{50}$ measurements (from FIGS. 20A-20B) or from fitting the kinetic binding data (Table 7). We have shown that the integrity of the -HEDT- epitope (SEQ ID NO: 52) remains intact and available when fused to the polybasic amyloid-targeting p5 sequence. This indicates that the acidic glutamate and aspartate residues within the epitope, which are critical for 7D8 binding, are not sequestered by the numerous basic lysyl side chain moieties of p5, which are critical for amyloid binding. The short 3-amino acid spacer likely prevents this interaction, regardless of whether the spacer design incorporates helical (p75), random coil (p76), restrained coil (p77), or extended sheet (p78) amino acid sequences.

Example 6—Reactivity of mAb 7D8, in the Presence or Absence of Peptope, with Synthetic Amyloid Fibrils and Human Amyloid Extracts The four peptope sequences shown above in Table 6, based on the peptide p5 and the -HEDT- epitope (SEQ ID NO: 52), were used in this study. Peptide p5 was used as the amyloid reactive peptide sequence. All peptides were synthesized and purified by reverse phase (RP) HPLC as described in Example 5, above.

Radiolabeling of mAb 7D8

The 7D8 antibody (15 µg) was radiolabeled with 0.5 mCi of reductant-free iodine-125 ($^{125}$I, Perkin Elmer) using limiting amounts of chloramine T (10 µg) and suspended in PBS containing 0.1% gelatin as carrier protein. Unbound radioisotope and protein aggregates were removed from the preparation by size-exclusion liquid chromatography using an Ultrogel AcA34 solid phase (Amersham Pharmacia). Fractions containing $^{125}$I-7D8 were pooled for pull-down assays. The relative radiopurity of the preparation was assessed by SDS/PAGE (4-12% acrylamide; Novex) followed by imaging using a phosphor-imager (Cyclone).

Pulldown Assays

Pulldown assays were performed using $^{125}$I-7D8 using, as a substrate, peptope-conjugated to polystyrene beads, synthetic fibrils (Aβ[1-40] or IAPP) or human ATTR amyloid extracts (transthyretin-associated amyloid [ATTR] was previously isolated from the organs of three different patients with Appalachian mutation—Thr60Ala). To assess reactivity of the $^{125}$I-7D8 mAb with each of the four peptopes in "solution", each was conjugated to amino-derivatized polystyrene beads via a glutaraldehyde cross-linker between the ε-amino groups of the lysine residues in the p5 region of the peptope. The Schiff base bonds were stabilized with cyanoborohydride. Presentation of the epitope in this way would mimic the amyloid-bound peptope, with the p5 moiety involved in the binding, leaving the epitope adjacent to a solid surface but free for antibody interactions. For the bead pulldown, $^{125}$I-7D8 (~0.065 nM final concentration) was added to 10 µL of bead preparation in a 200 µL volume of PBS with 0.05% Tween 20 (PBST). The sample was mixed end over end for 1 h at room temperature, and the bound and free $^{125}$I-7D8 were then separated by serial centrifugations at 16,000×g and the percent bound calculated $$\text{immunoreactivity} = [\text{bound}_{cpm}/(\text{bound}_{cpm} + \text{free}_{cpm})] \times 100$$

Pulldown assays using synthetic fibrils and amyloid extracts were performed essentially as described herein. However, in these assays, 50 µg of amyloid extract or 25 µg of synthetic fibrils were pre-incubated with unlabeled peptope (65 nM) for 1 h at room temperature with mixing. The free peptope was removed by centrifugation before addition of 0.065 nM $^{125}$I-7D8 and further incubation as described for the bead assay pulldown.

EuLISA Assay

The binding of biotinylated 7D8 with synthetic fibrils and human ATTR amyloid extract was assessed in the presence or absence of each peptope by using EuLISA. In these assays, fibrils or amyloid extracts were coated onto EIA/RIA high-binding microplates (Costar) at 10 µg/mL, 50 µL per well. The samples were dried overnight at 37° C. and then washed with PBST and blocked using 200 µL/well of 1% BSA/PBS for 1 h at 37° C. Each of the four peptopes was added to the wells at 5 µM and incubated for 1 h at 37° C. After aspiration and one wash with PBST, 50 µL of biotinylated-7D8 was added into the sample wells covering a concentration of ~0.1-600 nM. After a 1 h incubation, the plates were washed with PBST and a 1:1000 dilution of streptavidin-conjugated europium (Perkin Elmer) added for 1 h at 37° C. Immunoreactivity was demonstrated by addition of enhancement solution (Perkin Elmer) and measurement of the time-resolved fluorescence emission (Wallac Victor3 1420 Multilabel plate reader). Control wells included fibril-coated, BSA-blocked wells without peptope. Antibody binding data are presented as titrations of each sample and after subtraction of the background (signal from the no-peptope wells).

Immunohistochemistry

The binding of biotinylated 7D8 mAb with autopsy-derived, formalin-fixed, paraffin-embedded tissue sections containing, ATTR, ALκ or ALλ was assessed immunohistochemically. Consecutive tissue sections were stained with: Congo red; biotinylated 7D8 alone; 7D8 with the control peptide p5; or, 7D8 mAb with peptope p75 pretreatment. Briefly, six µm-thick tissue sections were subjected to antigen retrieval by incubation in CitraPlus solution (BioGenex, San Ramon, Calif.) for 30 min at 90° C. Unlabeled peptope p75 was added to the tissue at ~3 µg/mL and incubated overnight at 4° C. Unbound reagent was removed by washing in PBST for 30 min. Tissues sections (with or without peptope pretreatment) were immunostained by addition of 3 µg/mL biotinylated 7D8 mAb. Slides were developed by addition of streptavidin-HRP (Vectastain Elite ABC kit, Vector Labs) followed by 3,3'-diaminobezidene (Vector Labs) and examined using a Leica DM500 microscope.

Phagocytosis Assay

The phagocytosis of human cardiac ATTR extract induced by peptope and 7D8 was studied using a pH-sensitive fluorescence enhancement assay. The RAW 264.7 murine macrophages (1×10$^6$ cells per well) were plated into the wells of a 12-well culture dish, containing a glass coverslip, and incubated at 37° C. overnight. On the day of the experiment, 10 µg of pHrodo green-labeled human ATTR extract was mixed with 4 µg of p75 peptope or, as a negative control, an equal volume of PBS (pHrodo green [Thermofisher, Molecular Probes] is a pH sensitive dye that is only fluorescent at pH 4, i.e. in a acidified macrophage endosome/lysosome). The sample was incubated for 30 min. Unbound p75 peptope was removed by washing twice, by centrifugation at 10,000×g using PBS. The 7D8 and MOPC mAb solutions (MOPC served as a negative isotype control) were centrifuged at 10,000×g to remove particulates before adding 10 µg to the peptide-coated ATTR extract. The samples were incubated for 1 h before being washed by centrifugation as above, before being added to the wells of the microplate. The cells were incubated with the amyloid extract for 80 min, at which time Hoescht dye (Thermofisher) was added to the well (to stain the cell nuclei blue), and the mixture incubated for a further 10 min. The coverslips were then washed and mounted on a slide for epifluorescent microscopy and digital image acquisition using blue (nuclei) and green (phagocytosed amyloid) fluorescent filters. Images (original magnification 160×) were analyzed digitally and the area of green fluorescence per cell ("phagocytosis index") was calculated using 3 or 4 digital images acquired from each coverslip. Approximately 2000 cells were analyzed for each sample. Images were also taken at a magnification of 320× to demonstrate uptake of amyloid in individual cells.

Results

Pulldown Assays

Figure 22:
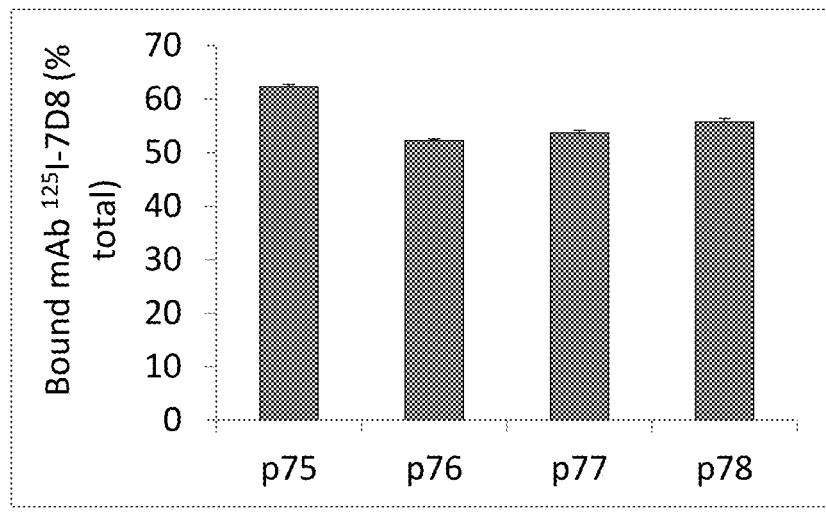
FIG. 22 is a graph showing a pulldown assay using $^{125}$I-labeled mAb 7D8 and peptide-coated beads as the substrate, in accordance with certain example embodiments. The reactivity of radioiodinated mAb 7DB with the epitope when the peptide is bound to a solid matrix, approximating the amyloid-bound state, is shown. The data suggest that peptope p75, with the helical -QAQ- spacer, may provide marginally better binding of the 7D8 mAb, as compared to the other reagents (p76, p 77, and p78).

Polystyrene beads coated with each of the peptopes were used to study the reactivity of radioiodinated mAb 7D8 with the epitope when the peptope is bound to a solid matrix, approximating the amyloid-bound state (FIG. 22). The mAb bound well, 50-60% of added $^{125}$I-7D8, with all peptopes. The data suggest that peptope p75 (62.3%), with the helical -QAQ- spacer, may provide marginally better binding of the 7D8 mAb, as compared to the other reagents (52%, 53%, and 55% bound peptide).

Figure 23:
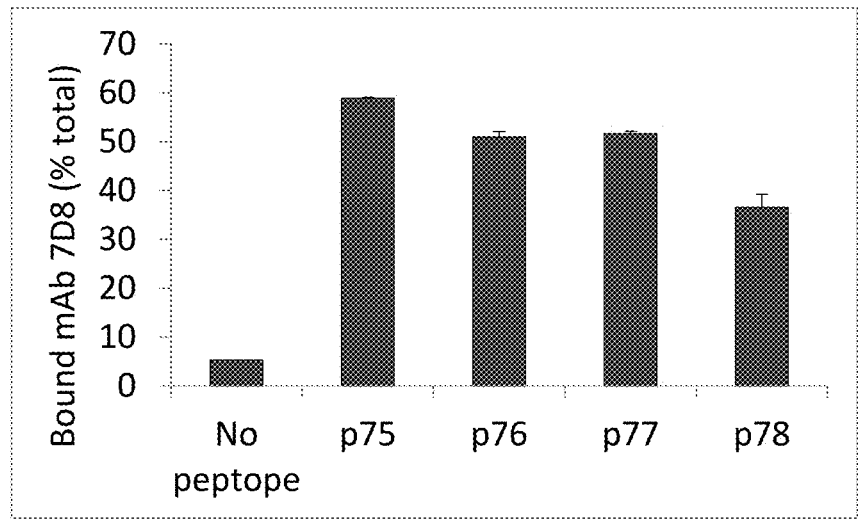
FIG. 23 is a graph showing a pulldown assay with Aβ(1-40) fibrils as the substrate, in accordance with certain example embodiments. As shown, treatment of the fibrils with peptide p75 afforded the best binding of $^{125}$I-7D8.

Pulldown binding assays were then performed using Aβ(1-40) fibrils as the substrate (FIG. 23). In this assay, $^{125}$I-7D8 did not bind the fibrils in the absence of peptope pre-labeling (5.3% bound mAb). In contrast, there was a 7- to 11-fold increase in the binding of $^{125}$I-7D8 when the fibrils had been pre-incubated with the peptope sequences. Again, in this assay, treatment of the fibrils with peptope p75 afforded the best binding of $^{125}$I-7D8 (58.9% bound mAb).

Figure 24:
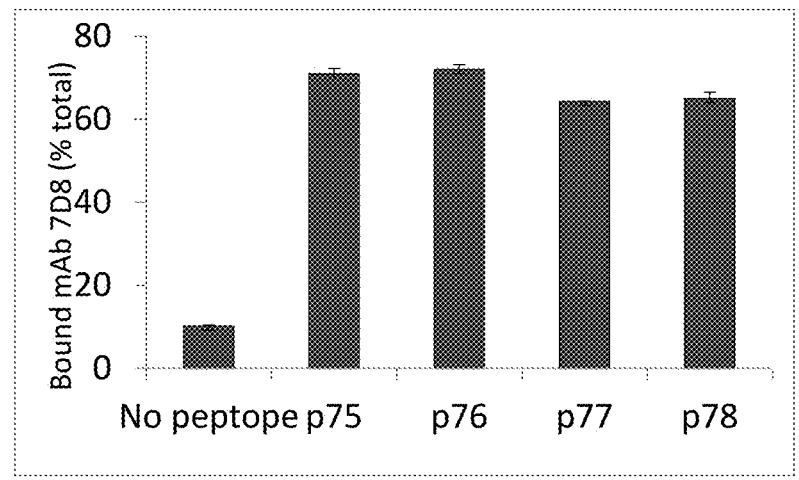
FIG. 24 is a graph showing a pulldown assay with synthetic IAPP fibrils as the substrate, in accordance with certain example embodiments. As shown, treatment of the IAPP fibrils with peptide p75 afforded the best binding of $^{125}$I-7D8. Binding of $^{125}$I-7D8 with synthetic fibrils composed of IAPP or Aβ(1-40) was low without peptide addition. But when the fibrils were pre-targeted with the peptide sequences, particularly p75, the reactivity of the mAb was increased substantially (approximately 7-fold).
Figure 25:
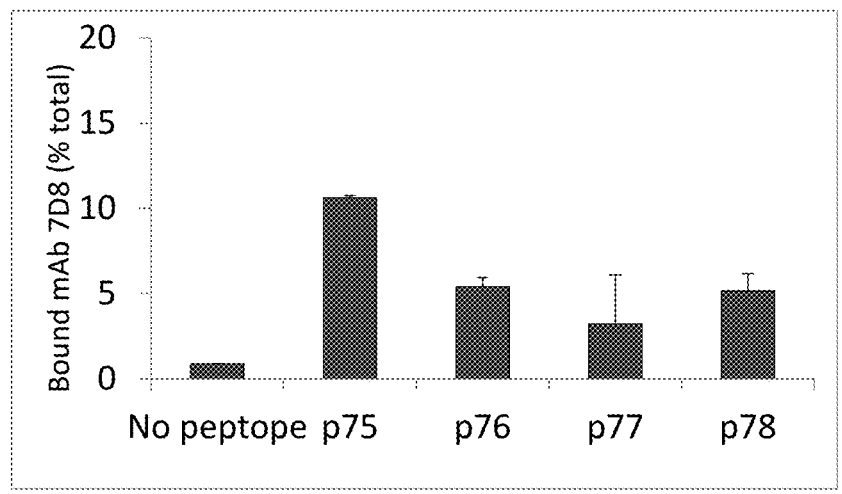
FIG. 25 is a graph showing a pulldown assay using patient Sno ATTR extract (transthyretin-associated heart amyloid) as the substrate, in accordance with certain example embodiments. Using ATTR extract from patient Sno, the $^{125}$I-7D8 mAb did not bind significantly to the extract (0.9% bound). In contrast, pre-treatment with peptide, notably p75, resulted in 10-fold increase in the binding of 7D8.
Figure 26:
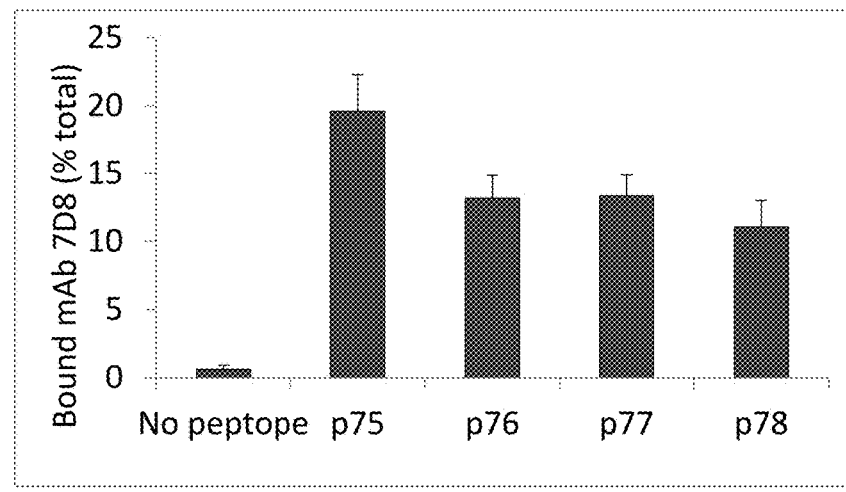
FIG. 26 is a graph showing a pulldown assay with patient Gre ATTR extract, in accordance with certain example embodiments. Binding was higher than that seen for the Sno ATTR extract but peptope p75 (approximately a 30-fold increase in binding) was the most effective reagent in this assay also.

Similar data were obtained when IAPP fibrils were used as the target (FIG. 24). Interestingly, the $^{125}$I-7D8 mAb exhibited higher non-specific interactions with the IAPP fibrils alone (10%) as compared to the Aβ(1-40) aggregates. However, upon pre-treatment of the IAPP fibrils with each of the peptopes there was a ~7-fold increase in the amount of mAb bound. The binding of $^{125}$I-7D8 with synthetic fibrils composed of IAPP or Aβ(1-40) was low without peptope addition; however, when the fibrils were pre-targeted with the peptope sequences, particularly p75, the reactivity of the mAb was increased 7-10 fold. These data indicate that not only is the 7D8 epitope available for effective binding of the mAb, but also that the p5 peptide moiety still retains pan-amyloid binding capabilities when synthesized as a bifunctional peptide containing the epitope sequence.

Since ATTR is the most common systemic amyloid that is not naturally bound by the 7D8 mAb we performed pulldown assays using human ATTR amyloid extract from 3 different patients (all with the Appalachian mutation). Using a ATTR extract from the heart of patient Sno (FIG. 25), the $^{125}$I-7D8 mAb did not bind significantly to the extract alone (0.9% bound). In contrast, pre-treatment with peptope, notably p75, resulted in a 5- to 10-fold increase in the binding; however the maximal binding was significantly lower than that seen using the same mass of synthetic fibrils (see above). This is likely due to the fact that per unit mass there is significantly less thioflavin T (ThT)-positive material. i.e., amyloid fibrils—ThT binding is a measure of the amount of fibrils in a preparation. Additionally, we recently have shown that the optimal ATTR extract-binding peptide is not p5 (used in these peptopes) but, rather, the p5+14 peptide. Therefore, the reactivity of peptope could be optimized and enhanced specifically to facilitate mAbs 2A4, 7D8, or 8G9 binding to ATTR.

Figure 27:
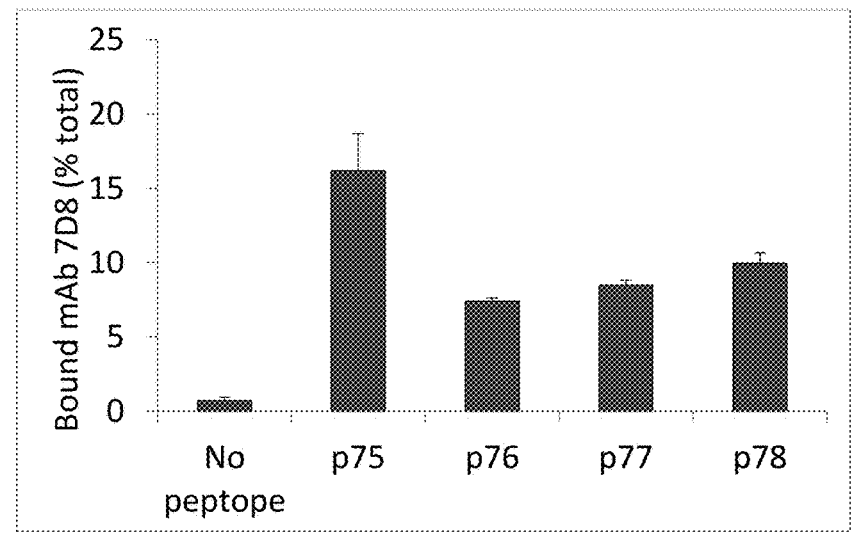
FIG. 27 is a graph showing a pulldown assay with patient Ken ATTR extract, in accordance with certain example embodiments. Binding was higher than that seen for the Sno ATTR extract but peptope p75 (approximately a 20-fold increase in binding) was the most effective reagent in this assay also.
Figure 28:
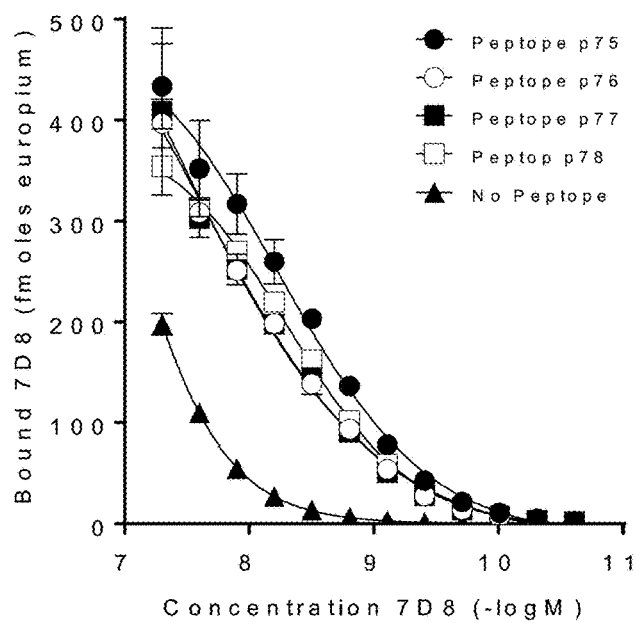
FIG. 28 is a graph showing binding of biotinyl-7D8 to Aβ(1-40) fibrils+/−peptope treatment, in accordance with certain example embodiments.

Similar data were obtained using ATTR from patients Gre (FIG. 26) and Ken (FIG. 27). Binding of $^{125}$I-7D8 to these extracts was higher than that seen for Sno (~15-20% bound mAb following pre-treatment with peptope p75), which likely reflects differences in the concentration and availability of the peptope binding ligands in the amyloid preparation, i.e., fibrils and heparan sulfate glycosaminoglycans. The p5 peptide has been shown to bind both heparin and synthetic amyloid fibrils; therefore, binding to amyloid extracts likely occurs via interactions with either the hypersulfated glycosaminoglycans or the amyloid fibrils, or both. The relative abundance of these components and their exposure in the amyloid preparations will invariably affect binding of the peptope.

EuLISA Assays

To generate a quantitative measure of the enhanced binding of mAb 7D8 to synthetic fibrils (FIGS. 28-31) and ATTR extracts (FIGS. 32-35), we performed a titration of biotinylated 7D8 on surface-adsorbed amyloid by using a EuLISA technique. In each case, data for the binding of biotinyl-7D8 is shown in the presence or absence (+/−) of each peptope, and the "No peptope" background signal was subtracted and the data replotted. All data were fit to a sigmoid equation.

Figure 29:
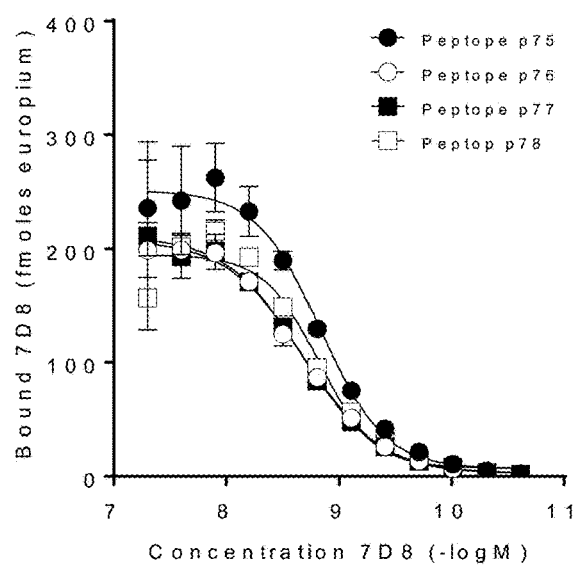
FIG. 29 is a graph showing control-adjusted binding of biotinyl-7D8 to peptope treated Aβ(1-40) fibrils (shown in FIG. 28), in accordance with certain example embodiments. The EC50 of mAb 7D8 for Aβ(1-40) fibrils in the presence of peptope p75 was estimated to be approximately 1 nM.
Figure 30:
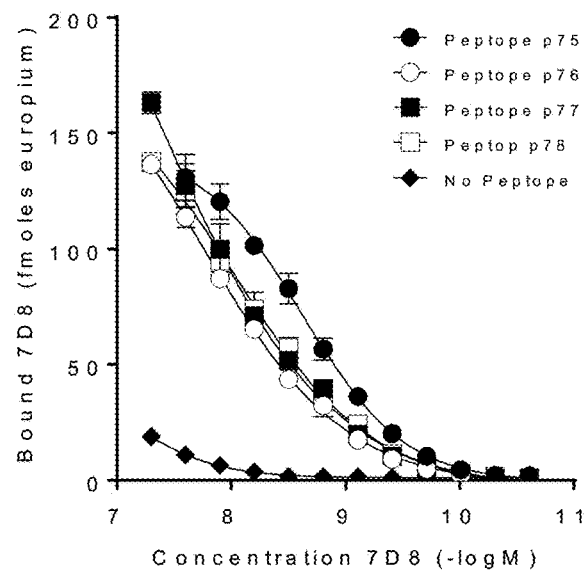
FIG. 30 is a graph showing binding of biotinyl-7D8 to IAPP fibrils+/−peptope treatment, in accordance with certain example embodiments.
Figure 31:
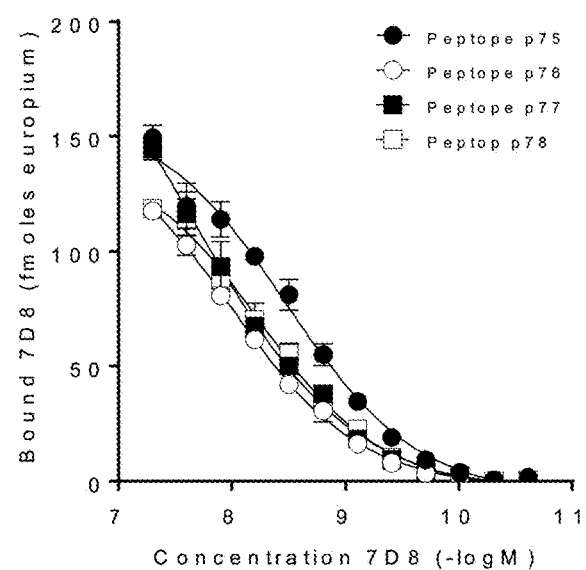
FIG. 31 is a graph showing control-adjusted binding of biotinyl-7D8 to peptope treated IAPP fibrils (shown in FIG. 30), in accordance with certain example embodiments. The EC50 of mAb 7D8 for IAPP fibrils in the presence of peptope p75 was estimated to be approximately 6 nM.
Figure 32:
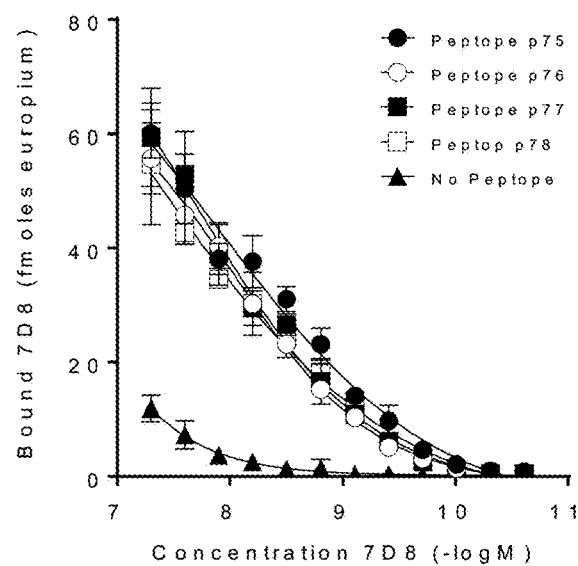
FIG. 32 is a graph showing binding of biotinyl-7D8 to Sno ATTR extract+/−peptope treatment, in accordance with certain example embodiments.
Figure 33:
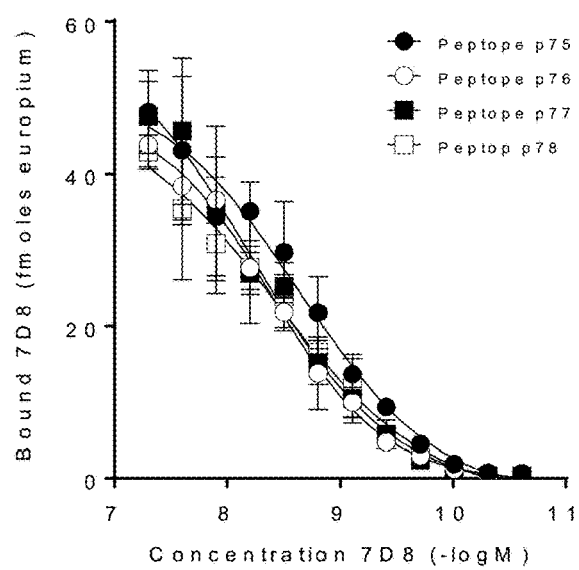
FIG. 33 is a graph showing control-adjusted binding of biotinyl-7D8 to peptope treated Sno ATTR extract (shown in FIG. 32), in accordance with certain example embodiments. The EC50 of mAb 7D8 for human Sno ATTR amyloid extract in the presence of peptope p75 was estimated to be approximately 5 nM.
Figure 34:
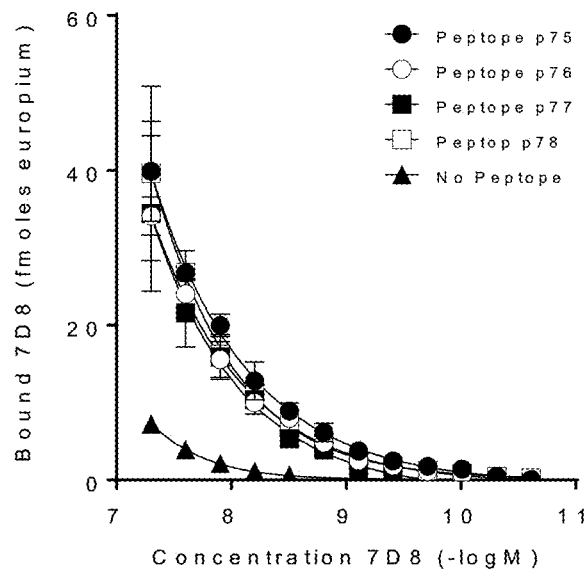
FIG. 34 is a graph showing binding of biotinyl-7D8 to human Gre ATTR amyloid extract+/−peptope treatment, in accordance with certain example embodiments.
Figure 35:
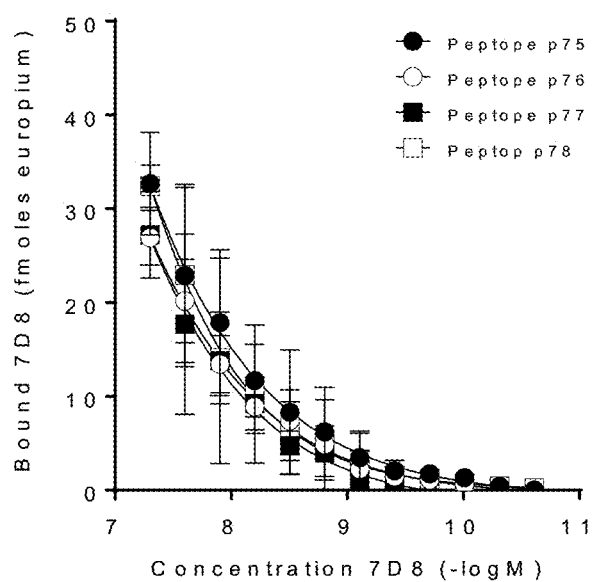
FIG. 35 is a graph showing control-adjusted binding of biotinyl-7D8 to peptope treated human Gre ATTR amyloid extract, in accordance with certain example embodiments.
Figure 36A:
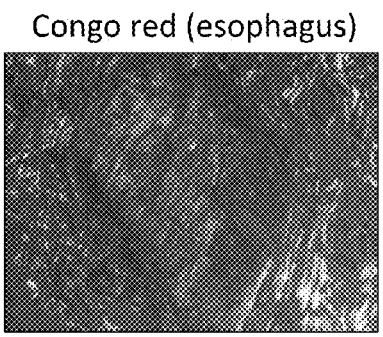
FIGS. 36A-36D are a series of micrographs showing immunohistochemical evaluation of biotinyl-7D8 binding to formalin-fixed tissues section (esophagus) containing human Gre ATTR amyloid, in accordance with certain example embodiments. Congo red staining (FIG. 36A) was used to show the presence of amyloid in the tissue. Consecutive sections were stained with mAb 7D8 alone ("7D8 IHC") (FIG. 36B), mAb 7D8 with a negative control peptide ("Ctrl peptide p5+7D8 IHC") (FIG. 36C), or with peptope p75 followed by 7D8 ("Peptope p75+7D8 IHC") (FIG. 36D). Specific positive staining of the ATTR amyloid was only achieved with the peptope p75 and 7D8 mAb.
Figure 36B:
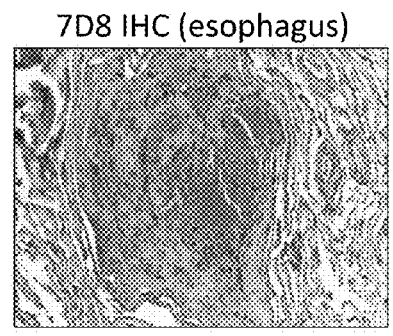
Figure 36C:
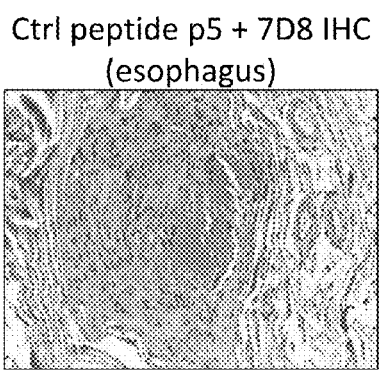
Figure 36D:
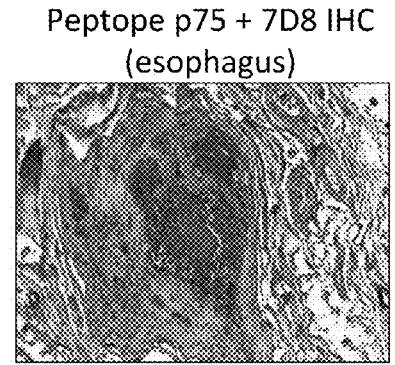
Figure 37A:
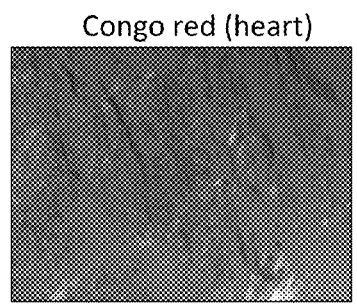
FIGS. 37A-37D are a series of micrographs showing immunohistochemical evaluation of biotinyl-7D8 binding to formalin-fixed tissues section (heart) containing human Gre ATTR amyloid, in accordance with certain example embodiments. Congo red staining (FIG. 37A) was used to show the presence of amyloid in the tissue. Consecutive sections were stained with mAb 7D8 alone ("7D8 IHC") (FIG. 37B), mAb 7D8 with a negative control peptide ("Ctrl peptide p5+7D8 IHC") (FIG. 37C), or with peptope p75 followed by 7D8 ("Peptope p75+7D8 IHC") (FIG. 37D). Specific positive staining of the ATTR amyloid was only achieved with the peptope p75 and 7D8 mAb.
Figure 37B:
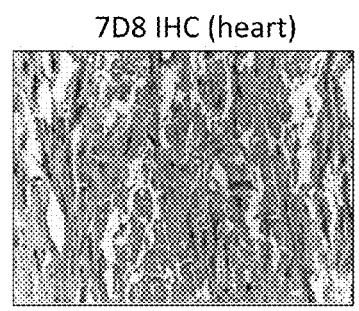
Figure 37C:
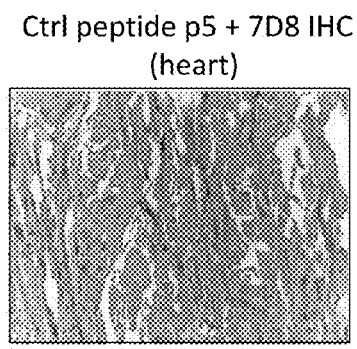
Figure 37D:
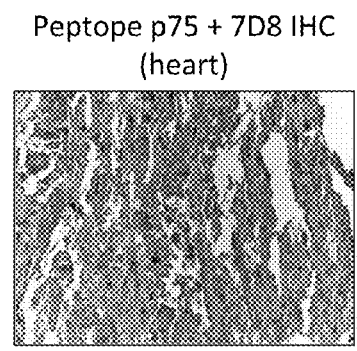
Figure 38A:
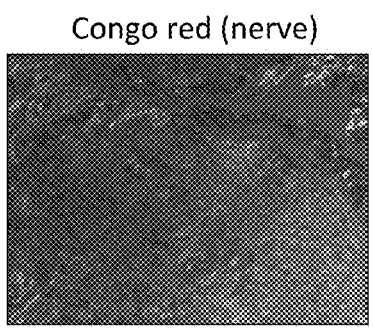
FIGS. 38A-38D are a series of micrographs showing immunohistochemical evaluation of biotinyl-7D8 binding to formalin-fixed tissues section (nerve) containing human Gre ATTR, in accordance with certain example embodiments. Congo red staining (FIG. 38A) was used to show the presence of amyloid in the tissue. Consecutive sections were stained with mAb 7D8 alone ("7D8 IHC") (FIG. 38B), mAb 7D8 with a negative control peptide ("Ctrl peptide p5+7D8 IHC") (FIG. 38C), or with peptope p75 followed by 7D8 ("Peptope p75+7D8 IHC") (FIG. 38D). Specific positive staining of the ATTR amyloid was only achieved with the peptope p75 and 7D8 mAb.
Figure 38B:
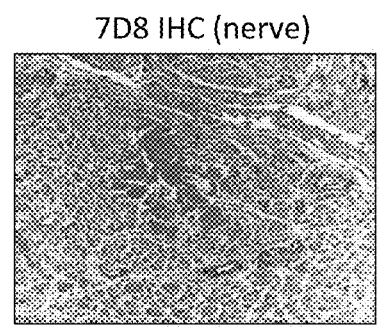
Figure 38C:
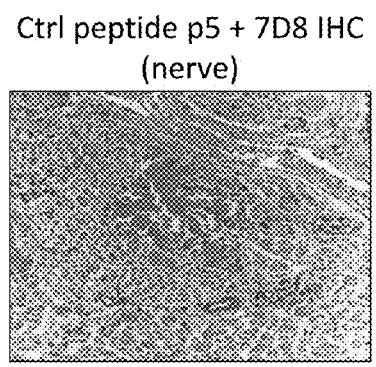
Figure 38D:
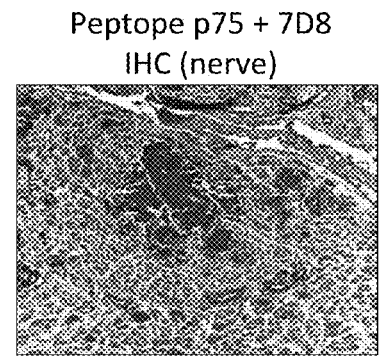
Figure 39A:
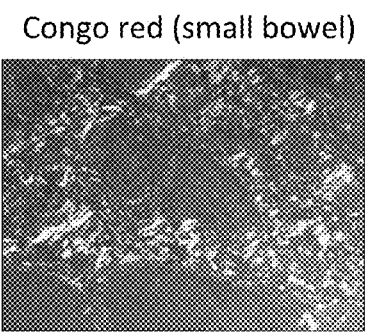
FIGS. 39A-39D are a series of micrographs showing immunohistochemical evaluation of biotinyl-7D8 binding to formalin-fixed tissues section (small bowel) containing human Gre ATTR, in accordance with certain example embodiments. Congo red staining (FIG. 39A) was used to show the presence of amyloid in the tissue. Consecutive sections were stained with mAb 7D8 alone ("7D8 IHC") (FIG. 39B), mAb 7D8 with a negative control peptide ("Ctrl peptide p5+7D8 IHC") (FIG. 39C), or with peptope p75 followed by 7D8 ("Peptope p75+7D8 IHC") (FIG. 39D). Specific positive staining of the ATTR amyloid was only achieved with the peptope p75 and 7D8 mAb.
Figure 39B:
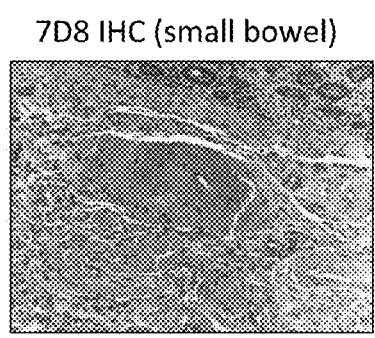
Figure 39C:
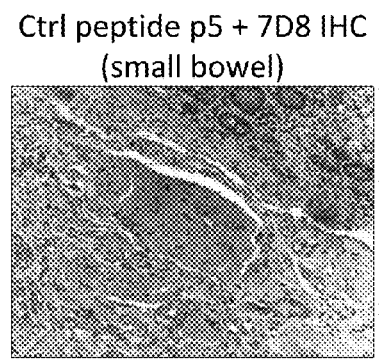
Figure 39D:
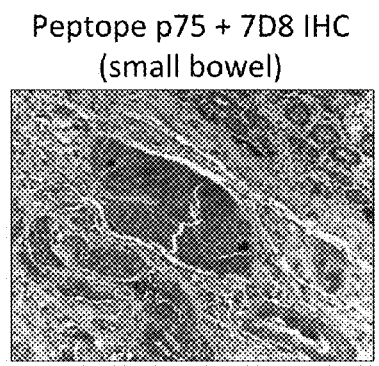
Figure 40A:
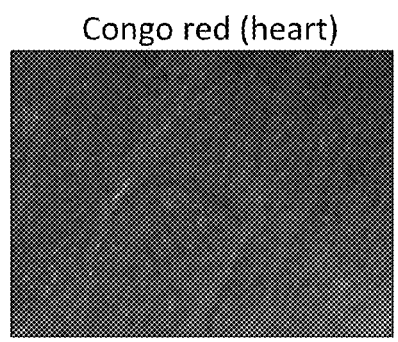
FIGS. 40A-40D are a series of micrographs showing immunohistochemical evaluation of biotinyl-7D8 binding to formalin-fixed tissues section (heart) containing human Ken ATTR, in accordance with certain example embodiments. Congo red staining (FIG. 40A) was used to show the presence of amyloid in the tissue. Consecutive sections were stained with mAb 7D8 alone ("7D8 IHC") (FIG. 40B), mAb 7D8 with a negative control peptide ("Ctrl peptide p5+7D8 IHC") (FIG. 40C), or with peptope p75 followed by 7D8 ("Peptope p75+7D8 IHC") (FIG. 40D). Specific positive staining of the ATTR amyloid was only achieved with the peptope p75 and 7D8 mAb.
Figure 40B:
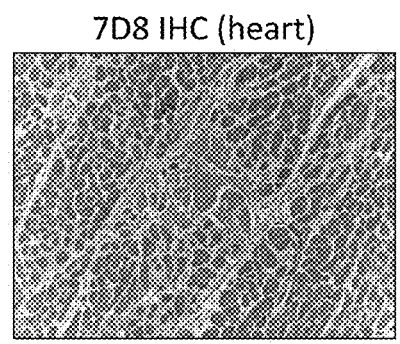
Figure 40C:
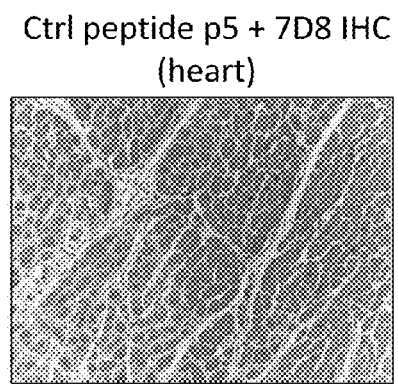
Figure 40D:
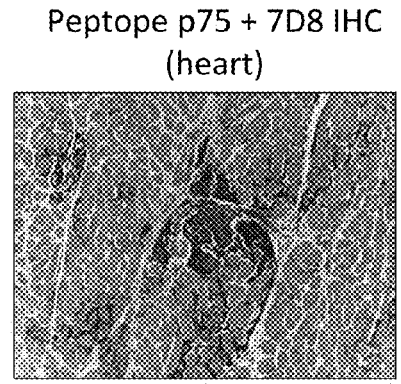
Figure 41A:
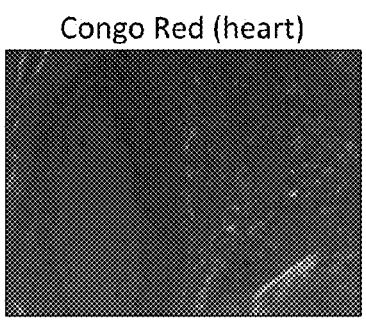
FIGS. 41A-41D are a series of micrographs showing immunohistochemical evaluation of biotinyl-7D8 binding to formalin-fixed tissues section (heart) containing human Sno ATTR, in accordance with certain example embodiments. Congo red staining (FIG. 41A) was used to show the presence of amyloid in the tissue. Consecutive sections were stained with mAb 7D8 alone ("7D8 IHC") (FIG. 41B), mAb 7D8 with a negative control peptide ("Ctrl peptide p5+7D8 IHC") (FIG. 41C), or with peptope p75 followed by 7D8 ("Peptope p75+7D8 IHC") (FIG. 41D). Specific positive staining of the ATTR amyloid was only achieved with the peptope p75 and 7D8 mAb.
Figure 41B:
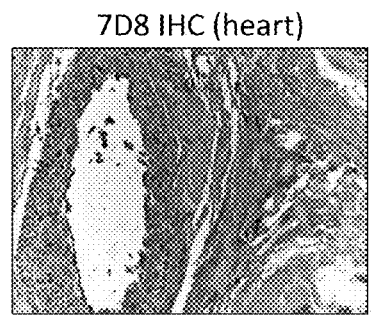
Figure 41C:
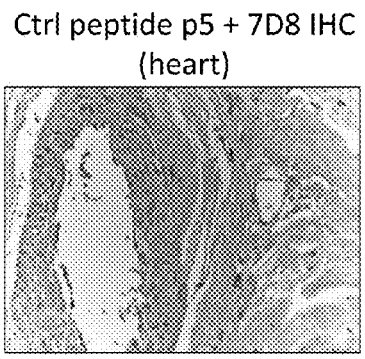
Figure 41D:
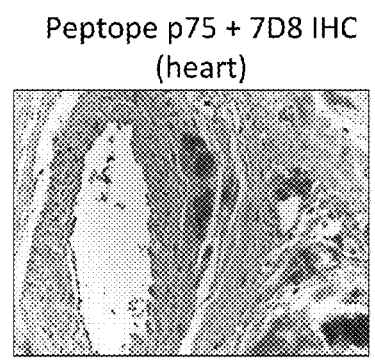
Figure 42A:
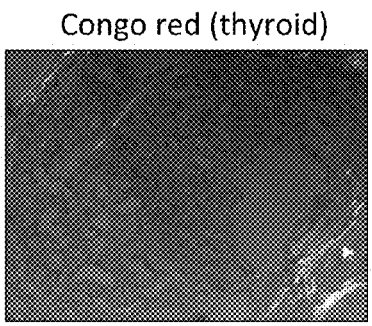
FIGS. 42A-42D are a series of micrographs showing immunohistochemical evaluation of biotinyl-7D8 binding to formalin-fixed tissues section (thyroid) containing human Den ALλ in accordance with certain example embodiments. Congo red staining (FIG. 42A) was used to show the presence of amyloid in the tissue. Consecutive sections were stained with mAb 7D8 alone ("7D8 IHC") (FIG. 42B), mAb 7D8 with a negative control peptide ("Ctrl peptide p5+7D8 IHC") (FIG. 42C), or with peptope p75 followed by 7D8 ("Peptope p75+7D8 IHC") (FIG. 42D). Specific positive staining of the ATTR amyloid was only achieved with the peptope p75 and 7D8 mAb.
Figure 42B:
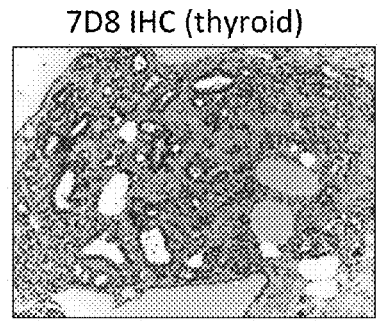
Figure 42C:
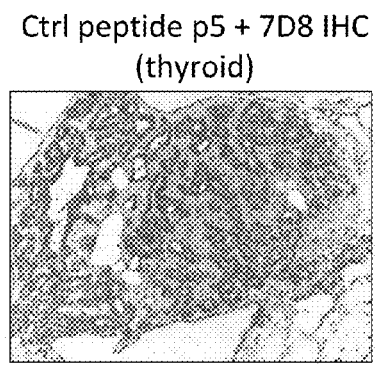
Figure 42D:
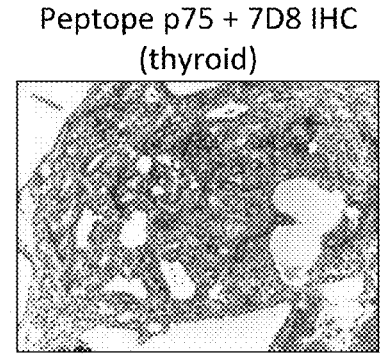
Figure 43A:
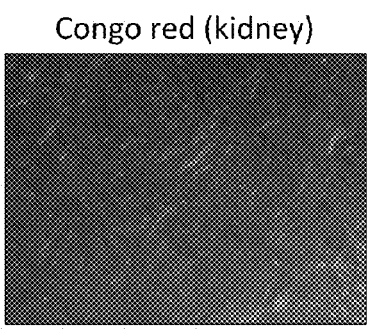
FIGS. 43A-43D are a series of micrographs showing immunohistochemical evaluation of biotinyl-7D8 binding to formalin-fixed tissues section (kidney) containing human Tal ALκ, in accordance with certain example embodiments. Congo red staining (FIG. 43A) was used to show the presence of amyloid in the tissue. Consecutive sections were stained with mAb 7D8 alone ("7D8 IHC") (FIG. 43B), mAb 7D8 with a negative control peptide ("Ctrl peptide p5+7D8 IHC") (FIG. 43C), or with peptope p75 followed by 7D8 ("Peptope p75+7D8 IHC") (FIG. 43D). Specific positive staining of the ATTR amyloid was only achieved with the peptope p75 and 7D8 mAb.
Figure 43B:
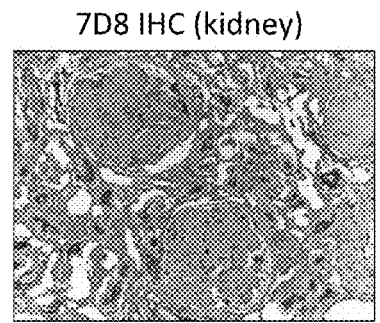
Figure 43C:
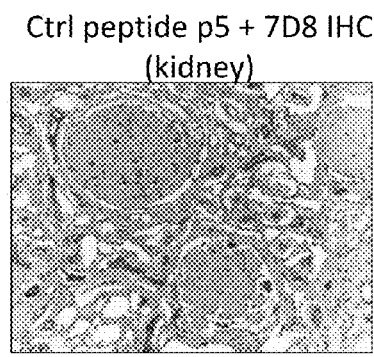
Figure 43D:
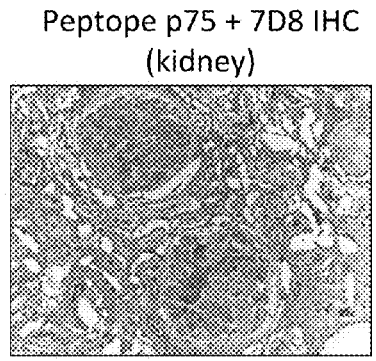

Binding of 7D8 mAb to Aβ(1-40) fibrils in the absence of peptope (FIG. 28; ▲) occurred only at high concentrations of mAb (>10 nM); however, after pre-targeting with peptopes, binding was observed at lower concentrations of mAb, with an estimated $EC_{50}$ (50% binding in the control adjusted data) of ~1-3 nM (FIG. 29). This $EC_{50}$ is approximately equal to the binding of 7D8 (and 2A4) to the -HEDT-COOH peptide ("HEDT" disclosed as SEQ ID NO: 52). As above, there is evidence from these data that peptope p75 is the most efficacious, but not significantly so, in this assay system.

Analysis of IAPP fibrils coated on the microplate wells yielded similar, but more dramatic, results (FIGS. 30 and 31), since the non-specific reactivity of 7D8 with untreated fibrils (FIG. 30; ♦) was less than that seen for Aβ(1-40) fibrils. The binding of biotinyl-7D8 to synthetic IAPP fibrils resulted in an $EC_{50}$ of ~6 nM, which is estimated to be more than 3 orders of magnitude better than that for the association of 7D8 with non-targeted IAPP fibrils.

Therefore, consistent with our pulldown data, pre-targeting of synthetic Aβ(1-40) and IAPP fibrils with peptopes enhanced the reactivity of the 7D8 mAb with these aggregates and resulted in approximately nanomolar $EC_{50}$ values, which is ~100-1000 fold more impressive than the "non-specific" interaction of mAb 7D8 with these fibrils in the absence of peptope.

Similar EuLISA binding studies using biotinyl-7D8 were performed with human ATTR extracts from Sno (FIGS. 32 and 33) and Gre (FIGS. 34 and 35) as the substrate. The data show that mAb 7D8 does not significantly bind ATTR extract (FIG. 32 and FIG. 34; ▲) at the concentrations used in this study. When treated with peptope, the binding of 7D8 to ATTR amyloid is significantly enhanced, with an estimated $EC_{50}$ for Sno of 5 nM (estimation for Gre is not practical as the binding curve does approach saturation at the highest concentration of 7D8 used—FIG. 35).

The binding of 7D8 to human ATTR amyloid extracts was negligible at the concentrations of mAb studied in this assay (0.025-50 nM). However, after pre-targeting the synthetic fibrils or amyloid extracts with peptope reagents, the reactivity of 7D8 with these substrates improved ~100-1000-fold and, in most cases, resulted in $EC_{50}$ values of 1-5 nM, consistent with the affinity of the mAb for the epitope.

Immunohistochemistry

The binding of biotinyl-7D8 mAb with tissue amyloid, in situ, was assessed immunohistochemically using formalin-fixed, paraffin-embedded tissue sections of material obtained, at autopsy, from patients with ATTR or AL amyloidosis. The following data represent a series of studies using biotinyl-7D8 mAb and the p75 peptope, which was chosen as the exemplary peptope reagent as it exhibited, to a first approximation, the optimal pre-targeting properties. All images were captured using a 20× objective magnification, with the exception of Sno heart (40×).

We began by studying ATTR patient Gre, for whom we had multiple amyloid-laden tissue samples, derived from the esophagus, heart, nerve and bowel.

In the esophagus (FIGS. 36A-36D), there was evidence of weak "background" 7D8 reactivity with the amyloid, which was decreased by pre-treating the tissue sample with the negative control peptide, p5 (which lacks the 7D8 epitope sequence). The p5 peptide binds amyloid via predominantly electrostatic interacts; therefore, it is conceivable that addition of this peptide to the tissue blocked charged sites in the material with which the 7D8 mAb was non-specifically interacting. Pre-treatment of the tissue with peptope p75 resulted in dramatic, and amyloid-specific, binding of the 7D8, as evidenced by the dense brown DAB staining ("Peptope p75+7D8 IHC" image), which correlated excellently with the distribution of the tissue amyloid seen as red-green birefringent material in the Congo red-stained consecutive tissue section.

Similar findings were observed when using the Gre heart, nerve and bowel tissue (FIGS. 37A-38D, FIGS. 38A-38D, and FIGS. 39A-39D, respectively). In the heart, addition of 7D8 alone resulted in the staining of Congo-red-negative intracellular vesicles, which was partially inhibited by pre-treatment with the p5, control peptide. Although the amyloid was made evident by pre-targeting with p75, the non-specific intracellular vesicular uptake remained visible in this sample.

Non-specific uptake of 7D8 was not observed in the Gre nerve sample (FIGS. 38A-38D), which contrasted dramatically to the amyloid-specific uptake of the 7D8 mAb in the p75-pretreated tissue section. In the small bowel, weak background staining of 7D8 was observed. But, the specific binding to TTR amyloid was evidenced in the presence of p75.

In the Ken ATTR (FIGS. 40A-40D) and Sno ATTR (FIGS. 41A-41D) heart samples, there was significant background in the 7D8 stained tissue samples associated with cytoplasmic and vesicular uptake in the cardiomyocytes. Notably, in both cases, the amyloid was not stained when biotinyl-7D8 was used alone. As noted above, the background 7D8 staining was diminished by the addition of peptide p5. Only in the presence of peptope p75 was specific TTR amyloid immunostained with 7D8.

We also studied the reactivity of 7D8 with ALλ (FIGS. 42A-42D) and ALκ (FIGS. 43A-43D) tissue sections, which we had previously shown were unreactive with this mAb (and 2A4)—due to the formalin fixation. Both the ALλDen and ALκTa1 samples showed intense, non-amyloid related background binding of mAb 7D8 (or DAB in the case of tubular and glandular epithelia). In many areas, addition of the p5 inhibited this effect. Consistent, with the ATTR tissues, pre-treatment with peptope p75 resulted in significant amyloid-specific binding of the 7D8 mAb.

Phagocytosis Assay

The aim of this study was to assess the ability of peptope p75, in conjunction with mAb 7D8 to provide enhanced opsonization of human ATTR amyloid extract labeled with the pH-sensitive dye pHrodo.

Figure 44A:
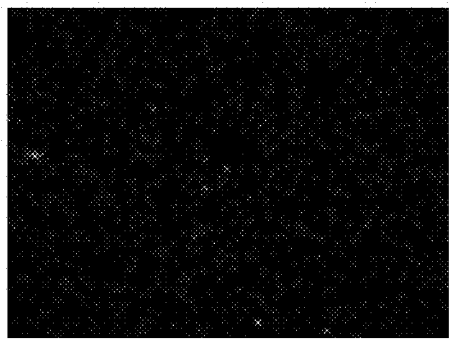
FIGS. 44A-44C are a series of micrographs showing the uptake of human ATTR amyloid (labeled with the pH sensitive dye pHrodo green) by human cultured macrophage cells in the presence of mAb 7D8 alone (FIG. 44A), or peptope p75 with a negative control mAb (MOPC) (FIG. 44B), or with peptope p75 and mAb 7D8 (FIG. 44C). Peptope+mAb 7D8 enhanced uptake of the amyloid by the cells.
Figure 44B:
Figure 44C:
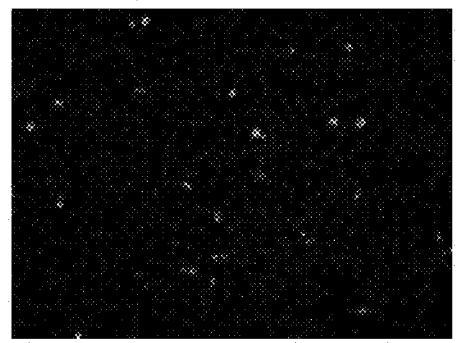

Uptake of ATTR amyloid by the murine RAW 264.7 macrophages was evidenced by fluorescence microscopy as punctate green fluorescent amyloid associated with the cells identified by the blue fluorescent nuclei (FIGS. 44A-44C). Qualitatively, in the absence of peptope p75 or using the MOPC control mAb there was less fluorescent amyloid as compared to the sample that included ATTR pretreated with p75 and mAb 75 (FIGS. 44A-44C). This data indicated that opsonization of ATTR amyloid by binding of peptope p75 and mAb 7D8 resulted in enhanced phagocytosis of the amyloid by macrophages—a process deemed to represent the mechanism of anti-amyloid immunotherapeutics.

Figure 45:
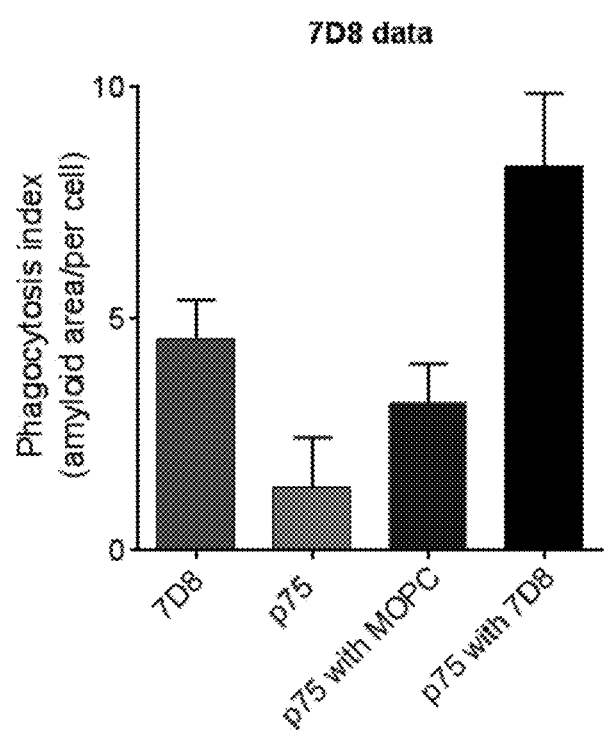
FIG. 45 is a graph showing the uptake of human ATTR amyloid (labeled with the pH sensitive dye pHrodo green) by human cultured macrophage cells in the presence of mAb 7D8 alone ("7D8"), peptope p75 alone ("p75"), peptope p75 with a negative control mAb ("p75 with MOPC"), or with peptope p75 and mAb 7D8 ("p75 with 7D8"). Peptope+mAb 7D8 significantly enhanced uptake of the amyloid by the cells.
Figure 46A:
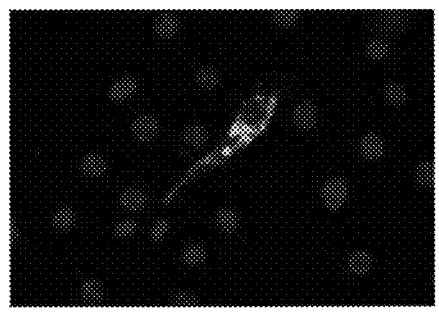
FIGS. 46A-46D are a series of micrographs showing the uptake of human ATTR amyloid (labeled with the pH sensitive dye pHrodo green), treated with peptope p75 and mAb 7D8, by human cultured macrophage cells, in accordance with certain example embodiments.
Figure 46B:
Figure 46C:
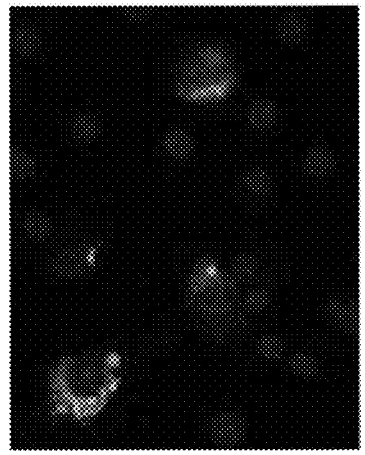
Figure 46D:
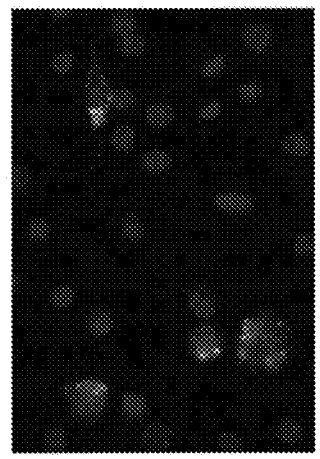

To quantify this effect the phagocytosis was repeated and the "phagocytosis index" (the area of green fluorescence per cell) measured (FIG. 45). In the presence of mAb 7D8 alone or p75+MOPC there was a basal level of ATTR amyloid phagocytosis, due to the inherent contact phagocytosis exhibited by macrophages. However, when opsonized with p75+7D8 uptake of the ATTR amyloid was significantly enhanced. It is worth noting that there is no evidence of macrophage-mediated amyloid phagocytosis in patients in the absence of opsonizing mAbs. Fluorescent human ATTR amyloid in the macrophages was imaged at high resolution to demonstrate the vesicular nature of the uptake, e.g. in phagolysosomes/endosomes (FIGS. 46A-46D). The results are shown below in Table 8 and in FIGS. 44A-44C, 45, and 46A-46D.

TABLE 8

| Tukey's multiple comparisons test | Mean Diff. | Significant? | Summary |
|---|---|---|---|
| 7D8 vs. p75 | 3.208 | Yes | * |
| 7D8 vs. p75 with MOPC | 1.382 | No | ns |
| 7D8 vs. p75 with 7D8 | −3.713 | Yes | * |
| p75 vs. p75 with MOPC | −1.825 | No | ns |
| p75 vs. p75 with 7D8 | −6.921 | Yes | *** |
| p75 with MOPC vs. p75 with 7D8 | −5.095 | Yes | ** |

| | 7D8 | p75 | p75 with MOPC | p75 with 7D8 |
|---|---|---|---|---|
| Number of values | 3 | 3 | 3 | 4 |
| Minimum | 3.987 | 0.5842 | 2.579 | 6.959 |
| 25% Percentile | 3.987 | 0.5842 | 2.579 | 7.031 |
| Median | 4.209 | 0.9137 | 2.842 | 7.875 |
| 75% Percentile | 5.528 | 2.603 | 4.156 | 9.956 |
| Maximum | 5.528 | 2.603 | 4.156 | 10.44 |
| Mean | 4.575 | 1.367 | 3.192 | 8.287 |
| Std. Deviation | 0.8330 | 1.083 | 0.8447 | 1.584 |
| Std. Error of Mean | 0.4809 | 0.6252 | 0.4877 | 0.7922 |
| Lower 95% CI | 2.505 | −1.323 | 1.094 | 5.766 |
| Upper 95% CI | 6.644 | 4.057 | 5.291 | 10.81 |

Discussion

The aim of these studies was to further characterize the ability of four peptide peptide sequences to enhance and expand the reactivity of the mAb 7D8. The bifunctional peptope sequences combine the pan-amyloid reactive peptide p5 with the -His-Glu-Asp-Thr-COOH epitope (SEQ ID NO: 52) associated via a 3 amino acid linker. It is the linker sequence that appears to differentiate each of the four peptopes. The mAb 7D8 binds both human and murine AA amyloid, as well as human ALκ and ALλ amyloid deposits via a cryptic epitope expressed on the C-terminally truncated or fibrillar form of the precursor proteins, respectively. The 7D8 mAb has been shown to not bind ATTR amyloid. A further goal of this study was to differentiate, quantitatively, the efficacy of each of the four peptide sequences.

To approximate the amyloid-bound form of the peptopes, each was amino-coupled to polystyrene beads via the lysine side chains in the p5 moiety, which are known to be critical for the engagement with amyloid. Using a solution phase binding pulldown assay, we showed that $^{125}$I-7D8 bound each of the peptopes. This assay also provided the first indication that peptope p75 was more efficacious under these conditions. As noted above, peptope p75 was found to have a KD of ~1-5 nM, based on surface plasmon resonance measurements, similar to the other peptopes; however, the p75 binding kinetics were characterized by a slow and reduced off-rate, relative to the other peptopes.

Binding of $^{125}$I-7D8 to synthetic fibrils composed of Aβ (1-40) or IAPP, using the pulldown assay, was significantly enhanced, 5-10-fold, when the fibrils were pre-treated with the peptope. When human ATTR extract from three different patients was assayed in the pulldown system, the reactivity was lower than that seen for the pure synthetic Aβ (1-40) or IAPP fibrils; however the reactivity of $^{125}$I-7D8 with the extracts was significantly enhanced when the amyloid was pre-treated with each of the peptopes. In these assays, the p75 peptope was more efficacious at enhancing the reactivity of the 7D8 mAb. As noted earlier, we have shown that peptide p5 is not the optimal ATTR amyloid-binding peptide. Rather, the extended variant, p5+14, was found to bind TTR amyloid more effectively than peptide p5, pSR, or p5R+14. Therefore, to generate a TTR-optimized peptope for 7D8 (as well as the 2A4 and 8G9 mAbs, for example) it may be beneficial to generate a peptope with the following structure: p5+14-QAQ-HEDT ("QAQ-HEDT" disclosed as SEQ ID NO: 56), for example.

Quantitative binding to synthetic fibrils and ATTR extracts was measured by using a EuLISA. In these assays, the reactivity of biotinylated 7D8 was increased 100-1000 fold when the substrate was pre-treated with peptope. These data are consistent with the pulldown data. The estimated EC50 for the binding of 7D8 with peptope-treated fibrils and human ATTR extracts was ~1-10 nM. These data indicate that the use of peptope pre-targeting can expand the utility of mAb 7D8, and equivalent reagents, for use with amyloid deposits other than AA and AL, and it may also enhance the efficacy of binding to AL deposits that are not rich in the abundance of the natural AL-related 7D8 epitope.

This was further demonstrated immunohistochemically using biotinylated mAb 7D8. In this study, we focused principally on ATTR-laden human FFPE tissue sections since ATTR is arguably the most common systemic amyloid diseases in man. We evaluated three patients with hereditary ATTR amyloidosis, including multiple tissue sites from a single patient. In all cases, a certain degree of weak, non-amyloid associated, non-specific staining was observed when biotinyl-7D8 mAb was used alone (FIGS. 36-41). However, when the tissue sections were pre-treated with peptope p75, our "optimal" agent, specific and intense staining of the amyloid was achieved in all tissues evaluated. These data indicate that peptope-targeting may be a valuable tool to direct mAb 7D8 to non-AL or AA amyloid deposits.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

---

What is claimed is:

1. A method of targeting an amyloid deposit for clearance, comprising:
   contacting an amyloid deposit of a first amyloid type with an amyloid-reactive fusion peptide, wherein the amyloid-reactive fusion peptide comprises an amyloid-reactive peptide at least 95% identical to any one of the amino acid sequences set forth as SEQ ID NOS: 1-17 and an HEDT amino acid sequence epitope (SEQ ID NO: 52);
   contacting the amyloid-reactive fusion peptide with an antibody or functional fragment thereof, wherein the antibody or functional fragment thereof is immunoreactive to a second amyloid type that is different than the first amyloid type and wherein the HEDT epitope (SEQ ID NO: 52) of the amyloid-reactive fusion peptide directs the antibody or functional fragment thereof to the first amyloid type, thereby targeting the amyloid deposit of the first amyloid type for clearance.

2. The method of claim 1, wherein targeting the amyloid deposit for clearance results in clearance of the amyloid deposit.

3. The method of claim 1, wherein the second amyloid type is AA amyloid or AL amyloid and the antibody or functional fragment thereof is immunoreactive to the AA amyloid or AL amyloid.

4. The method of claim 3, wherein the antibody is a 7D8, 2A4, or 8G9 antibody or functional fragment thereof or variant thereof.

5. The method of claim 4, wherein the first amyloid type is AH, ATTR, Aβ2M, ALect2, Wild type (wt) TTR, AApoAII, AGel, ALys, Afib, ACys, ACal, AMedin, AIAPP, APro, AIns, APrP, or Aβ.

6. The method of claim 1, wherein the amyloid-reactive peptide comprising the HEDT epitope (SEQ ID NO: 52) is at least 95% identical to the amino acid sequence set forth as SEQ ID NO:26.

7. The method of claim 1, wherein the amyloid-reactive peptide comprising the HEDT epitope (SEQ ID NO: 52) is at least 95% identical to the amino acid sequence set forth as SEQ ID NO:31.

8. A method for treating amyloidosis in a subject, comprising:
   administering to a subject having a first amyloid type an amyloid-reactive fusion peptide, the amyloid-reactive fusion peptide comprising an amyloid-reactive peptide at least 95% identical to any one of the amino acid sequences set forth as SEQ ID NOS: 1-17 and an HEDT amino acid sequence epitope (SEQ ID NO: 52);
   administering to the subject an antibody or functional fragment thereof that is immunoreactive to a second amyloid type and that binds to the HEDT epitope (SEQ ID NO: 52) of the amyloid-reactive fusion peptide, wherein administration of the antibody or functional fragment thereof to the subject targets the first amyloid type for clearance, the second amyloid type being different than the first amyloid type.

9. The method of claim 8, further comprising testing the subject to determine whether the subject has amyloidosis before administering the amyloid-reactive fusion peptide or the antibody or functional fragment thereof.

10. The method of claim 8, wherein the second amyloid type is AA amyloid or AL amyloid and the antibody or functional fragment thereof is immunoreactive to the AA amyloid or AL amyloid.

11. The method of claim 10, wherein administration of the antibody or functional fragment thereof results in clearance of an amyloid deposit comprising the first amyloid type.

12. The method of claim 10, wherein the antibody is a 7D8, 2A4, or 8G9 antibody or functional fragment thereof or variant thereof.

13. The method of claim 10, wherein the first amyloid type is AH, ATTR, Aβ2M, Wild type (wt) TTR, AApoAII, AGel, ALys, ALect2, Afib, ACys, ACal, AMedin, AIAPP, APro, AIns, APrP, or Aβ.

14. The method of claim 8, wherein the amyloid-reactive fusion peptide comprising the HEDT sequence (SEQ ID NO: 52) is at least 95% identical the amino acid sequence set forth as SEQ ID NO:26.

15. A method of targeting an antibody or functional fragment thereof to an amyloid deposit in a subject, comprising:
   administering to a subject having a first amyloid type an effective amount of an amyloid-reactive fusion peptide, wherein the amyloid-reactive fusion peptide comprises an amyloid-reactive peptide comprising at least 95% identity to any one of the amino acid sequences set forth as SEQ ID NOS: 1-17 and an HEDT epitope (SEQ ID NO: 52), the HEDT epitope (SEQ ID NO: 52) comprising binding affinity for an antibody or functional fragment thereof that is immunoreactivity to a second amyloid type that is different from the first amyloid type; and,
   administering to the subject an effective amount of the antibody or functional fragment thereof, thereby targeting the antibody or functional fragment thereof to the first amyloid type.

16. The method of claim 15, wherein targeting the antibody or functional fragment thereof to the first amyloid type results in clearance of an amyloid deposit comprising the first amyloid type.

17. The method of claim 15, wherein the second amyloid type is AA amyloid or AL amyloid.

18. The method of claim 15, wherein the first amyloid type is AH, ATTR, Aβ2M, Wild type (wt) TTR, AApoAI, AGel, ALys, ALect2, Afib, ACys, ACal, AMedin, AIAPP, APro, AIns, APrP, or Aβ.

19. The method of claim 15, wherein the amyloid-reactive fusion peptide is at least 95% identical the amino acid sequence set forth as SEQ ID NO:26.

20. The method of claim 15, wherein the amyloid-reactive fusion peptide is at least 95% identical the amino acid sequence set forth as SEQ ID NO:31.

* * * * *

SEQUENCE LISTING

```
<160> NUMBER OF SEQ ID NOS: 56

<210> SEQ ID NO 1
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide p5

<400> SEQUENCE: 1

Lys Ala Gln Lys Ala Gln Ala Lys Gln Ala Lys Gln Ala Gln Lys Ala
1               5                   10                  15

Gln Lys Ala Gln Ala Lys Gln Ala Lys Gln
            20                  25

<210> SEQ ID NO 2
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide p5R

<400> SEQUENCE: 2
```

Arg Ala Gln Arg Ala Gln Ala Arg Gln Ala Arg Gln Ala Gln Arg Ala
1               5                   10                  15

Gln Arg Ala Gln Ala Arg Gln Ala Arg Gln
            20                  25

<210> SEQ ID NO 3
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide p5G

<400> SEQUENCE: 3

Gly Ala Gln Gly Ala Gln Ala Gly Gln Ala Gly Gln Ala Gln Gly Ala
1               5                   10                  15

Gln Gly Ala Gln Ala Gly Gln Ala Gly Gln
            20                  25

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide p8

<400> SEQUENCE: 4

Lys Ala Lys Ala Lys Ala Lys Ala Lys Ala Lys Ala Lys Ala Lys
1               5                   10                  15

<210> SEQ ID NO 5
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide p9

<400> SEQUENCE: 5

Lys Ala Gln Ala Lys Ala Gln Ala Lys Ala Gln Ala Lys Ala Gln Ala
1               5                   10                  15

Lys Ala Gln Ala Lys Ala Gln Ala Lys Ala Gln Ala Lys
            20                  25

<210> SEQ ID NO 6
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide p20

<400> SEQUENCE: 6

Lys Ala Gln Gln Ala Gln Ala Lys Gln Ala Gln Gln Ala Gln Lys Ala
1               5                   10                  15

Gln Gln Ala Gln Ala Lys Gln Ala Gln Gln
            20                  25

```
<210> SEQ ID NO 7
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide p20

<400> SEQUENCE: 7

Gln Ala Gln Lys Ala Gln Ala Gln Gln Ala Lys Gln Ala Gln Gln Ala
1               5                   10                  15

Gln Lys Ala Gln Ala Gln Gln Ala Lys Gln
            20                  25

<210> SEQ ID NO 8
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide p31

<400> SEQUENCE: 8

Lys Ala Gln Lys Ala Gln Ala Lys Gln Ala Lys Gln Ala Gln Lys Ala
1               5                   10                  15

Gln Lys Ala Gln Ala Lys Gln Ala Lys Gln
            20                  25

<210> SEQ ID NO 9
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide p37

<400> SEQUENCE: 9

Lys Thr Val Lys Thr Val Thr Lys Val Thr Lys Val Thr Val Lys Thr
1               5                   10                  15

Val Lys Thr Val Thr Lys Val Thr Lys Val
            20                  25

<210> SEQ ID NO 10
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide p39
<220> FEATURE:
<221> NAME/KEY: MOD_RES
<222> LOCATION: (1)..(26)
<223> OTHER INFORMATION: D-amino acid

<400> SEQUENCE: 10

Lys Ala Gln Lys Ala Gln Ala Lys Gln Ala Lys Gln Ala Gln Lys Ala
1               5                   10                  15

Gln Lys Ala Gln Ala Lys Gln Ala Lys Gln
```

```
                    20                  25

<210> SEQ ID NO 11
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide p42
<220> FEATURE:
<221> NAME/KEY: MOD_RES
<222> LOCATION: (2)..(2)
<223> OTHER INFORMATION: D-amino acid

<400> SEQUENCE: 11

Val Tyr Lys Val Lys Thr Lys Val Lys Thr Lys Val Lys Thr Lys Val
1               5                   10                  15

Lys Thr

<210> SEQ ID NO 12
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Peptide p43
<220> FEATURE:
<221> NAME/KEY: MOD_RES
<222> LOCATION: (1)..(3)
<223> OTHER INFORMATION: D-amino acid

<400> SEQUENCE: 12

Ala Gln Ala Tyr Ser Lys Ala Gln Lys Ala Gln Ala Lys Gln Ala Lys
1               5                   10                  15

Gln Ala Gln Lys Ala Gln Lys Ala Gln Ala Lys Gln Ala Lys Gln
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Peptide p44
<220> FEATURE:
<221> NAME/KEY: MOD_RES
<222> LOCATION: (1)..(3)
<223> OTHER INFORMATION: D-amino acid

<400> SEQUENCE: 13

Ala Gln Ala Tyr Ala Arg Ala Gln Arg Ala Gln Ala Arg Gln Ala Arg
1               5                   10                  15

Gln Ala Gln Arg Ala Gln Arg Ala Gln Ala Arg Gln Ala Arg Gln
            20                  25                  30

<210> SEQ ID NO 14
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

<223> OTHER INFORMATION: Peptide p48
<220> FEATURE:
<221> NAME/KEY: MOD_RES
<222> LOCATION: (4)..(31)
<223> OTHER INFORMATION: D-amino acid

<400> SEQUENCE: 14

Ala Gln Ala Tyr Ser Lys Ala Gln Lys Ala Gln Ala Lys Gln Ala Lys
1               5                   10                  15

Gln Ala Gln Lys Ala Gln Lys Ala Gln Ala Lys Gln Ala Lys Gln
            20                  25                  30

<210> SEQ ID NO 15
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Peptide p50

<400> SEQUENCE: 15

Ala Gln Ala Tyr Ser Lys Ala Gln Lys Ala Gln Ala Lys Gln Ala Lys
1               5                   10                  15

Gln Ala Gln Lys Ala Gln Lys Ala Gln Ala Lys Gln Ala Lys Gln
            20                  25                  30

<210> SEQ ID NO 16
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Peptide p58
<220> FEATURE:
<221> NAME/KEY: MOD_RES
<222> LOCATION: (4)..(4)
<223> OTHER INFORMATION: D-amino acid

<400> SEQUENCE: 16

Ala Gln Ala Tyr Ser Lys Ala Gln Lys Ala Gln Ala Lys Gln Ala Lys
1               5                   10                  15

Gln Ala Gln Lys Ala Gln Lys Ala Gln Ala Lys Gln Ala Lys Gln
            20                  25                  30

<210> SEQ ID NO 17
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Peptide p5+14

<400> SEQUENCE: 17

Lys Ala Gln Lys Ala Gln Ala Lys Gln Ala Lys Gln Ala Gln Lys Ala
1               5                   10                  15

Gln Lys Ala Gln Ala Lys Gln Ala Gln Ala Gln Lys Ala Gln Lys
            20                  25                  30

Ala Gln Ala Lys Gln Ala Lys Gln
        35                  40

```
<210> SEQ ID NO 18
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Fusion protein between p66 and antibody epitope
      sequence 11-1F4

<400> SEQUENCE: 18

Lys Ala Gln Lys Ala Gln Ala Lys Gln Ala Lys Gln Ala Gln Lys Ala
1               5                   10                  15

Gln Lys Ala Gln Ala Lys Gln Ala Lys Gln Ala Lys Ala Gln Lys
            20                  25                  30

Ala Gln Ala Lys Gln Ala Lys Gln Ser Val Thr Val Val Thr Lys His
        35                  40                  45

Tyr Ala Ala Phe Pro Glu Asn Leu Leu Ile
    50                  55

<210> SEQ ID NO 19
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Fusion protein of p66 with 11-1F4 antibody
      epitope including a linker sequence
<220> FEATURE:
<221> NAME/KEY: MOD_RES
<222> LOCATION: (41)..(46)
<223> OTHER INFORMATION: Any amino acid

<400> SEQUENCE: 19

Lys Ala Gln Lys Ala Gln Ala Lys Gln Ala Lys Gln Ala Gln Lys Ala
1               5                   10                  15

Gln Lys Ala Gln Ala Lys Gln Ala Lys Gln Ala Lys Ala Gln Lys
            20                  25                  30

Ala Gln Ala Lys Gln Ala Lys Gln Xaa Xaa Xaa Xaa Xaa Xaa Lys His
        35                  40                  45

Tyr Ala Ala Phe Pro Glu Asn Leu Leu Ile
    50                  55

<210> SEQ ID NO 20
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Fusion peptide of p66 with antibody epitope
      sequence and a linker
<220> FEATURE:
<221> NAME/KEY: MOD_RES
<222> LOCATION: (41)..(60)
<223> OTHER INFORMATION: Any amino acid
<220> FEATURE:
<221> NAME/KEY: MISC_FEATURE
<222> LOCATION: (41)..(60)
<223> OTHER INFORMATION: This region may encompass 1-20 residues

<400> SEQUENCE: 20

Lys Ala Gln Lys Ala Gln Ala Lys Gln Ala Lys Gln Ala Gln Lys Ala
1               5                   10                  15
```

```
Gln Lys Ala Gln Ala Lys Gln Ala Lys Gln Ala Gln Lys
            20                  25                  30

Ala Gln Ala Lys Gln Ala Lys Gln Xaa Xaa Xaa Xaa Xaa Xaa Xaa
            35                  40                  45

Xaa Xaa Xaa Xaa Xaa Xaa Xaa Xaa Xaa Xaa Xaa Lys His Tyr Ala
    50                  55                  60

Ala Phe Pro Glu Asn Leu Leu Ile
65                  70

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker sequence

<400> SEQUENCE: 21

Ser Val Thr Val Val Thr
1               5

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Len-based peptide epitope

<400> SEQUENCE: 22

Asp Ile Val Met Thr Gln Ser Pro Asp Ser Leu Ala Val Ser Leu Gly
1               5                   10                  15

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Antibody epitope sequence 11-1F4

<400> SEQUENCE: 23

Lys His Tyr Ala Ala Phe Pro Glu Asn Leu Leu Ile
1               5                   10

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Functional leader sequence

<400> SEQUENCE: 24

Gly Gly Gly Tyr Ser
1               5

<210> SEQ ID NO 25
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Functional leader sequence

<400> SEQUENCE: 25

Cys Gly Gly Tyr Ser
1               5

<210> SEQ ID NO 26
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Lys Ala Gln Lys Ala Gln Ala Lys Gln Ala Lys Gln Ala Gln Lys Ala
1               5                   10                  15

Gln Lys Ala Gln Ala Lys Gln Ala Lys Gln Ala Gln His Glu Asp Thr
            20                  25                  30

<210> SEQ ID NO 27
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Lys Ala Gln Lys Ala Gln Ala Lys Gln Ala Lys Gln Ala Gln Lys Ala
1               5                   10                  15

Gln Lys Ala Gln Ala Lys Gln Ala Lys Gln Gly Gly Gly His Glu Asp
            20                  25                  30

Thr

<210> SEQ ID NO 28
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Lys Ala Gln Lys Ala Gln Ala Lys Gln Ala Lys Gln Ala Gln Lys Ala
1               5                   10                  15

Gln Lys Ala Gln Ala Lys Gln Ala Lys Gln Gly Pro Gly His Glu Asp
            20                  25                  30

Thr

<210> SEQ ID NO 29
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29
```

```
Lys Ala Gln Lys Ala Gln Ala Lys Gln Ala Lys Gln Ala Gln Lys Ala
1               5                   10                  15

Gln Lys Ala Gln Ala Lys Gln Ala Lys Gln Val Thr Val His Glu Asp
            20                  25                  30

Thr

<210> SEQ ID NO 30
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (41)..(60)
<223> OTHER INFORMATION: Any amino acid
<220> FEATURE:
<221> NAME/KEY: MISC_FEATURE
<222> LOCATION: (41)..(60)
<223> OTHER INFORMATION: This region may encompass 1-20 residues

<400> SEQUENCE: 30

Lys Ala Gln Lys Ala Gln Ala Lys Gln Ala Lys Gln Ala Gln Lys Ala
1               5                   10                  15

Gln Lys Ala Gln Ala Lys Gln Ala Lys Gln Ala Gln Lys Ala Gln Lys
            20                  25                  30

Ala Gln Ala Lys Gln Ala Lys Gln Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa His Glu Asp Thr
    50                  55                  60

<210> SEQ ID NO 31
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Lys Ala Gln Lys Ala Gln Ala Lys Gln Ala Lys Gln Ala Gln Lys Ala
1               5                   10                  15

Gln Lys Ala Gln Ala Lys Gln Ala Lys Gln Ala Gln Lys Ala Gln Lys
            20                  25                  30

Ala Gln Ala Lys Gln Ala Lys Gln Gln Ala Gln His Glu Asp Thr
        35                  40                  45

<210> SEQ ID NO 32
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (33)..(33)
<223> OTHER INFORMATION: Any amino acid

<400> SEQUENCE: 32
```

```
Lys Ala Gln Lys Ala Gln Ala Lys Gln Ala Lys Gln Ala Gln Lys Ala
1               5                   10                  15

Gln Lys Ala Gln Ala Lys Gln Ala Lys Gln Gly Ala Xaa Glu Asp
            20                  25                  30

Xaa
```

<210> SEQ ID NO 33
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (44)..(44)
<223> OTHER INFORMATION: Any amino acid
<220> FEATURE:
<221> NAME/KEY: MOD_RES
<222> LOCATION: (47)..(47)
<223> OTHER INFORMATION: Any amino acid

<400> SEQUENCE: 33

```
Lys Ala Gln Lys Ala Gln Ala Lys Gln Ala Lys Gln Ala Gln Lys Ala
1               5                   10                  15

Gln Lys Ala Gln Ala Lys Gln Ala Lys Gln Ala Gln Lys Ala Gln Lys
            20                  25                  30

Ala Gln Ala Lys Gln Ala Lys Gln Gly Ala Gln Xaa Glu Asp Xaa
            35                  40                  45
```

<210> SEQ ID NO 34
<211> LENGTH: 4
<212> TYPE: PRT
<213> ORGANISM: Homo sapiens

<400> SEQUENCE: 34

```
Ala Glu Asp Ser
1
```

<210> SEQ ID NO 35
<211> LENGTH: 4
<212> TYPE: PRT
<213> ORGANISM: Homo sapiens

<400> SEQUENCE: 35

```
Ala Glu Asp Val
1
```

<210> SEQ ID NO 36
<211> LENGTH: 4
<212> TYPE: PRT
<213> ORGANISM: Homo sapiens

<400> SEQUENCE: 36

```
Pro Glu Asp Ser
1
```

<210> SEQ ID NO 37
<211> LENGTH: 4
<212> TYPE: PRT
<213> ORGANISM: Homo sapiens

<400> SEQUENCE: 37

```
Ser Glu Asp Phe
1
```

```
<210> SEQ ID NO 38
<211> LENGTH: 4
<212> TYPE: PRT
<213> ORGANISM: Homo sapiens

<400> SEQUENCE: 38

Pro Glu Asp Phe
1

<210> SEQ ID NO 39
<211> LENGTH: 4
<212> TYPE: PRT
<213> ORGANISM: Homo sapiens

<400> SEQUENCE: 39

Pro Glu Asp Leu
1

<210> SEQ ID NO 40
<211> LENGTH: 4
<212> TYPE: PRT
<213> ORGANISM: Homo sapiens

<400> SEQUENCE: 40

Thr Glu Asp Val
1

<210> SEQ ID NO 41
<211> LENGTH: 4
<212> TYPE: PRT
<213> ORGANISM: Homo sapiens

<400> SEQUENCE: 41

Pro Glu Asp Val
1

<210> SEQ ID NO 42
<211> LENGTH: 4
<212> TYPE: PRT
<213> ORGANISM: Homo sapiens

<400> SEQUENCE: 42

Pro Glu Asp Ile
1

<210> SEQ ID NO 43
<211> LENGTH: 4
<212> TYPE: PRT
<213> ORGANISM: Homo sapiens

<400> SEQUENCE: 43

Leu Glu Asp Gly
1

<210> SEQ ID NO 44
<211> LENGTH: 4
<212> TYPE: PRT
<213> ORGANISM: Homo sapiens

<400> SEQUENCE: 44

Ala Glu Asp Glu
1
```

```
<210> SEQ ID NO 45
<211> LENGTH: 4
<212> TYPE: PRT
<213> ORGANISM: Homo sapiens

<400> SEQUENCE: 45

Ala Glu Asp Met
1

<210> SEQ ID NO 46
<211> LENGTH: 4
<212> TYPE: PRT
<213> ORGANISM: Homo sapiens

<400> SEQUENCE: 46

Ser Glu Asp Ile
1

<210> SEQ ID NO 47
<211> LENGTH: 4
<212> TYPE: PRT
<213> ORGANISM: Homo sapiens

<400> SEQUENCE: 47

Ala Glu Asp Ala
1

<210> SEQ ID NO 48
<211> LENGTH: 4
<212> TYPE: PRT
<213> ORGANISM: Homo sapiens

<400> SEQUENCE: 48

His Glu Asp Ser
1

<210> SEQ ID NO 49
<211> LENGTH: 4
<212> TYPE: PRT
<213> ORGANISM: Homo sapiens

<400> SEQUENCE: 49

Cys Glu Asp Asp
1

<210> SEQ ID NO 50
<211> LENGTH: 4
<212> TYPE: PRT
<213> ORGANISM: Homo sapiens

<400> SEQUENCE: 50

Thr Glu Asp Glu
1

<210> SEQ ID NO 51
<211> LENGTH: 4
<212> TYPE: PRT
<213> ORGANISM: Homo sapiens

<400> SEQUENCE: 51

Ser Glu Asp Glu
1

<210> SEQ ID NO 52
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

His Glu Asp Thr
1

<210> SEQ ID NO 53
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 53

Xaa Glu Asp Xaa
1

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Cys Gly Gly His Glu Asp Thr
1               5

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Cys Gly Gly His Glu Asp Thr Met Ala Asp Gln Glu
1               5                   10

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Ala Gln His Glu Asp Thr
1               5
```